Figure 1:
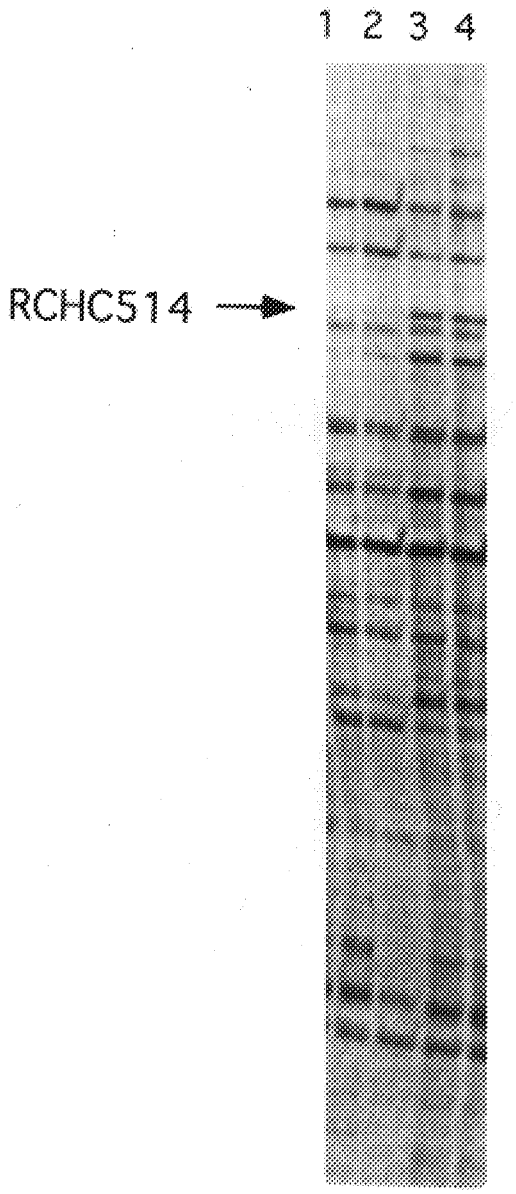

US005849578A

United States Patent [19]

Falb

[11] Patent Number: 5,849,578

[45] Date of Patent: Dec. 15, 1998

[54] COMPOSITIONS AND METHODS FOR THE TREATMENT AND DIAGNOSIS OF CARDIOVASCULAR USING RCHD528 AS A TARGET

[75] Inventor: Dean A. Falb, Massachusetts, Mass.

[73] Assignee: Millennium Pharmaceuticals, Inc., Cambridge, Mass.

[21] Appl. No.: 616,844

[22] Filed: Mar. 15, 1996

Related U.S. Application Data

[60] Division of Ser. No. 599,654, Feb. 9, 1996, which is a continuation-in-part of Ser. No. 458,873, Jun. 7, 1995, which is a continuation-in-part of Ser. No. 386,844, Feb. 10, 1995.

[51] Int. Cl.[6] .................... C12N 15/12

[52] U.S. Cl. .................... 435/325; 536/23.1; 536/24.1; 536/24.3; 435/6; 435/69.1; 435/320.1; 435/455

[58] Field of Search .................... 536/23.1, 24.1, 536/24.3; 435/6, 69.1, 7.1, 325, 320.1, 455; 436/201, 63; 514/44

[56] References Cited

U.S. PATENT DOCUMENTS

| | | | |
|---|---|---|---|
| 5,418,162 | 5/1995 | Blakely et al. | 435/252.3 |
| 5,424,187 | 6/1995 | Shor et al. | 435/647.1 |
| 5,545,569 | 8/1996 | Grainger et al. | 436/518 |

FOREIGN PATENT DOCUMENTS

| | | |
|---|---|---|
| 0 282 899 A2 | 9/1988 | European Pat. Off. . |
| 0 670 369 A2 | 9/1995 | European Pat. Off. . |
| WO 95/23858 | 9/1995 | WIPO . |

OTHER PUBLICATIONS

W.M. Barnes, 1994, "PCR amplification of up to 35–kb DNA with high fidelity and high yield from λ bacteriophage templates", *Proc. Natl. Acad. Sci. USA* 91:2216–2220.

Bevilacqua et al., 1989, "Endothelial leukocyte adhesion molecule 1: An inducible receptor for neutrophils related to complement regulatory proteins and lectins", *Science* 243:1160–1165.

Bevilacqua et al., 1991, "Selectins: A family of adhesion receptors", *Cell* 67:233.

Black et al., 1994, "Raloxifene (LY139481 HCI) prevents bone loss and reduces serum cholesterol without causing uterine hypertrophy on ovariectomized rats", *J. Clin. Invest.* 93:63–69.

Boise et al. 1993, "bcl–x, a bcl–2–Related gene that functions as a dominant regulator of apoptotic cell death", *Cell* 74:597–608.

Cercek et al., 1990, "Induction of insulin–like growth factor I messenger RNA in rat aorta after balloon denudation", *Circulation Res.* 66:1755–1760.

Cheng et al., 1994, "Effective amplication of long targets from cloned inserts and human genomic DNA", *Proc. Natl. Acad. Sci. USA* 91:5695–5699.

Cleary et al., 1986, "Cloning and structural analysis of cDNAs for bcl–2 and a hybrid bcl–2/Immunoglobulin transcript resulting from the t(14;18) translocation", *Cell* 47:19–28.

Coffman et al., 1990, "Xotch, the Xenopus homolog of Drosophila Notch", *Science* 249:1438–1441.

Cybulsky & Gimbrone, 1991, "Endothelial expression of a mononuclear leukocyte adhesion molecule during atherogenesis", *Science* 251:788–791.

Davies et al., 1986, "Turbulent fluid shear stress induces vascular endothelial cell turnover in vitro", *Proc. Nat. Acad. Sci. USA* 83:2114–2117.

M.A. Gimbrone, 1976, "Culture of vascular endothelium" *Progress in Hemostasis and Thrombosis* Grune & Stratton Inc., NY, 3:1–28.

Gromadzinska & Sklodowska, 1990, "Erythrocyte glutathione peroxidase and myocardial infarction", *JAMA* 263:949–950.

Guidi et al., 1986, "Platelet glutathione peroxidase activity is impaired in patients with coronary heart disease", *J. Clin. Lab Invest.* 46:549–551.

Hakes & Berezney, 1991, "Molecular cloning of matrix F/G: A DNA binding protein of the nuclear matrix that contains putative zinc finger motifs", *Proc. Natl. Acad. Sci. USA* 88:6186–6190.

K. Heckl. 1988, "Isolation of cNDAs encoding human manganese superoxide dismutase", *Nucl. Acids Res.* 16:6224.

Hockenbery et al., 1993, "Bcl–2 functions in an antioxidant pathway to prevent apoptosis", *Cell* 75:241–251.

Jones et al., 1993, "Molecular cloning of human prostaglandin endoperoxide synthase type II and demonstration of expression in response to cytokines", *J. Biol. Chem.* 268:9049–9054.

(List continued on next page.)

*Primary Examiner*—Christopher S. F. Low
*Assistant Examiner*—Dave Trong Nguyen
*Attorney, Agent, or Firm*—Pennie & Edmonds

[57] ABSTRACT

The present invention relates to methods and compositions for the treatment and diagnosis of cardiovascular disease, including, but not limited to, atherosclerosis, ischemia/reperfusion, hypertension, restenosis, and arterial inflammation. Specifically, the present invention identifies and describes genes which are differentially expressed in cardiovascular disease states, relative to their expression in normal, or non-cardiovascular disease states, and/or in response to manipulations relevant to cardiovascular disease. Further, the present invention identifies and describes genes via the ability of their gene products to interact with gene products involved in cardiovascular disease. Still further, the present invention provides methods for the identification and therapeutic use of compounds as treatments of cardiovascular disease. Moreover, the present invention provides methods for the diagnostic monitoring of patients undergoing clinical evaluation for the treatment of cardiovascular disease, and for monitoring the efficacy of compounds in clinical trials. Additionally, the present invention describes methods for the diagnostic evaluation and prognosis of various cardiovascular diseases, and for the identification of subjects exhibiting a predisposition to such conditions.

21 Claims, 53 Drawing Sheets

OTHER PUBLICATIONS

Kita et al., 1987, "Probucol prevents the progression of atherosclerosis in Watanabe heritable hyperlipidemic rabbit, an animal model for familial hypercholesterolemia", *Proc. Natl. Acad. Sci. USA* 84:5928–5931.

Kok et al., 1989, "Decreased selenium levels in acute myocardial infarction", *JAMA* 261:1161–1164.

Kumar & Chambon, 1988, "The estrogen receptor binds tightly to its responsive element as a ligand–induced homodimer", *Cell* 55:145–156.

Kume et al., 1992, "Lysophosphatidylcholine, a component of atherogenic lipoprotein, induces mononuclear leukocyte adhesion molecules in cultured human and rabbit arterial endothelial cells", *J. Clin. Invest.* 90:1138–1144.

Majesky et al., 1990, "PDGF ligand and receptor gene expression during repair of arterial injury", *J. Cell Biol.* 111:2149–2158.

Malden et al., 1991, "The influence of oxidatively modified low density lipoproteins on exprssion of platelet–derived growth factor by human monocyte–derived macrophages", *J. Biol. Chem.* 266:13901–13907.

Nagel et al., 1994, "Shear stress selectively upregualtes intercellular adhesion molecule–1 expression in cultured human vascular endothelial cells", *J. Clin. Invest.* 94:885–891.

Navab et al., 1988, "Monocyte migration into the subendothelial space of a coculture of adult human aortic endothelial and smooth muscle cells", *J. Clin. Invest.* 82:1853–1863.

Ohno et al., 1994, "Gene therapy for vascular smooth muscle cell proliferation after arterial injury", *Science* 265:781–784.

Oltvai et al., 1993, "Bcl–2 heterodimerizes in vivo with a conserved homolog, bax, that accelerates programed cell death", *Cell* 74:609–619.

Osborn et al., 1989, "Direct expression cloning of vascular cell adhesion molecule 1, a cytokine–induced endothelial protein that binds to lymphocytes", *Cell* 59:1203–1211.

Plump et al., 1992, "Severe hypercholesterolemia and atherosclerosis in apolipoprotein e–deficient mice created by homologous recombination in ES cells", *Cell* 71:343–353.

Porter et al., 1992, "Plasma, platelet and erythrocyte glutathione peroxidase as risk factors in ischaemic heart disease in man", *Clinical Science* 83:343–345.

Poston et al., 1992, "Expression of intercellular adhesion molecule–1 in atherosclerotic plaques", *Am. J. Pathol.* 140:665–673.

Rapacz et al., 1986, "Lipoprotein mutations in pigs are associated with elevated plasma cholesterol and atherosclerosis", *Science* 234:1573–1577.

Resnick et al., 1993, "Platelet–derived growth factor B chain promoter contains a cis–acting fluid shear–stress–responsive element", *Proc. Natl. Acad. Sci. USA* 90:4591–4595.

R. Ross, 1993, "The pathogenesis of atherosclerosis: Perspective for the 1990s", *Nature* 362:801–809.

Simmons et al., 1988, "ICAM, and adheson ligand of LFA–1, is homologous to neural cell adhesion molecule NCAM", *Nature* 331:624–627.

Speir et al., 1994, "Potential role of human cytomegalovirus and p53 interaction in coronary restenosis", *Science* 265:391–394.

Shreeniwas et al., 1991, "Reoxygenation stimulates IL–1α production, increasing leukocyte adherence to endothelium via expression of ICAM–1 and ELAM–1", *Arterioscler. Council Abstracts* 11:1397a.

Takahashi et al., 1990, "Primary structure of human plasma glutathione peroxidase deduced from cDNA sequences", *J. Biochem.* 108:145–148.

Takayama et al., 1995, "Cloning and functional analysis of BAG–1: A novel Bcl–2–Binding protein with anti–cell death activity", *Cell* 80:279–284.

Tanaka et al., 1993, "Sustained activation of vascular cells and leukocytes in the rabbit aorta after balloon injury", *Circulation* 88:1788–1803.

Tsujmoto et al., 1984, "Cloning of the chromosome breakpoint of neoplastic B cells with the t(14;18) chromosome translocation", *Science* 226:1097–1099.

Wang et al., 1981, "Selenium and myocardial infarction: Glutathione peroxidase in platelets", *Klin. Wochenschr.* 59:817–818.

Wilson et al., 1994, "2.2 Mb of contiguous nucleotide ssequence from chromosome III of *C. elegans", Nature* 368:32–38.

Xu et al., 1994, "Molecular cloning and functional expression of the bumetanide–sensitive Na–K–Cl cotransporter", *Proc. Natl. Acad. Sci. USA* 91:2201–2205.

Yoshimura et al., 1994, "The human plasma glutathione peroxidase–encoding gene: organization, sequence and localization to chromosome 5q32", *Gene* 145:293–297.

Grainger et al., 1993, "Proliferation of human smooth muscle cells promoted by lipoprotein(a)", *Science* 260:1655–1658.

Puolakkainen et al., 1993, "Serological response to *Chlamydia pneumoniae* in adults with coronary arterial fatty streaks and fibrolipid plaques", *J. of Clinical Microbiol.* 31:2212–2214.

Written Opinion, Related PCT Application No. PCT/US96/01883.

Hochman et al., 1995, "Dissociation of Synchronization and Excitability in Furosemide Blockade of Epileptiform Activity", *Science* 270:99–102.

Grainger et al., 1995, "Tamoxifen elevates transforming growth factor–beta and suppresses diet–induced formation of lipid lesions in mouse aorta", *Nature Medicine* 1:1067–1073.

Gura, 1995, "Estrogen: key player in heart disease among women", *Science* 269:771–773.

Farrow et al., 1995, "Cloning of bcl–2 homologue by interaction with adenovirus E1B 19K", *Nature* 374:731–733.

Kanai et al., 1995, "Identification and characterization of a prostaglandin transporter", *Science* 268:866–869.

Luscinskas et al., 1989, "Endothelial–Leukocyte adhesion molecule–1–dependent and leukocyte (CD11/CD18)–dependent mechanisms contribute to polymorphonuclear leukocyte adhesion to cytokine–activated human vascular endothelium", *J. Immunol.* 142:2257–2263.

Sekelsky et al., 1995, "Genetic characterization and cloning of mothers against dpp, a gene required for decapentaplegic function in *Drosophila melanogaster", Genetics* 139:1347–1358.

Papadaki et al. (Biotechnol. Prog., 13:209–221, 1997).

Ngo et al., in *The Protein Folding Problem and Tertiary Structure Prediction*, 1994, Merz et al., (ed.), Birkhauser, Boston, MA, pp. 433 and 492–495.

Catalogue of Cell line & Hybridomas, 7th Edition, 1992, page v.
The WashU–Merck EST Project (published Jun. 27, 1995, AN: H12679, Gene Bank).
Wallace et al, Methods in Enzymology (1987), 152:432.
Sambrook et al, Molecular Cloning, 1989, CSH:11.47.
Ledley. Hum. Gene Ther. 1995, 6:1129–1144.
Coghlan, New Scientist, Nov. 1995, vol. 148, pp. 14–15.
Marshall, Science, Aug. 1995:1053, vol. 270.

```
GGCTTAGATG CAGCCTGCAA ATTAAACTTT GATTTTTCAT CTTGTGAAAG CAGTCCTTGT   60
TCCTATGGCC TAATGAACAA CTTCCAGGTA ATGAGTATGG TGTCAGGATT TACACCACTA  120
ATTTCTGCAG GTATATTTTC AGCCACTCTT TCTTCAGCAT TAGCATCCCT AGTGAGTGCT  180
CCCAAAATAT TTCAGGCTCT ATGTAAGGAC AACATCTACC CAGCTTTCCA GATGTTTGCT  240
AAAGGTTATG GGAAAAATAA TGAACCTCTT CGTGGCTGCA TCTAAGCC               288
```

FIG. 8

```
AAAAATAAAT AAATTAAAGT CTGAGACCAA TTTGCCACTG TGAATATAAG CACATTAACC    60
CCAGGAGGAG CCAAGAACTA CACAAACCTC TCTATGAGAA TTTACCAGTC TTCTTTCATT   120
TGGCAAGAAA AAGCTCAGGA AAATTTGCTT GTTTAAATTC TATGAGCCTA GTCTATGG     178
```

FIG. 12

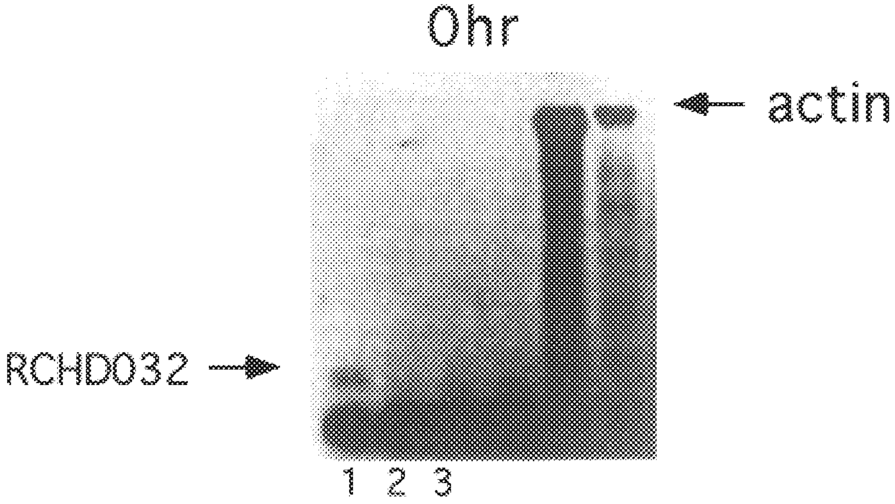
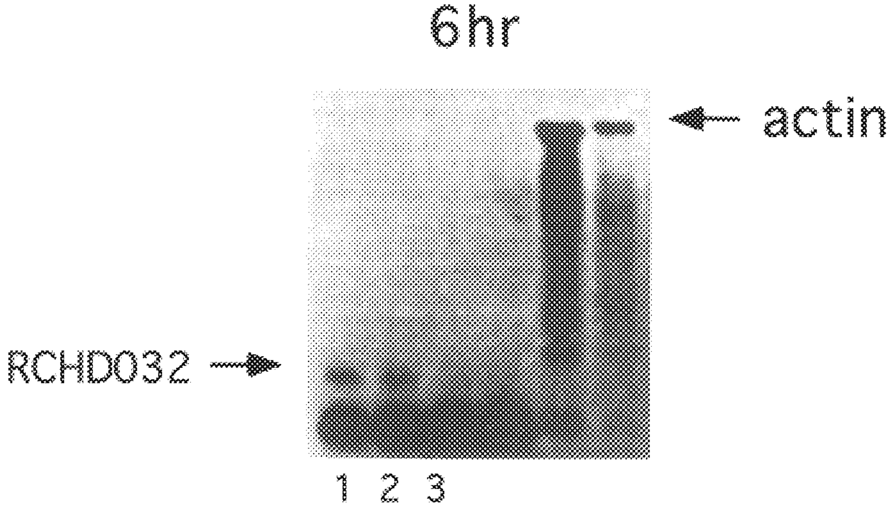
FIG. 14

```
GGGTAATTCA TTAATTACAC TTTAAAATTG GAAAGTGGGA TAAGAAATCT AAAGTAAACC    60
AGCTTATCTT TGAAACAATA TTATTTTGAA ATTGGCTTTA A                       101
```

FIG. 15

```
GGCTTGGTGG TGATGCCTAC AAGAAATGTT TACATACAAA CACTCTATAC ATCTAACTCC    60
CGAAAAAGGA CCAGCTATTT CGGCAACAGA AAAAAGACAA GCATTTCAGA GGAGCGTTGC   120
TTTCCTTAAA GACCTAACTC ACTTAAGTCT TACAAACAGA AATAACAAGG AGGACAATTT   180
TCTA                                                                184
```

FIG. 18

```
M   G   L   L   P   K   L   G   A   S   Q   G   S   D   T   S   T   S   R   A      20
ATG GGG CTC CTG CCC AAG CTC GGC GCG TCC CAG GGC AGC GAC ACC TCT ACT AGC CGA GCC    60

G   R   C   A   R   S   V   F   G   N   I   K   V   F   V   L   C   Q   G   L      40
GGC CGC TGT GCC CGC TCG GTC TTC GGC AAC ATT AAG GTG TTT GTG CTC TGC CAA GGC CTC   120

L   Q   L   C   Q   L   L   Y   S   A   Y   F   K   S   S   L   T   T   I   E      60
CTG CAG CTC TGC CAA CTC CTG TAC AGC GCC TAC TTC AAG AGC AGC CTC ACC ACC ATT GAG   180

K   R   F   G   L   S   S   S   S   S   G   L   I   S   S   L   N   E   I   S      80
AAG CGC TTT GGG CTC TCC AGT TCT TCA TCG GGT CTC ATT TCC AGC TTG AAT GAG ATC AGC   240

N   A   I   L   I   I   F   V   S   Y   F   G   S   R   V   H   R   P   R   L     100
AAT GCC ATC CTC ATC ATC TTT GTC AGC TAC TTT GGC AGC CGG GTG CAC CGT CCA CGT CTG   300

I   G   I   G   G   L   F   L   A   A   G   A   F   I   L   T   L   P   H   F     120
ATT GGC ATC GGA GGT CTC TTC CTG GCT GCA GGT GCC TTC ATC CTC ACC CTC CCA CAC TTC   360

L   S   E   P   Y   Q   Y   T   L   A   S   T   G   N   N   S   R   L   Q   A     140
CTC TCC GAG CCC TAC CAG TAC ACC TTG GCC AGC ACT GGG AAC AAC AGC CGC TTG CAG GCC   420

E   L   C   Q   K   H   W   Q   D   L   P   P   S   K   C   H   S   T   T   Q     160
GAG CTC TGC CAG AAG CAT TGG CAG GAC CTG CCT CCC AGT AAG TGC CAC AGC ACC ACC CAG   480

N   P   Q   K   E   T   S   S   M   W   G   L   M   V   V   A   Q   L   L   A     180
AAC CCC CAG AAG GAG ACC AGC AGC ATG TGG GGC CTG ATG GTG GTT GCC CAG CTG CTG GCT   540
```

FIG. 22A

```
G   I   G   T   V   P   I   Q   P   F   G   I   S   Y   V   D   D   F   S   E     200
GGC ATC GGG ACA GTG CCT ATT CAG CCA TTT GGG ATC TCC TAT GTG GAT GAC TTC TCA GAG   600

P   S   N   S   P   L   Y   I   S   I   L   F   A   I   S   V   F   G   P   A     220
CCC AGC AAC TCG CCC CTG TAC ATC TCC ATC TTA TTT GCC ATC TCT GTA TTT GGA CCG GCT   660

F   G   Y   L   L   G   S   V   M   L   Q   I   F   V   D   Y   G   R   V   N     240
TTC GGG TAC CTG CTG GGC TCT GTC ATG CTG CAG ATC TTT GTG GAC TAT GGC AGG GTC AAC   720

T   A   A   V   N   L   V   P   G   D   P   R   W   I   G   A   W   W   L   G     260
ACA GCT GCA GTT AAC TTG GTC CCG GGT GAC CCC CGA TGG ATT GGA GCC TGG TGG CTA GGC   780

L   L   I   S   S   A   L   L   V   L   T   S   F   P   F   F   F   F   P   R     280
CTG CTC ATT TCT TCA GCT TTA TTG GTT CTC ACC TCT TTC CCC TTT TTT TTC TTC CCT CGA   840

A   M   P   I   G   A   K   R   A   P   A   T   A   D   E   A   R   K   L   E     300
GCA ATG CCC ATA GGA GCA AAG AGG GCT CCT GCC ACA GCA GAT GAA GCA AGG AAG TTG GAG   900

E   A   K   S   R   G   S   L   V   D   F   I   K   R   F   P   C   I   F   L     320
GAG GCC AAG TCA AGA GGC TCC CTG GTG GAT TTC ATT AAA CGG TTT CCA TGC ATC TTT CTG   960

R   L   L   M   N   S   L   F   V   L   V   V   L   A   Q   C   T   F   S   S     340
AGG CTC CTG ATG AAC TCA CTC TTC GTC CTG GTG GTC CTG GCC CAG TGC ACC TTC TCC TCC   1020
```

FIG. 22B

```
V   I   A   G   L   S   T   F   L   N   K   F   L   E   K   Q   Y   G   T   S       360
GTC ATT GCT GGC CTC TCC ACC TTC CTC AAC AAG TTC CTG GAG AAG CAG TAT GGC ACC TCA    1080

A   A   Y   A   N   F   L   I   G   A   V   N   L   P   A   A   A   L   G   M       380
GCA GCC TAT GCC AAC TTC CTC ATT GGT GCT GTG AAC CTC CCT GCT GCA GCC TTG GGG ATG    1140

L   F   G   G   I   L   M   K   R   F   V   F   S   L   Q   A   I   P   R   I       400
CTG TTT GGA GGA ATC CTC ATG AAG CGC TTT GTT TTC TCT CTA CAA GCC ATT CCC CGC ATA    1200

A   T   T   I   I   T   I   S   M   I   L   C   V   P   L   F   F   M   G   C       420
GCT ACC ACC ATC ATC ACC ATC TCC ATG ATC CTT TGT GTT CCT TTG TTC TTC ATG GGA TGC    1260

S   T   P   T   V   A   E   V   Y   P   P   S   T   S   S   S   I   H   P   Q       440
TCC ACC CCA ACT GTG GCC GAA GTC TAC CCC CCT AGC ACA TCA AGT TCT ATA CAT CCG CAG    1320

S   P   A   C   R   R   D   C   S   C   P   D   S   I   F   H   P   V   C   G       460
TCT CCT GCC TGC CGC AGG GAC TGC TCG TGC CCA GAT TCT ATC TTC CAC CCG GTC TGT GGA    1380

D   N   G   I   E   Y   L   S   P   C   H   A   G   C   S   N   I   N   M   S       480
GAC AAT GGA ATC GAG TAC CTC TCC CCT TGC CAT GCC GGC TGC AGC AAC ATC AAC ATG AGC    1440

S   A   T   S   K   Q   L   I   Y   L   N   C   S   C   V   T   G   G   S   A       500
TCT GCA ACC TCC AAG CAA CTG ATC TAT TTG AAC TGC AGC TGT GTG ACC GGG GGA TCC GCT    1500

S   A   K   T   G   S   C   P   V   P   C   A   H   F   L   L   P   A   I   F       520
TCA GCA AAG ACA GGA TCG TGC CCT GTC CCC TGT GCC CAC TTC CTG CTC CCG GCC ATC TTC    1560
```

FIG. 22C

```
 L   I   S   F   V   S   L   I   A   C   I   S   H   N   P   L   Y   M   M   V     540
CTC ATC TCC TTC GTG TCC CTG ATA GCC TGC ATC TCC CAC AAC CCC CTC TAC ATG ATG GTT   1620

 L   R   V   V   N   Q   E   E   K   S   F   A   I   G   V   Q   F   L   L   M     560
CTG CGT GTG GTG AAC CAG GAG GAA AAG TCA TTT GCC ATC GGG GTG CAG TTC TTG TTG ATG   1680

 R   L   L   A   W   L   P   S   P   A   L   Y   G   L   T   I   D   H   S   C     580
CGC TTG CTG GCC TGG CTG CCA TCT CCA GCC CTC TAT GGC CTC ACC ATT GAC CAC TCC TGC   1740

 I   R   W   N   S   L   C   L   G   R   R   G   A   C   A   Y   Y   D   N   D     600
ATC CGG TGG AAC TCG CTG TGC TTG GGG AGG CGA GGG GCC TGC GCC TAC TAT GAC AAC GAT   1800

 A   L   R   D   R   Y   L   G   L   Q   M   G   Y   K   A   L   G   M   L   L     620
GCT CTC CGA GAC AGG TAC CTG GGC CTG CAG ATG GGC TAC AAG GCG CTG GGC ATG CTG CTG   1860

 L   C   F   I   S   W   R   V   K   K   N   K   E   Y   N   V   Q   K   A   A     640
CTT TGC TTC ATC AGC TGG AGG GTG AAG AAG AAC AAG GAG TAC AAC GTG CAG AAG GCG GCA   1920

 G   L   I   *                                                                     643
GGC CTC ATC TGA                                                                   1929

CCCCACCCTGGGCCACTGYCCTGCTCCAGAGAGTGGACCTTGACTCYTCCACACCTGCCTATACTCACTAATGTTAACA

CGTCATTTCCTKTTTGTATTTTTAAAMAAGA
```

FIG. 22D

```
GGCTTACCATCGATGCGGCCGCGGATCCAGGGCTCAGAGGGAGGACGCACCCGCCAGCCA    60
GCCGGGAACCTTCCCTCGCGGGCTCCCAGGGCGGGTCTCTTCCTCTCTCTAGCCCTGCTC   120
AGGCATTCGGCAGGTCCAGCAGAGGTACACCTCCTGCAGCGGGTTCCAAGTGCACCTCCA   180
GCCTGATGGACCTGACCAAGGAGGCTTCCAGGAGCACAGAAGGGGCTGCAACCCAGGTAC   240
CCAGAGAGTGAGCAGCTCCACGCGGACTGTGCACGGTGGCCGACACCCGCAGGGACGCC   300
CACCGGACGAGCACGCGGAGGGCCCTCGCCTCCACGGATGCACCATGCCGGTGTGAGGAG   360
CATCTGTTCTTCCCACTCTCTGCAGTTAACAAACCCAACCCAAACCACCACAGGTGCTCC   420
TCCTGGGGAGTTTCCTGTCTGACAAATGCCAGGCTCACTTCAAGGAGAATCACGCTTCTT   480
TCTAAAGATGGATTCACCATTTAAAACAGAGCTCTGGGAGCCTTTCGGCAAATCTTGAAA   540

                                  MetAspValThrSerGlnAlaArgGlyValGlyLeuGluMet    14
GCTGCACGGCGCAGAGACATGGATGTGACTTCCCAAGCCCGGGGCGTAGGCCTGGAGATG   600

TyrProGlyThrAlaGlnProAlaAlaProAsnThrThrSerProGluLeuAsnLeuSer    34
TACCCAGGCACCGCGCAGCCTGCGGCCCCCAACACCACCTCCCCCGAGCTCAACCTGTCC   660

HisProLeuLeuGlyThrAlaLeuAlaAsnGlyThrGlyGluLeuSerGluHisGlnGln    54
CACCCGCTCCTGGGCACCGCCCTGGCCAATGGGACAGGTGAGCTCTCGGAGCACCAGCAA   720

TyrValIleGlyLeuPheLeuSerCysLeuTyrThrIlePheLeuPheProIleGlyPhe    74
TACGTGATCGGCCTGTTCCTCTCGTGCCTCTACACCATCTTCCTCTTCCCCATCGGCTTT   780

ValGlyAsnIleLeuIleLeuValValAsnIleSerPheArgGluLysMetThrIlePro    94
GTGGGCAACATCCTGATCCTGGTGGTGAACATCAGCTTCCGCGAGAAGATGACCATCCCC   840
```

FIG. 27A

```
AspLeuTyrPheIleAsnLeuAlaValAlaAspLeuIleLeuValAlaAspSerLeuIle     114
GACCTGTACTTCATCAACCTGGCGGTGGCGGACCTCATCCTGGTGGCCGACTCCCTCATT     900

GluValPheAsnLeuHisGluArgTyrTyrAspIleAlaValLeuCysThrPheMetSer     134
GAGGTGTTCAACCTGCACGAGCGGTACTACGACATCGCCGTCCTGTGCACCTTCATGTCG     960

LeuPheLeuArgValAsnMetTyrSerSerValPhePheLeuThrTrpMetSerPheAsp     154
CTCTTCCTGCGGGTCAACATGTACAGCAGCGTCTTCTTCCTCACCTGGATGAGCTTCGAC    1020

ArgTyrIleAlaLeuAlaArgAlaMetArgCysSerLeuPheArgThrLysHisHisAla     174
CGCTACATCGCCCTGGCCAGGGCCATGCGCTGCAGCCTGTTCCGCACCAAGCACCACGCC    1080

ArgLeuSerCysGlyLeuIleTrpMetAlaSerValSerAlaThrLeuValProPheThr     194
CGGCTGAGCTGTGGCCTCATCTGGATGGCATCCGTGTCAGCCACGCTGGTGCCCTTCACC    1140

AlaValHisLeuGlnHisThrAspGluAlaCysPheCysPheAlaAspValArgGluVal     214
GCCGTGCACCTGCAGCACACCGACGAGGCCTGCTTCTGTTTCGCGGATGTCCGGGAGGTG    1200

GlnTrpLeuGluValThrLeuGlyPheIleValProPheAlaIleIleGlyLeuCysTyr     234
CAGTGGCTCGAGGTCACGCTGGGCTTCATCGTGCCCTTCGCCATCATCGGCCTGTGCTAC    1260
```

FIG. 27B

```
SerLeuIleValArgValLeuValArgAlaHisArgHisArgGlyLeuArgProArgArg     254
TCCCTCATTGTCCGGGTGCTGGTCAGGGCGCACCGGCACCGTGGGCTGCGGCCCCGGCGG    1320

GlnLysAlaLeuArgMetIleLeuAlaValValLeuValPhePheValCysTrpLeuPro     274
CAGAAGGCGCTCCGCATGATCCTCGCAGTGGTGCTGGTCTTCTTCGTCTGCTGGCTGCCG    1380

GluAsnValPheIleSerValHisLeuLeuGlnArgThrGlnProGlyAlaAlaProCys     294
GAGAACGTCTTCATCAGCGTGCACCTCCTGCAGCGGACGCAGCCTGGGGCCGCTCCTTGC    1440

LysGlnSerPheArgHisAlaHisProLeuThrGlyHisIleValAsnLeuAlaAlaPhe     314
AAGCAGTCTTTCCGCCATGCCCACCCCCTCACGGGCCACATTGTCAACCTCGCCGCCTTC    1500

SerAsnSerCysLeuAsnProLeuIleTyrSerPheLeuGlyGluThrPheArgAspLys     334
TCCAACAGCTGCCTAAACCCCCTCATCTACAGCTTTCTCGGGGAGACCTTCAGGGACAAG    1560

LeuArgLeuTyrIleGluGlnLysThrAsnLeuProAlaLeuAspArgPheCysHisAla     354
CTGAGGCTGTACATTGAGCAGAAAACAAATTTGCCGGCCCTGGACCGCTTCTGTCACGCT    1620

AlaLeuLysAlaValIleProAspSerThrGluGlnSerAspValArgPheSerSerAla     374
GCCCTGAAGGCCGTCATTCCAGACAGCACCGAGCAGTCGGATGTGAGGTTCAGCAGTGCC    1680

Val *                                                            375
GTGTAGACAGCCTTGGCCGCATAGGCCCAGCCAGGGTGTGACTCGGGAGCTGCACACACC    1740
```

FIG. 27C

TGGGTGGACACAAGGCACGGCCACGTCATGTCTCTAAACTGCGGTCAGATGTGGCTTCTG 1800
GCTCCTCGGGCCTCGCGAGGGTCACGCTTGCCTGGTCACCCTGGGGCTGCTTAGGAAACC 1860
TCAGGACTGGTCACCTTGCACTCCTCACACAGAATTGCTACAATCCCAAAGCGCTCGCCC 1920
CGCAGGGTCCAAAGGCCAGCGGTGACCAGCCTGTCACCCAGCTCCTCCCCGCCAACCCTG 1980
CCTGCCGCTGCACCTGCCCGCTGCTGCAGGAAACATTTCTGACACCGTCGACCAGGAAAG 2040
CCACACGGAGAGGCCACTGTGGGTGAAGCGCCTCAGTTACACAGGAACCCTAAAGCAAAT 2100
CTGCCACCGTGGGGGAACTGACGCTGGAGATGCAAGGTGCTGGTGGGTCTGAGCTGGACG 2160
TCGCGGTGTGTCCTCTGTGCCCACGGTCTGAGCTAGCTAGCGCACCGCCGAGTTAAAGAG 2220
GAGAAGGAAAACATGCTGCTCTGGTGCACGCCTGAGCGTCCTCCATCTTCCAGGATGGCA 2280
GCAATGGCGCTGTGCGGCCTCACCAGGCCCACGAGGAGCAGCAGCGCTCGGCCCGGAGCA 2340
GCAGGAAGGCCCCTCTGTGGAGCGCCCGCCGTCTGCTCCGGGGTGGTTCAGTCACTGCTT 2400
GTTGACATCAACATGGCAATTGCACTCATGTGGACTGGGACCGTGCGAGCTGCCGTGTGG 2460
GTTAGTCGGGTGCCAGGACAATGAAATACTCCAGCACCTGTGGCTGACGAATTCGTTTCT 2520
ACAGAAGTAACAGCTGGGGACAACTGCGATGATGATGTAAAAACCTTCCCATAAAATAAG 2580
CC 2582

FIG. 27D

```
                  M   A   S   P   R   A   S   R   W   P   P   P   L   L          14
CGGGCCCGCGCCGTCACC ATG GCC TCG CCG CGC GCC TCG CGG TGG CCG CCG CCG CTC CTG       42

 L   L   L   L   P   L   L   L   L   P   P   A   A   P   G   T   R   D   P   P   34
CTG CTG TTG CTG CCG CTG CTG CTG CTG CCG CCG GCG GCC CCC GGG ACG CGG GAC CCG CCG 102

 P   S   P   A   R   R   A   L   S   L   A   P   L   A   G   A   G   L   E   L   54
CCT TCC CCG GCT CGC CGC GCG CTG AGC CTG GCG CCC CTC GCG GGA GCG GGG CTG GAG CTG 162

 Q   L   E   R   R   P   E   R   E   P   P   P   T   P   P   R   E   R   R   G   74
CAG CTG GAG CGC CGC CCG GAG CGC GAG CCG CCG CCC ACG CCG CCC CGG GAG CGC CGC GGG 222

 P   A   T   P   G   P   S   Y   R   A   P   E   P   G   A   A   T   Q   R   G   94
CCC GCG ACC CCC GGC CCC AGC TAC AGG GCC CCT GAG CCA GGC GCC GCG ACA CAG CGG GGA 282

 P   S   G   R   A   P   R   G   G   S   A   D   A   A   W   K   H   W   P   E  114
CCC TCC GGC CGG GCC CCC AGA GGC GGG AGC GCG GAT GCT GCC TGG AAA CAT TGG CCA GAA 342

 S   N   T   E   A   H   V   E   N   I   T   F   Y   Q   N   Q   E   D   F   S  134
AGT AAC ACT GAG GCC CAT GTA GAA AAC ATC ACC TTC TAT CAG AAT CAA GAG GAC TTT TCA 402

 T   V   S   S   K   E   G   V   M   V   Q   T   S   G   K   S   H   A   A   S  154
ACA GTG TCC TCC AAA GAG GGT GTG ATG GTT CAG ACC TCT GGG AAG AGC CAT GCT GCT TCG 462

 D   A   P   E   N   L   T   L   L   A   E   T   A   D   A   R   G   R   S   G  174
GAT GCT CCA GAA AAC CTC ACT CTA CTC GCT GAA ACA GCA GAT GCT AGA GGA AGG AGC GGC 522
```

FIG.30A

S S S R T N F T I L P V G Y S L E I A T 194
TCT TCA AGT AGA ACA AAC TTC ACC ATT TTG CCT GTT GGG TAC TCA CTG GAG ATA GCA ACA 582

A L T S Q S G N L A S E S L H L P S S S 214
GCT CTG ACT TCC CAG AGT GGC AAC TTA GCC TCG GAA AGT CTT CAC CTG CCA TCC AGC AGT 642

S E F D E R I A A F Q T K S G T A S E M 234
TCA GAG TTC GAT GAA AGA ATT GCC GCT TTT CAA ACA AAG AGT GGA ACA GCC TCG GAG ATG 702

G T E R A M G L S E E W T V H S Q E A T 254
GGA ACA GAG AGG GCG ATG GGG CTG TCA GAA GAA TGG ACT GTG CAC AGC CAA GAG GCC ACC 762

T S A W S P S F L P A L E M G E L T T P 274
ACT TCG GCT TGG AGC CCG TCC TTT CTT CCT GCT TTG GAG ATG GGA GAG CTG ACC ACG CCT 822

S R K R N S S G P D L S W L H F Y R T A 294
TCT AGG AAG AGA AAT TCC TCA GGA CCA GAT CTC TCC TGG CTG CAT TTC TAC AGG ACA GCA 882

A S S P L L D L S S P S E S T E K L N N 314
GCT TCC TCT CCT CTC TTA GAC CTT TCC TCA CCT TCT GAA AGT ACA GAG AAG CTT AAC AAC 942

S T G L Q S S S V S Q T K T M H V A T V 334
TCC ACT GGC CTC CAG AGC TCC TCA GTC AGT CAA ACA AAG ACA ATG CAT GTT GCT ACC GTG 1002

F T D G G P R T L R S L T V S L G P V S 354
TTC ACT GAT GGT GGC CCG AGA ACG CTG CGA TCT TTG ACG GTC AGT CTG GGA CCT GTG AGC 1062

FIG.30B

```
 K   T   E   G   F   P   K   D   S   R   I   A   T   T   S   S   S   V   L   L    374
AAG ACA GAA GGC TTC CCC AAG GAC TCC AGA ATT GCC ACG ACT TCA TCC TCA GTC CTT CTT  1122

 S   P   S   A   V   E   S   R   R   N   S   R   V   T   G   N   P   G   D   E    394
TCA CCC TCT GCA GTG GAA TCG AGA AGA AAC AGT AGA GTA ACT GGG AAT CCA GGG GAT GAG  1182

 E   F   I   E   P   S   T   E   N   E   F   G   L   T   S   L   R   W   Q   N    414
GAA TTC ATT GAA CCA TCC ACA GAA AAT GAA TTT GGA CTT ACG TCT TTG CGT TGG CAA AAT  1242

 D   S   P   T   F   G   E   H   Q   L   A   S   S   S   E   V   Q   N   G   S    434
GAT TCC CCA ACC TTT GGA GAA CAT CAG CTT GCC AGC AGC TCT GAG GTG CAA AAT GGA AGT  1302

 P   M   S   Q   T   E   T   V   S   R   S   V   A   P   M   R   G   G   E   I    454
CCC ATG TCT CAG ACT GAG ACT GTG TCT AGG TCA GTC GCA CCC ATG AGA GGT GGA GAG ATC  1362

 T   A   H   W   L   L   T   N   S   T   T   S   A   D   V   T   G   S   S   A    474
ACT GCA CAC TGG CTC TTG ACC AAC AGC ACA ACA TCT GCA GAT GTG ACA GGA AGC TCT GCT  1422

 S   Y   P   E   G   V   N   A   S   V   L   T   Q   F   S   D   S   T   V   Q    494
TCA TAT CCT GAA GGT GTG AAT GCT TCA GTG TTG ACC CAG TTC TCA GAC TCT ACT GTA CAG  1482

 S   G   G   S   H   T   A   L   G   D   R   S   Y   S   E   S   S   S   T   S    514
TCT GGA GGA AGT CAC ACA GCA TTG GGA GAT AGG AGT TAT TCA GAG TCT TCA TCT ACA TCT  1542

 S   S   E   S   L   N   S   S   A   P   R   G   E   R   S   T   L   E   D   S    534
TCC TCG GAA AGC TTG AAT TCA TCA GCA CCA CGT GGA GAA CGT TCA ACC TTG GAA GAC AGC  1602
```

FIG.30C

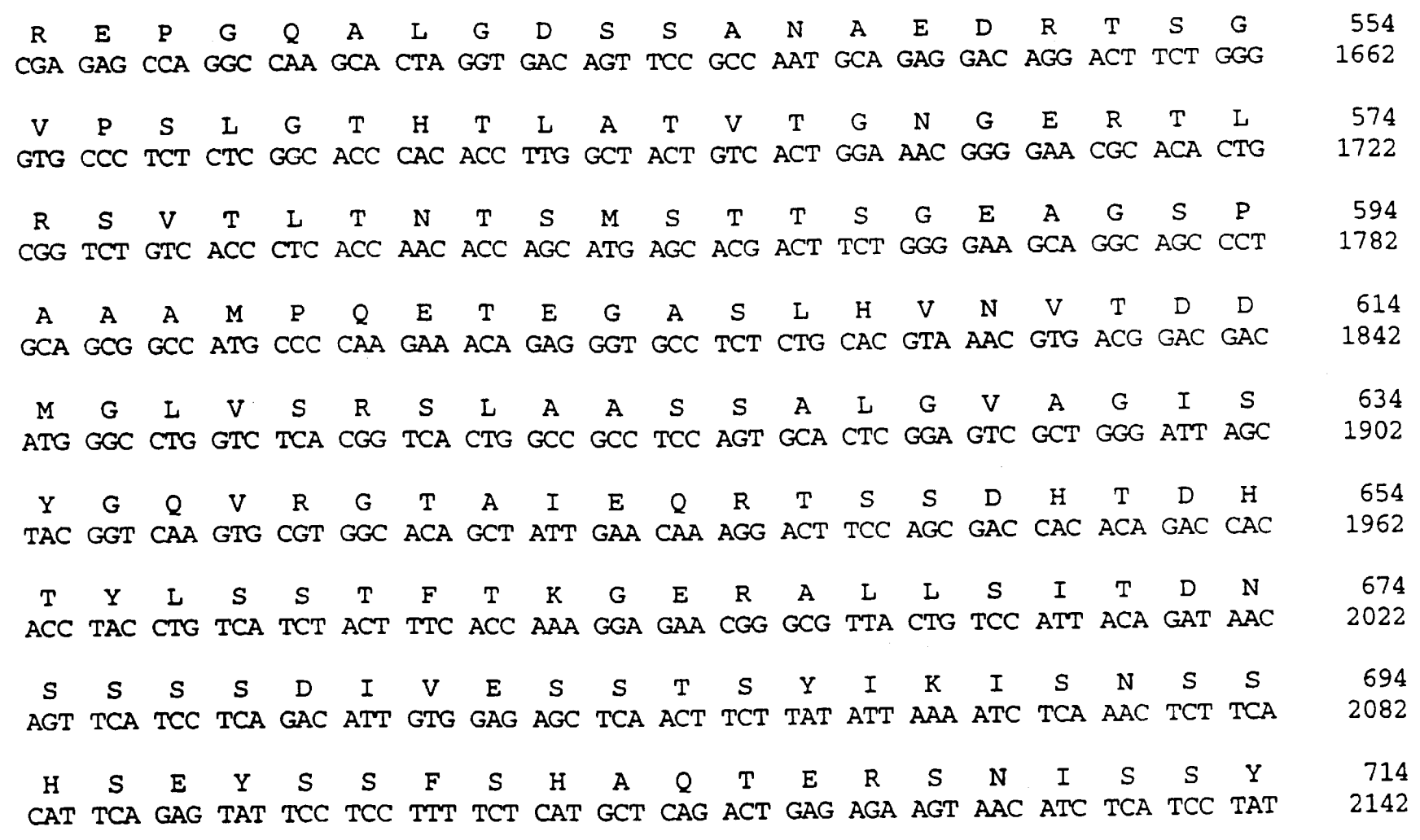

```
R   E   P   G   Q   A   L   G   D   S   S   A   N   A   E   D   R   T   S   G      554
CGA GAG CCA GGC CAA GCA CTA GGT GAC AGT TCC GCC AAT GCA GAG GAC AGG ACT TCT GGG   1662

V   P   S   L   G   T   H   T   L   A   T   V   T   G   N   G   E   R   T   L      574
GTG CCC TCT CTC GGC ACC CAC ACC TTG GCT ACT GTC ACT GGA AAC GGG GAA CGC ACA CTG   1722

R   S   V   T   L   T   N   T   S   M   S   T   T   S   G   E   A   G   S   P      594
CGG TCT GTC ACC CTC ACC AAC ACC AGC ATG AGC ACG ACT TCT GGG GAA GCA GGC AGC CCT   1782

A   A   A   M   P   Q   E   T   E   G   A   S   L   H   V   N   V   T   D   D      614
GCA GCG GCC ATG CCC CAA GAA ACA GAG GGT GCC TCT CTG CAC GTA AAC GTG ACG GAC GAC   1842

M   G   L   V   S   R   S   L   A   A   S   S   A   L   G   V   A   G   I   S      634
ATG GGC CTG GTC TCA CGG TCA CTG GCC GCC TCC AGT GCA CTC GGA GTC GCT GGG ATT AGC   1902

Y   G   Q   V   R   G   T   A   I   E   Q   R   T   S   S   D   H   T   D   H      654
TAC GGT CAA GTG CGT GGC ACA GCT ATT GAA CAA AGG ACT TCC AGC GAC CAC ACA GAC CAC   1962

T   Y   L   S   S   T   F   T   K   G   E   R   A   L   L   S   I   T   D   N      674
ACC TAC CTG TCA TCT ACT TTC ACC AAA GGA GAA CGG GCG TTA CTG TCC ATT ACA GAT AAC   2022

S   S   S   S   D   I   V   E   S   S   T   S   Y   I   K   I   S   N   S   S      694
AGT TCA TCC TCA GAC ATT GTG GAG AGC TCA ACT TCT TAT ATT AAA ATC TCA AAC TCT TCA   2082

H   S   E   Y   S   S   F   S   H   A   Q   T   E   R   S   N   I   S   S   Y      714
CAT TCA GAG TAT TCC TCC TTT TCT CAT GCT CAG ACT GAG AGA AGT AAC ATC TCA TCC TAT   2142
```

FIG.30D

```
D   G   E   Y   A   Q   P   S   T   E   S   P   V   L   H   T   S   N   L   P     734
GAC GGG GAA TAT GCT CAG CCT TCT ACT GAG TCG CCA GTT CTG CAT ACA TCC AAC CTT CCG  2202

S   Y   T   P   T   I   N   M   P   N   T   S   V   V   L   D   T   D   A   E     754
TCC TAC ACA CCC ACC ATT AAT ATG CCG AAC ACT TCG GTT GTT CTG GAC ACT GAT GCT GAG  2262

F   V   S   D   S   S   S   S   S   S   S   S   S   S   S   S   S   S   G   P     774
TTT GTT AGT GAC TCC TCC TCC TCC TCT TCC TCC TCC TCC TCT TCT TCT TCT TCA GGG CCT  2322

P   L   P   L   P   S   V   S   Q   S   H   H   L   F   S   S   I   L   P   S     794
CCT TTG CCT CTG CCC TCT GTG TCA CAA TCC CAC CAT TTA TTT TCA TCA ATT TTA CCA TCA  2382

T   R   A   S   V   H   L   L   K   S   T   S   D   A   S   T   P   W   S   S     814
ACC AGG GCC TCT GTG CAT CTA CTA AAG TCT ACC TCT GAT GCA TCC ACA CCA TGG TCT TCC  2442

S   P   S   P   L   P   V   S   L   T   T   S   T   S   A   P   L   S   V   S     834
TCA CCA TCA CCT TTA CCA GTA TCC TTA ACG ACA TCT ACA TCT GCC CCA CTT TCT GTC TCA  2502

Q   T   T   L   P   Q   S   S   S   T   P   V   L   P   R   A   R   E   T   P     854
CAA ACA ACC TTG CCA CAG TCA TCT TCT ACC CCT GTC CTG CCC AGG GCA AGG GAG ACT CCT  2562

V   T   S   F   Q   T   S   T   M   T   S   F   M   T   M   L   H   S   S   Q     874
GTG ACT TCA TTT CAG ACA TCA ACA ATG ACA TCA TTC ATG ACA ATG CTC CAT AGT AGT CAA  2622

T   A   D   L   K   S   Q   S   T   P   H   Q   E   K   V   I   T   E   S   K     894
ACT GCA GAC CTT AAG AGC CAG AGC ACC CCA CAC CAA GAG AAA GTC ATT ACA GAA TCA AAG  2682
```

FIG.30E

```
 S   P   S   L   V   S   L   P   T   E   S   T   K   A   V   T   T   N   S   P       914
TCA CCA AGC CTG GTG TCT CTG CCC ACA GAG TCC ACC AAA GCT GTA ACA ACA AAC TCT CCT     2742

 L   P   P   S   L   T   E   S   S   T   E   Q   T   L   P   A   T   S   T   N       934
TTG CCT CCA TCC TTA ACA GAG TCC TCC ACA GAG CAA ACC CTT CCA GCC ACA AGC ACC AAC     2802

 L   A   Q   M   S   P   T   F   T   T   T   I   L   K   T   S   Q   P   L   M       954
TTA GCA CAA ATG TCT CCA ACT TTC ACA ACT ACC ATT CTG AAG ACC TCT CAG CCT CTT ATG     2862

 T   T   P   G   T   L   S   S   T   A   S   L   V   T   G   P   I   A   V   Q       974
ACC ACT CCT GGC ACC CTG TCA AGC ACA GCA TCT CTG GTC ACT GGC CCT ATA GCC GTA CAG     2922

 T   T   A   G   K   Q   L   S   L   T   H   P   E   I   L   V   P   Q   I   S       994
ACT ACA GCT GGA AAA CAG CTC TCG CTG ACC CAT CCT GAA ATA CTA GTT CCT CAA ATC TCA     2982

 T   E   G   G   I   S   T   E   R   N   R   V   I   V   D   A   T   T   G   L      1014
ACA GAA GGT GGC ATC AGC ACA GAA AGG AAC CGA GTG ATT GTG GAT GCT ACC ACT GGA TTG     3042

 I   P   L   T   S   V   P   T   S   A   K   E   M   T   T   K   L   G   V   T      1034
ATC CCT TTG ACC AGT GTA CCC ACA TCA GCA AAA GAA ATG ACC ACA AAG CTT GGC GTT ACA     3102

 A   E   Y   S   P   A   S   R   S   L   G   T   S   P   S   P   Q   T   T   V      1054
GCA GAG TAC AGC CCA GCT TCA CGT TCC CTC GGA ACA TCT CCT TCT CCC CAA ACC ACA GTT     3162

 V   S   T   A   E   D   L   A   P   K   S   A   T   F   A   V   Q   S   S   T      1074
GTT TCC ACG GCT GAA GAC TTG GCT CCC AAA TCT GCC ACC TTT GCT GTT CAG AGC AGC ACA     3222
```

FIG.30F

```
 Q   S   P   T   T   L   S   S   S   A   S   V   N   S   C   A   V   N   P   C    1094
CAG TCA CCA ACA ACA CTG TCC TCT TCA GCC TCA GTC AAC AGC TGT GCT GTG AAC CCT TGT   3282

 L   H   N   G   E   C   V   A   D   N   T   S   R   G   Y   H   C   R   C   P    1114
CTT CAC AAT GGC GAA TGC GTC GCA GAC AAC ACC AGC CGT GGC TAC CAC TGC AGG TGC CCG   3342

 P   S   W   Q   G   D   D   C   S   V   D   V   N   E   C   L   S   N   P   C    1134
CCT TCC TGG CAA GGG GAT GAT TGC AGT GTG GAT GTG AAT GAG TGC CTG TCG AAC CCC TGC   3402

 P   S   T   A   T   C   N   N   T   Q   G   S   F   I   C   K   C   P   V   G    1154
CCA TCC ACA GCC ACG TGC AAC AAT ACT CAG GGA TCC TTT ATC TGC AAA TGC CCG GTT GGG   3462

 Y   Q   L   E   K   G   I   C   N   L   V   R   T   F   V   T   E   F   K   L    1174
TAC CAG TTG GAA AAA GGG ATA TGC AAT TTG GTT AGA ACC TTC GTG ACA GAG TTT AAA TTA   3522

 K   R   T   F   L   N   T   T   V   E   K   H   S   D   L   Q   E   V   E   N    1194
AAG AGA ACT TTT CTT AAT ACA ACT GTG GAA AAA CAT TCA GAC CTA CAA GAA GTT GAA AAT   3582

 E   I   T   K   T   L   N   M   C   F   S   A   L   P   S   Y   I   R   S   T    1214
GAG ATC ACC AAA ACG TTA AAT ATG TGT TTT TCA GCG TTA CCT AGT TAC ATC CGA TCT ACA   3642

 V   H   A   S   R   E   S   N   A   V   V   I   S   L   Q   T   T   F   S   L    1234
GTT CAC GCC TCT AGG GAG TCC AAC GCG GTG GTG ATC TCA CTG CAA ACA ACC TTT TCC CTG   3702

 A   S   N   V   T   L   F   D   L   A   D   R   M   Q   K   C   V   N   S   C    1254
GCC TCC AAT GTG ACG CTA TTT GAC CTG GCT GAT AGG ATG CAG AAA TGT GTC AAC TCC TGC   3762
```

FIG.30G

```
 K   S   S   A   E   V   C   Q   L   L   G   S   Q   R   R   I   F   R   A   G     1274
AAG TCC TCT GCT GAG GTC TGC CAG CTC TTG GGA TCT CAG AGG CGG ATC TTT AGA GCG GGC    3822

 S   L   C   K   R   K   S   P   E   C   D   K   D   T   S   I   C   T   D   L     1294
AGC TTG TGC AAG CGG AAG AGT CCC GAA TGT GAC AAA GAC ACC TCC ATC TGC ACT GAC CTG    3882

 D   G   V   A   L   C   Q   C   K   S   G   Y   F   Q   F   N   K   M   D   H     1314
GAC GGC GTT GCC CTG TGC CAG TGC AAG TCG GGA TAC TTT CAG TTC AAC AAG ATG GAC CAC    3942

 S   C   R   A   C   E   D   G   Y   R   L   E   N   E   T   C   M   S   C   P     1334
TCC TGC CGA GCA TGT GAA GAT GGA TAT AGG CTT GAA AAT GAA ACC TGC ATG AGT TGC CCA    4002

 F   G   L   G   G   L   N   C   G   N   P   Y   Q   L   I   T   V   V   I   A     1354
TTT GGC CTT GGT GGT CTC AAC TGT GGA AAC CCC TAT CAG CTT ATC ACT GTG GTG ATC GCA    4062

 A   A   G   G   G   L   L   L   I   L   G   I   A   L   I   V   T   C   C   R     1374
GCC GCG GGA GGT GGG CTC CTG CTC ATC CTA GGC ATC GCA CTG ATT GTT ACC TGT TGC AGA    4122

 K   N   K   N   D   I   S   K   L   I   F   K   S   G   D   F   Q   M   S   P     1394
AAG AAT AAA AAT GAC ATA AGC AAA CTC ATC TTC AAA AGT GGA GAT TTC CAA ATG TCC CCA    4182

 Y   A   E   Y   P   K   N   P   R   S   Q   E   W   G   R   E   A   I   E   M     1414
TAT GCT GAA TAC CCC AAA AAT CCT CGC TCA CAA GAA TGG GGC CGA GAA GCT ATT GAA ATG    4242

 H   E   N   G   S   T   K   N   L   L   Q   M   T   D   V   Y   Y   S   P   T     1434
CAT GAG AAT GGA AGT ACC AAA AAC CTC CTC CAG ATG ACG GAT GTG TAC TAC TCG CCT ACA    4302
```

FIG.30H

```
 S   V   R   N   P   E   L   E   R   N   G   L   Y   P   A   Y   T   G   L   P     1454
AGT GTA AGG AAT CCA GAA CTT GAA CGA AAC GGA CTC TAC CCG GCC TAC ACT GGA CTG CCA    4362

 G   S   R   H   S   C   I   F   P   G   Q   Y   N   P   S   F   I   S   D   E     1474
GGA TCA CGG CAT TCT TGC ATT TTC CCC GGA CAG TAT AAC CCG TCT TTC ATC AGT GAT GAA    4422

 S   R   R   R   D   Y   F   *                                                     1481
AGC AGA AGA AGA GAC TAC TTT TAA  GTCCAGGAGAGAGAGGGACTCATTGCTCTGAGCCAG              4482

TCACCTGGGACCTCTGCTCAGAGGACCGCACCAGGAGGCTGCGCCCAGGATTTGTCGGGA    4542

GCCACGCTGAGTGGCAAGCAGGAAGAGGGACAGGCATGCGGGGCGTGACCACAGTGGAGG    4602

AGACAGGTGGATGTGGAACCACAGGCTGCTCATTCAGCACCTTTGTTGTTACTGTGAACG    4662

TGAATGTGGGCCAGTATCAAGAGAGTCTCTCTGAGTGACTGCACCATGGCACTGGCACCA    4722

GGGCGACTATTAGCCAGGGCAGACCACTAGACTTCAGTGCAGGGACCTGGTTTTCCCTTC    4782

GTTTGCACTTTAGTAAATTGGGTGGGAGGTTTCCTTTTGGATCTGTTTTGAGACTGTTCC    4842

AGAAAGAAGGCTTCCTTTCCCGAGACACTTCCATAGGCAGCAATTTGGTGATTCAYTTGC    4902

ASCAAAATACTGGCTTGTTAATTATTTTCCTGCCCAGCRCCTGCGTGCTAAACAACAGAT    4962

GAGGATGASCGTACCACTGAAGTCTGAAGATGTCGCCATTGAACGGACAGTGTTTTCATA    5022
```

FIG.30I

| | |
|---|---|
| TGTTTCTAGGTTGTCTTATGCTACAGTTTCCAAGCCASCCCCCACAGTGAGGAAATGTGT | 5082 |
| GAGGCACCGCACACAACTGCAATGTGTTTYTTAAGTCAAGGTGACACATGTATTTAAGAT | 5142 |
| TTTTTTTTAAAATCTCYTTGCAGTTAAATCTCACTTTYTCAAACAAGCCTGGATCAGGGC | 5202 |
| AAAACAACTTATATYTGGTTTTAGCTGGAGGCTCAGCAGGCAGATTGCAGGCAGGGGGGC | 5262 |
| ACTTTTCATCCATGAGGGCCCAGCCTGGGGCCTGGGACTCTGATCACCATTGTGGAGGCC | 5322 |
| AGAGGCAMCTGCGTATGGAGGAGAAATGTCAAACTGAACGCAGGTTTCACCACTCTAGGA | 5382 |
| AAGCAGCTTGTTGACCCCCTGCASCTGGATGTGGTTAGAGGGATGGGCTGAATAGSCAGG | 5442 |
| TTAGATTTCCTGCATCAACAGTGCTTTGGGAASCTGTGTGGATTCCTGAGGAAGAACAGG | 5502 |
| GAGCCGAGATGGAGCCACACATGAATTYGCTCACCGGCTACTGCAGCACTTTGTACCCAG | 5562 |
| AATCTCATGTCCACAAACCCCATGTAAACTTTCAACCACTCAAAGSTGTTTATTCGGCTG | 5622 |
| AAGAAATAACTTTTKTTTCTCACCCAGTCATTTGTACCTCTTCATATGGSTATGTCGCAC | 5682 |
| CCTCCAGAAACGTGGTTATACTKCCAGTCAGTGTGGGAGAACTGAAGACTTCCGGTTGGT | 5742 |
| CGAGGAACTGAGGGTTGACCTTCGGGAAGGAAGTTCCACTCATCTTATTTATTATGCCTG | 5802 |

FIG.30J

```
TGATGTGGGTCCTGCCAGGGAGACATCCAGTACTCGGTGTCTKTAATTGCCACCTGGGGA 5862
ACTGTGTTTATTGGCCTTCTTTGGGGCATCCTGGKTTCGGATGAAGTGAGGGGAATACAG 5922
AGGTAAAAGAATTGTCTCCACCCTGAAGCGGGGAGTCCCGCTTCACATTTCTGGAAATGG 5982
TGCAGCCACTGGGGACAGTTCTGCCCCGGGCATGGTTGTTTCTTCAAGGTCCTCTAAATA 6042
TAATCCCTATTCTTACATAATCCTTGGCCCTGATGGTTTTAAGCAAGAACTCCTGTGTCC 6102
MATGGTCTCCACCACTCACCATCACCCTGCTGTAGCAAGAGTCCTAGTCAGGGGAGGTGC 6162
ATTTTAGTAGTTACATTGCACTTATCCATGAGATAAATAAAAGGAGAVCTGTTTTTATCA 6222
GTGGAGGCTAACCTAAAATTTCAAAGTGTCGCCTTTTTGAAATCTTGGCCTCTCTCTCT 6282
GTAGAACCAATGCCCCTTTGTGGCTCACGGCCTCGCACCTAACTGGAGAGTTCTGAGCTC 6342
CTGCAGCTCACCTGAGCCCACAGACTAGGCTTCTTGGCTCCTTCCGC 6389
```

FIG.30K

```
GAATTCGGCACGAGGMCAGGAGCTCCTTTWCTGCGTCTCCCATCATGGGGCTTAGGGTTG    60
AGTCTTCAGGTTCTGGGGGCAGGAAGGACGGGCACTCAGGAGGCCCCCTCCCCATCCACA   120
GCCCCTCTTTGGGAGGGGGAAACTTGGCAACCCGGGAGGCATGTGGATCTTTTCCTAAG   180
CAAGATGCTGAGCTGGAAAGATGGGGGTGTAAGGTAATGTCCCAAACTGAAACTTTGCCA   240
GGCACTGGGAGAGGCTGTGAACTCTTTTCTGGCTTTAGAATTTAGGTCTAGATCCCAAAA   300
GGCTAAGTACCCCCTGGGGGCTAACCAGAGGCATGCCTGGGCTGAGCTGAACCTTCTGGT   360
GCACTGGCCCCTGGCTGACTGCTCTTCTGCAGGAAGTTGGAGGAGATTCCTGAAGTTGAT   420
TCCTCAGGCTGGATGTCCAAGGGGGTTGGAGTTTCTGATGTCTTTCTGTCTCCCTCTCTT   480
TTCTTTCTCTCCCTACCAGGTCCACTTCTTTCAGAGGGGCCTGCGGTGCTCTAAAAGTTC   540
TCCTGTTAAAGTTTAGAGCAAATTGGTTATTATTTTAAAATCAATAAAACTTTTAAAAGT   600
ACTAAGACAACTTCTAAGAGGGGAGTGGACAGAGGGCCTGGTGGCAGCTCACAGTTTCTT   660
TTCTGACCTTTGGTCTCACCCACCAAGTGTCCCACCTGAGTGCCCACCTTGCCCACCTGA   720
GGTAATGCCCTGGGGCTCCACCAGTCCAGATCCACAGGGCGCAGCCATGTGGGAGTGGCG   780
GCTGATTGTTACCCAGTAGTGTTGATAGCACATTATTCATAACAGCCAAAGAGAGGAAGC   840
AACCCAAATGTCCATTAGCTGATAAATGGATAAATGAAATATGGTACGTCCGAAGAATGG   900
AATATCATTCACCCATGAAAAAGAACGAAGTCCAGCACCAAAACGTGCTACAACATGGAT   960
GAACTTCGATGACTTTGTGCCACATGAAAGAAGAAGCCAGCCACAAAAGGCCATATATTG  1020

         MetSerArgMetGlyLysProIleGluThrGlnLysSerProProPro       16
TATGAAATGAAATGTCCAGAATGGGCAAACCCATAGAGACACAAAAATCTCCGCCACCT  1079

ProTyrSerArgLeuSerProArgAspGluTyrLysProLeuAspLeuSerAspSerThr    36
CCCTACTCTCGGCTGTCTCCTCGCGACGAGTACAAGCCACTGGATCTGTCCGATTCCACA  1139
```

FIG. 34A

```
LeuSerTyrThrGluThrGluAlaThrAsnSerLeuIleThrAlaProGlyGluPheSer      56
TTGTCTTACACTGAAACGGAGGCTACCAACTCCCTCATCACTGCTCCGGGTGAATTCTCA    1199

AspAlaSerMetSerProAspAlaThrLysProSerHisTrpCysSerValAlaTyrTrp      76
GACGCCAGCATGTCTCCGGACGCCACCAAGCCGAGCCACTGGTGCAGCGTGGCGTACTGG    1259

GluHisArgThrArgValGlyArgLeuTyrAlaValTyrAspGlnAlaValSerIlePhe      96
GAGCACCGGACGCGCGTGGGCCGCCTCTATGCGGTGTACGACCAGGCCGTCAGCATCTTC    1319

TyrAspLeuProGlnGlySerGlyPheCysLeuGlyGlnLeuAsnLeuGluGlnArgSer     116
TACGACCTACCTCAGGGCAGCGGCTTCTGCCTGGGCCAGCTCAACCTGGAGCAGCGCAGC    1379

GluSerValArgArgThrArgSerLysIleGlyPheGlyIleLeuLeuSerLysGluPro     136
GAGTCGGTGCGGCGAACGCGCAGCAAGATCGGCTTCGGCATCCTGCTCAGCAAGGAGCCC    1439

AspGlyValTrpAlaTyrAsnArgGlyGluHisProIlePheValAsnSerProThrLeu     156
GACGGCGTGTGGGCCTACAACCGCGGCGAGCACCCCATCTTCGTCAACTCCCCGACGCTG    1499
```

FIG. 34B

```
AspAlaProGlyGlyArgAlaLeuValValArgLysValProProGlyTyrSerIleLys     176
GACGCGCCCGGCGGCCGCGCCCTGGTCGTGCGCAAGGTGCCCCCCGGCTACTCCATCAAG    1559

ValPheAspPheGluArgSerGlyLeuGlnHisAlaProGluProAspAlaAlaAspGly     196
GTGTTCGACTTCGAGCGCTCGGGCCTGCAGCACGCGCCCGAGCCCGACGCCGCCGACGGC    1619

ProTyrAspProAsnSerValArgIleSerPheAlaLysGlyTrpGlyProCysTyrSer     216
CCCTACGACCCCAACAGCGTCCGCATCAGCTTCGCCAAGGGCTGGGGCCCCTGCTACTCC    1679

ArgGlnPheIleThrSerCysProCysTrpLeuGluIleLeuLeuAsnAsnProArg *      235
CGGCAGTTCATCACCTCCTGCCCCTGCTGGCTGGAGATCCTCCTCAACAACCCCAGATAGT   1740
```

FIG. 34C

```
GGCGGCCCCGGCGGGAGGGGCGGGTGGGAGGCCGCGGCCACCGCCACCTGCCGGCCTCGA   1800
GAGGGGCCGATGCCCAGAGACACAGCCCCCACGGACAAAACCCCCCAGATATCATCTACC   1860
TAGATTTAATATAAAGTTTTATATATTATATGGAAATATATATTATACTTGTAATTATGG   1920
AGTCATTTTTACAATGTAATTATTTATGTATGGTGCAATGTGTGTATATGGACAAAACAA   1980
GAAAGACGCACTTTGGCTTATAATTCTTTCAATACAGATATATTTTCTTTCTCTTCCTCC   2040
TTCCTCTTCCTTACTTTTTATATATATATATAAAGAAAATGATACAGCAGAGCTAGGTGG   2100
AAAAGCCTGGGTTTGGTGTATGGTTTTTGAGATATTAATGCCCAGACAAAAAGCTAATAC   2160
CAGTCACTCGATAATAAAGTATTCGCATTATAGTTTTTTTAAACTGTCTTCTTTTTACA   2220
AAGAGGGGCAGGTAGGGCTTCAGCGGATTTCTGACCCATCATGTACCTTGAAACTTGACC   2280
TCAGTTTTCAAGTTTTACTTTTATTGGATAAAGACAGAACAAATTGAAAAGGGAGGAAAG   2340
TCACATTTACTCTTAAGTAAACCAGAGAAAGTTCTGTTGTTCCTTCCTGCCCATGGCTAT   2400
GGGGTGTCCAGTGGATAGGGATGGCGGTGGGGAAAAGGAGAATACACTGGCCATTTATCC   2460
TGGACAAGCTCTTCCAGTCTGATGGAGGAGGTTCATGCCCTAGCCTAGAAAGGCCCAGGT   2520
CCATGACCCCCATCTTTGAGTTATGAGCAAGCTAAAAGAAGACACTATTTCTCACCATTT   2580
TGTGGAAATGGCCTGGGGAACAAAGACTGAAATGGGCCTTGAGCCCACCTGCTACCTTGC   2640
AGAGAACCATCTCGAGCCCCGTAGATCTTTTTAGGACCTCCACAGGCTATTTCCCACCCC   2700
CCAGCCAAAAATAGCTCAGAATCTGCCCATCCAGGGCTGTATTAATGATTTATGTAAAGG   2760
CAGATGGTTTATTTCTACTTTGTAAAAGGGAAAAGTTGAGGTTCTGGAAGGATAAATGAT   2820
TTGCTCATGAGACAAAATCAAGGTTAGAAGTTACATGGAATTGTAGGACCAGAGCCATAT   2880
CATTAGATCAGCTTTCTGAAGAATATTCTCMAAAAAAGAAAGTCTCCTTGGCCAGATAAC   2940
TAAGAGGAATGTTTCATTGTATATCTTTTTTCTTGGAGATTTATATTAACATATTAAGTG   3000
CTCTGAGAAGTCCTGTGTATTATCTCTTGCTGCATAATAAATTATCCCCAAACTTAAAAA   3060
AAAAAAAAAAAAAAAAACTCGAG                                        3083
```

FIG. 34D

COMPOSITIONS AND METHODS FOR THE TREATMENT AND DIAGNOSIS OF CARDIOVASCULAR USING RCHD528 AS A TARGET

This is a division of application Ser. No. 08/599,654, filed on Feb. 9, 1996. which is a continuation-in-part of co-pending application Ser. No. 08/485,573, filed Jun. 7, 1995, which is a continuation-in-part of co-pending application Ser. No. 08/386,844, filed Feb. 10, 1995, each of which is hereby incorporated by reference in its entirety.

TABLE OF CONTENTS

1. INTRODUCTION
2. BACKGROUND OF THE INVENTION
3. SUMMARY OF THE INVENTION
4. DESCRIPTION OF THE FIGURES
5. DETAILED DESCRIPTION OF THE INVENTION
   5.1. IDENTIFICATION OF DIFFERENTIALLY EXPRESSED GENES
      5.1.1. PARADIGMS FOR THE IDENTIFICATION OF DIFFERENTIALLY EXPRESSED GENES
         5.1.1.1. FOAM CELL PARADIGM—1
         5.1.1.2. FOAM CELL PARADIGM—2
         5.1.1.3. FOAM CELL PARADIGM—3
         5.1.1.4. IN VIVO MONOCYTE PARADIGM
         5.1.1.5. ENDOTHELIAL CELL—IL-1 PARADIGM
         5.1.1.6. ENDOTHELIAL CELL—SHEAR STRESS PARADIGM
      5.1.2. ANALYSIS OF PARADIGM MATERIAL
   5.2. IDENTIFICATION OF PATHWAY GENES
   5.3. CHARACTERIZATION OF DIFFERENTIALLY EXPRESSED AND PATHWAY GENES
   5.4. DIFFERENTIALLY EXPRESSED AND PATHWAY GENES
      5.4.1. DIFFERENTIALLY EXPRESSED AND PATHWAY GENE SEQUENCES
      5.4.2. DIFFERENTIALLY EXPRESSED AND PATHWAY GENE PRODUCTS
      5.4.3. DIFFERENTIALLY EXPRESSED OR PATHWAY GENE PRODUCT ANTIBODIES
      5.4.4. CELL- AND ANIMAL-BASED MODEL SYSTEMS
         5.4.4.1. ANIMAL-BASED SYSTEMS
         5.4.4.2. CELL-BASED ASSAYS
   5.5. SCREENING ASSAYS FOR COMPOUNDS THAT INTERACT WITH THE TARGET GENE PRODUCT
      5.5.1. IN VITRO SCREENING ASSAYS FOR COMPOUNDS THAT BIND TO THE TARGET GENE PRODUCT
      5.5.2. ASSAYS FOR CELLULAR OR EXTRACELLULAR PROTEINS THAT INTERACT WITH THE TARGET GENE PRODUCT
      5.5.3. ASSAYS FOR COMPOUNDS THAT INTERFERE WITH INTERACTION BETWEEN TARGET GENE PRODUCT AND OTHER COMPOUNDS
      5.5.4. ASSAYS FOR AMELIORATION OF CARDIOVASCULAR DISEASE SYMPTOMS
      5.5.5. MONITORING OF EFFECTS DURING CLINICAL TRIALS
   5.6. COMPOUNDS AND METHODS FOR TREATMENT OF CARDIOVASCULAR DISEASE
      5.6.1. COMPOUNDS THAT INHIBIT EXPRESSION, SYNTHESIS OR ACTIVITY OF MUTANT TARGET GENE ACTIVITY
         5.6.1.1. INHIBITORY ANTISENSE, RIBOZYME AND TRIPLE HELIX APPROACHES
         5.6.1.2. ANTIBODIES FOR TARGET GENE PRODUCTS
      5.6.2. METHODS FOR RESTORING OR ENHANCING TARGET GENE ACTIVITY
   5.7. PHARMACEUTICAL PREPARATIONS AND METHODS OF ADMINISTRATION
      5.7.1. EFFECTIVE DOSE
      5.7.2. FORMULATIONS AND USE
   5.8. DIAGNOSIS OF CARDIOVASCULAR DISEASE ABNORMALITIES
      5.8.1. DETECTION OF FINGERPRINT GENE NUCLEIC ACIDS
      5.8.2. DETECTION OF FINGERPRINT GENE PEPTIDES
      5.8.3. IMAGING CARDIOVASCULAR DISEASE CONDITIONS
6. EXAMPLE: IDENTIFICATION OF GENES DIFFERENTIALLY EXPRESSED IN RESPONSE TO PARADIGM A: IN VITRO FOAM CELL PARADIGM
   6.1. MATERIALS AND METHODS
      6.1.1. CELL ISOLATION AND CULTURING
      6.1.2. ANALYSIS OF PARADIGM MATERIAL
      6.1.3. CHROMOSOMAL LOCALIZATION OF TARGET GENES
7. EXAMPLE: IDENTIFICATION OF GENES DIFFERENTIALLY EXPRESSED IN RESPONSE TO PARADIGM B: IN VIVO MONOCYTES
   7.1. MATERIALS AND METHODS
      7.1.1. IN VIVO CHOLESTEROL STUDIES
      7.1.2. PRELIMINARY DETECTION SYSTEM
      7.1.3. TRANSGENIC ApoE-DEFICIENT MOUSE EXPRESSING HUMAN bcl-2
   7.2. RESULTS
8. EXAMPLE: IDENTIFICATION OF GENES DIFFERENTIALLY EXPRESSED IN RESPONSE TO PARADIGM C: IL-1 INDUCTION OF ENDOTHELIAL CELLS
   8.1. MATERIALS AND METHODS
   8.2. RESULTS
9. EXAMPLE: IDENTIFICATION OF GENES DIFFERENTIALLY EXPRESSED IN RESPONSE TO PARADIGM D: ENDOTHELIAL CELL SHEAR STRESS
   9.1. MATERIALS AND METHODS
   9.2. RESULTS
10. EXAMPLE: USE OF GENES UNDER PARADIGM A AS SURROGATE MARKERS IN CLINICAL TRIALS
   10.1. TREATMENT OF PATIENTS AND CELL ISOLATION
   10.2. ANALYSIS OF SAMPLES
11. EXAMPLE: IMAGING OF A CARDIOVASCULAR DISEASE CONDITION
   11.1. MONOCLONAL CONJUGATED ANTIBODIES
   11.2. ADMINISTRATION AND DETECTION OF IMAGING AGENTS
12. EXAMPLE: SCREENING FOR LIGANDS OF THE rchd 523 GENE PRODUCT AND ANTAGONISTS OF rchd523 GENE PRODUCT-LIGAND INTERACTION
13. POLYCLONAL ANTIBODIES TO TARGET GENE PEPTIDE SEQUENCES 14. LOCALIZATION OF NOVEL GENES BY IN SITU HYBRIDIZATION
14.1 Methods
14.2 Results
15. DEPOSIT OF MICROORGANISMS

1. INTRODUCTION

The present invention relates to methods and compositions for the treatment and diagnosis of cardiovascular disease, including, but not limited to, atherosclerosis, ischemia/reperfusion, hypertension, restenosis, and arterial inflammation. Genes which are differentially expressed in cardiovascular disease states, relative to their expression in normal, or non-cardiovascular disease states are identified. Genes are also identified via the ability of their gene products to interact with other gene products involved in cardiovascular disease. The genes identified may be used diagnostically or as targets for therapeutic intervention. In this regard, the present invention provides methods for the identification and therapeutic use of compounds in the treatment and diagnosis of cardiovascular disease. Additionally, methods are provided for the diagnostic monitoring of patients undergoing clinical evaluation for the treatment of cardiovascular disease, for monitoring the efficacy of compounds in clinical trials, and for identifying subjects who may be predisposed to cardiovascular disease.

2. BACKGROUND OF THE INVENTION

Cardiovascular disease is a major health risk throughout the industrialized world. Atherosclerosis, the most prevalent of cardiovascular diseases, is the principal cause of heart attack, stroke, and gangrene of the extremities, and thereby the principle cause of death in the United States. Atherosclerosis is a complex disease involving many cell types and molecular factors (for a detailed review, see Ross, 1993, Nature 362: 801–809). The process, in normal circumstances a protective response to insults to the endothelium and smooth muscle cells (SMCs) of the wall of the artery, consists of the formation of fibrofatty and fibrous lesions or plaques, preceded and accompanied by inflammation. The advanced lesions of atherosclerosis may occlude the artery concerned, and result from an excessive inflammatory-fibroproliferative response to numerous different forms of insult. For example, shear stresses are thought to be responsible for the frequent occurrence of atherosclerotic plaques in regions of the circulatory system where turbulent blood flow occurs, such as branch points and irregular structures.

The first observable event in the formation of an atherosclerotic plaque occurs when blood-borne monocytes adhere to the vascular endothelial layer and transmigrate through to the sub-endothelial space. Adjacent endothelial cells at the same time produce oxidized low density lipoprotein (LDL). These oxidized LDL's are then taken up in large amounts by the monocytes through scavenger receptors expressed on their surfaces. In contrast to the regulated pathway by which native LDL (nLDL) is taken up by nLDL specific receptors, the scavenger pathway of uptake is not regulated by the monocytes.

These lipid-filled monocytes are called foam cells, and are the major constituent of the fatty streak. Interactions between foam cells and the endothelial and SMCs which surround them lead to a state of chronic local inflammation which can eventually lead to smooth muscle cell proliferation and migration, and the formation of a fibrous plaque. Such plaques occlude the blood vessel concerned and thus restrict the flow of blood, resulting in ischemia.

Ischemia is a condition characterized by a lack of oxygen supply in tissues of organs due to inadequate perfusion. Such inadequate perfusion can have number of natural causes, including atherosclerotic or restenotic lesions, anemia, or stroke, to name a few. Many medical interventions, such as the interruption of the flow of blood during bypass surgery, for example, also lead to ischemia. In addition to sometimes being caused by diseased cardiovascular tissue, ischemia may sometimes affect cardiovascular tissue, such as in ischemic heart disease. Ischemia may occur in any organ, however, that is suffering a lack of oxygen supply.

The most common cause of ischemia in the heart is atherosclerotic disease of epicardial coronary arteries. By reducing the lumen of these vessels, atherosclerosis causes an absolute decrease in myocardial perfusion in the basal state or limits appropriate increases in perfusion when the demand for flow is augmented. Coronary blood flow can also be limited by arterial thrombi, spasm, and, rarely, coronary emboli, as well as by ostial narrowing due to luetic aortitis. Congenital abnormalities, such as anomalous origin of the left anterior descending coronary artery from the pulmonary artery, may cause myocardial ischemia and infarction in infancy, but this cause is very rare in adults. Myocardial ischemia can also occur if myocardial oxygen demands are abnormally increased, as in severe ventricular hypertrophy due to hypertension or aortic stenosis. The latter can be present with angina that is indistinguishable from that caused by coronary atherosclerosis. A reduction in the oxygen-carrying capacity of the blood, as in extremely severe anemia or in the presence of carboxy-hemoglobin, is a rare cause of myocardial ischemia. Not infrequently, two or more causes of ischemia will coexist, such as an increase in oxygen demand due to left ventricular hypertrophy and a reduction in oxygen supply secondary to coronary atherosclerosis.

The principal surgical approaches to the treatment of ischemic atherosclerosis are bypass grafting, endarterectomy, and percutaneous translumenal angioplasty (PCTA). The failure rate after these approaches due to restenosis, in which the occlusions recur and often become even worse, is extraordinarily high (30–50%). It appears that much of the restenosis is due to further inflammation, smooth muscle accumulation, and thrombosis.

Very recently, a modified balloon angioplasty approach was used to treat arterial restenosis in pigs by gene therapy (Ohno et al., 1994, Science 265: 781–784). A specialized catheter was used to introduce a recombinant adenovirus carrying the gene encoding thymidine kinase (tk) into the cells at the site of arterial blockage. Subsequently, the pigs were treated with ganciclovir, a nucleoside analog which is converted by tk into a toxic form which kills cells when incorporated into DNA. Treated animals had a 50% to 90% reduction in arterial wall thickening without any observed local or systemic toxicities.

Because of the presumed role of the excessive inflammatory-fibroproliferative response in atherosclerosis and ischemia, a number of researchers have investigated, in the context of arterial injury, the expression of certain factors involved in inflammation, cell recruitment and proliferation. These factors include growth factors, cytokines, and other chemicals, including lipids involved in cell recruitment and migration, cell proliferation and the control of lipid and protein synthesis.

For example, the expression of PDGF (platelet derived growth factor) or its receptor was studied: in rats during repair of arterial injury (Majesky et al., 1990, J. Cell Biol.

111: 2149); in adherent cultures of human monocyte-derived macrophages treated with oxidized LDL (Malden et al., 1991, J. Biol. Chem. 266: 13901); and in bovine aortic endothelial cells subjected to fluid shear stress (Resnick et al., 1993, Proc. Natl. Acad. Sci. USA 90: 4591–4595). Expression of IGF-I (insulin-like growth factor-I) was studied after balloon deendothelialization of rat aorta (Cercek et al., 1990, Circulation Research 66: 1755–1760).

Other studies have focused on the expression of adhesion-molecules on the surface of activated endothelial cells which mediate monocyte adhesion. These adhesion molecules include intracellular adhesion molecule-1, ICAM-1 (Simmons et al., 1988, Nature, 331: 624–627), ELAM (Bevilacqua et al., 1989, Science 243: 1160–1165; Bevilacqua et al., 1991, Cell 67: 233), and vascular cell adhesion molecule, VCAM-1 (Osborn et al., 1989, Cell 59: 1203–1211); all of these surface molecules are induced transcriptionally in the presence of IL-1. Histological studies reveal that ICAM-1, ELAM and VCAM-1 are expressed on endothelial cells in areas of lesion formation in vivo (Cybulsky et al., 1991, Science 251: 788–791; 1991, Arterioscler. Thromb. 11: 1397a; Poston et al., 1992, Am. J. Pathol. 140: 665–673). VCAM-1 and ICAM-1 were shown to be induced in cultured rabbit arterial endothelium, as well as in cultured human iliac artery endothelial cells by lysophophatidylcholine, a major phospholipid component of atherogenic lipoproteins. (Kume et al., 1992, J. Clin. Invest. 90: 1138–1144). VCAM-I, ICAM-1, and class II major histocompatibility antigens were reported to be induced in response to injury to rabbit aorta (Tanaka, et al., 1993, Circulation 88: 1788–1803).

Recently, cytomegalovirus (CMV) has been implicated in restenosis as well as atherosclerosis in general (Speir, et al., 1994, Science 265: 391–394). It was observed that the CMV protein IE84 apparently predisposes smooth muscle cells to increased growth at the site of restenosis by combining with and inactivating p53 protein, which is known to suppress tumors in its active form.

The foregoing studies are aimed at defining the role of particular gene products presumed to be involved in the excessive inflammatory-fibroproliferative response leading to atherosclerotic plaque formation. However, such approaches cannot identify the full panoply of gene products that are involved in the disease process, much less identifying those which may serve as therapeutic targets for the diagnosis and treatment of various forms of cardiovascular disease.

3. SUMMARY OF THE INVENTION

The present invention relates to methods and compositions for the treatment and diagnosis of cardiovascular disease, including but not limited to, atherosclerosis, ischemia/reperfusion, hypertension, restenosis, and arterial inflammation. Specifically, genes are identified and described which are differentially expressed in cardiovascular disease states, relative to their expression in normal, or non-cardiovascular disease states.

"Differential expression", as used herein, refers to both quantitative as well as qualitative differences in the genes' temporal and/or tissue expression patterns. Differentially expressed genes may represent "fingerprint genes," and/or "target genes." "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of cardiovascular disease. "Target gene", as used herein, refers to a differentially expressed gene involved in cardiovascular disease such that modulation of the level of target gene expression or of target gene product activity may act to ameliorate a cardiovascular disease condition. Compounds that modulate target gene expression or activity of the target gene product can be used in the treatment of cardiovascular disease.

Further, "pathway genes" are defined via the ability of their products to interact with other gene products involved in cardiovascular disease. Pathway genes may also exhibit target gene and/or fingerprint gene characteristics. Although the genes described herein may be differentially expressed with respect to cardiovascular disease, and/or their products may interact with gene products important to cardiovascular disease, the genes may also be involved in mechanisms important to additional cardiovascular processes.

The invention includes the products of such fingerprint, target, and pathway genes, as well as antibodies to such gene products. Furthermore, the engineering and use of cell- and animal-based models of cardiovascular disease to which such gene products may contribute are also described.

The present invention encompasses methods for prognostic and diagnostic evaluation of cardiovascular disease conditions, and for the identification of subjects exhibiting a predisposition to such conditions. Furthermore, the invention provides methods for evaluating the efficacy of drugs, and monitoring the progress of patients, involved in clinical trials for the treatment of cardiovascular disease.

The invention also provides methods for the identification of compounds that modulate the expression of genes or the activity of gene products involved in cardiovascular disease, as well as methods for the treatment of cardiovascular disease which may involve the administration of such compounds to individuals exhibiting cardiovascular disease symptoms or tendencies.

The invention is based, in part, on systematic search strategies involving in vivo and in vitro cardiovascular disease paradigms coupled with sensitive and high throughput gene expression assays. In contrast to approaches that merely evaluate the expression of a given gene product presumed to play a role in a disease process, the search strategies and assays used herein permit the identification of all genes, whether known or novel, that are expressed or repressed in the disease condition, as well as the evaluation of their temporal regulation and function during disease progression. This comprehensive approach and evaluation permits the discovery of novel genes and gene products, as well as the identification of an array of genes and gene products (whether novel or known) involved in novel pathways that play a major role in the disease pathology. Thus, the invention allows one to define targets useful for diagnosis, monitoring, rational drug screening and design, and/or other therapeutic intervention.

In the working examples described herein, eight novel human genes are identified that are demonstrated to be differentially expressed in different cardiovascular disease states. Additionally, the differential expression of four previously identified human genes is described. The identification of these genes and the characterization of their expression in particular disease states provide newly identified roles in cardiovascular disease for both the novel genes and the known genes.

Bcl-2 and glutathione peroxidase are the products of known genes that are shown herein to be down regulated in monocytes of patients exposed to an atherogenic high fat/ high cholesterol diet. Furthermore, counteracting the down-regulation of bcl-2 under atherogenic conditions, as described herein, may ameliorate atherosclerosis. Accordingly, methods are provided for the diagnosis, monitoring in clinical trials, and treatment of cardiovascular disease based upon the discoveries herein regarding the expression patterns of bcl-2 and glutathione peroxidase. Because these two genes were known to be involved in preventing apoptosis, the discovery of their down-regulation under atherogenic conditions provides a novel, positive correlation between apoptosis and atherogenesis. Accordingly, methods provided herein for diagnosing, monitoring, and treating cardiovascular disease may also be based on a number of genes involved in the apoptotic pathway, including but not limited to ICE (IL-1 converting enzyme); Bad; BAG-1 (Bcl-2 associated athanogene 1, Takayama et al., 1995, Cell 80: 279–284); BAX (Bcl-2 associated X protein, Oltvai et al., 1993, Cell 74: 609–619); $BclX_L$ (Boise, et al., 1993, Cell 74: 597–608); BAK (Bcl-2 antagonist killer, Farrow et al., 1995. Nature 374: 631–733); and $Bcl-X_S$ (Tsujmoto et al., 1984, Science 226: 1097–1099). The cardiovascular diseases that may be so diagnosed, monitored in clinical trials, and treated include but are not limited to atherosclerosis, ischemia/reperfusion, and restenosis.

rchd005, rchd024, rchd032, and rchd036 are newly identified genes that are each up-regulated in endothelial cells treated with IL-1. Accordingly, methods are provided for the diagnosis, monitoring in clinical trials, and treatment of cardiovascular disease based upon the discoveries herein regarding the expression patterns of rchd005, rchd024, rchd032, and rchd036.

Cyclooxygenase II (COX II), also known as endoperoxide synthase, and Manganese Superoxide Dismutase (MnSOD) are known genes, and rchd502, rchd523, rchd528, and rchd534 are newly identified genes, that are each up-regulated in endothelial cells subjected to shear stress. Accordingly, methods are provided for the diagnosis, monitoring in clinical trials, screening for therapeutically effective compounds, and treatment of cardiovascular disease based upon the discoveries herein regarding the expression patterns of COX II, MnSOD, rchd502, rchd523, rchd528, and rchd534.

More specifically, each of these genes is up-regulated either by IL-1 (rchd005, rchd024, rchd032, and rchd036) or by shear stress (COX II, MnSOD, rchd502, rchd523, rchd528, and rchd534). For those genes that have a causative effect on the disease conditions treatment methods can be designed to reduce or eliminate their expression, particularly in endothelial cells. Alternatively, treatment methods include inhibiting the activity of the protein products of these genes. For those genes that have a protective effect in responding to disease conditions, treatment methods can be designed for enhancing the activity of the products of such genes.

In either situation, detecting expression of these genes in excess of normal expression provides for the diagnosis of cardiovascular disease. Furthermore, in testing the efficacy of compounds during clinical trials, a decrease in the level of the expression of these genes corresponds to a return from a disease condition to a normal state, and thereby indicates a positive effect of the compound. The cardiovascular diseases that may be so diagnosed, monitored in clinical trials, and treated include but are not limited to atherosclerosis, ischemia/reperfusion, hypertension, restenosis, and arterial inflammation.

Membrane bound target gene products containing extracellular domains can be a particularly useful target for treatment methods as well as diagnostic and clinical monitoring methods. The rchd523 gene, for example, encodes a transmembrane protein, which contains seven transmembrane domains and, therefore, can be readily contacted by other compounds on the cell surface. Accordingly, natural ligands, derivatives of natural ligands, and antibodies that bind to the rchd523 gene product can be utilized to inhibit its activity, or alternatively, to target the specific destruction of cells that are in the disease state. Furthermore, the extracellular domains of the rchd523 gene product provide especially efficient screening systems for identifying compounds that bind to the rchd523 gene product. Compounds that bind the receptor domain of the rchd523 gene product, for example, can be identified by their ability to mobilize $Ca^{2+}$ and thereby produce a fluorescent signal, as described in Section 5.5.1, below.

Such an assay system can also be used to screen and identify antagonists of the interaction between the rchd523 gene product and ligands that bind to the rchd523 gene product. For example, the compounds can compete with the endogenous (i.e., natural) ligand for the rchd523 gene product. The resulting reduction in the amount of ligand-bound rchd523 gene transmembrane protein will modulate the activity of disease state cells, such as endothelial cells. Soluble proteins or peptides, such as peptides comprising one or more of the extracellular domains, or portions and/or analogs thereof of the rchd523 gene product, including, for example, soluble fusion proteins such as Ig-tailed fusion proteins, can be particularly useful for this purpose.

Similarly, antibodies that are specific to one or more of the extracellular domains of the rchd523 product provide for the ready detection of this target gene product in diagnostic tests or in clinical test monitoring. Accordingly, endothelial cells can be treated, either in vivo or in vitro, with such a labeled antibody to determine the disease state of endothelial cells. Because the rchd523 gene product is up-regulated in endothelial cells under shear stress, its detection positively corresponds with cardiovascular disease.

Such methods for treatment, diagnosis, and clinical test monitoring which use the rchd523 gene product as described above can also be applied to other target genes that encode transmembrane gene products, including but not limited to rchd502, which each contains 12 transmembrane domains, and rchd528, which contains one transmembrane domain in addition to its extracellular domain.

The examples presented in Sections 6–9, below, demonstrate the use of the cardiovascular disease paradigms of the invention to identify cardiovascular disease target genes.

The example presented in Section 10, below, demonstrates the use of fingerprint genes in diagnostics and as surrogate markers for testing the efficacy of candidate drugs in basic research and in clinical trials.

The example presented in Section 11, below, demonstrates the use of fingerprint genes, particularly rchd523, in the imaging of a diseased cardiovascular tissue.

The example presented in Section 12, below, demonstrates the use of target genes, particularly rchd523, in screening for ligands of target gene product receptor domains, as well as antagonists of the ligand-receptor interaction.

4. DESCRIPTION OF THE FIGURES

FIG. 1. In vivo cholesterol differential display. mRNA prepared from human monocytes isolated from the blood of patients on different diets. cDNA prepared from one patient on a high fat diet/high serum cholesterol (lanes 1,2) and low fat diet/low serum cholesterol (lanes 3,4) was displayed using the forward primer $T_{11}XG$ (SEQ ID NO:8) and the reverse primer OPO14 (agcatggctc; SEQ ID NO:9)). The DNA corresponding to marked band (#14) was excised and amplified for sequence analysis.

Figure 2:
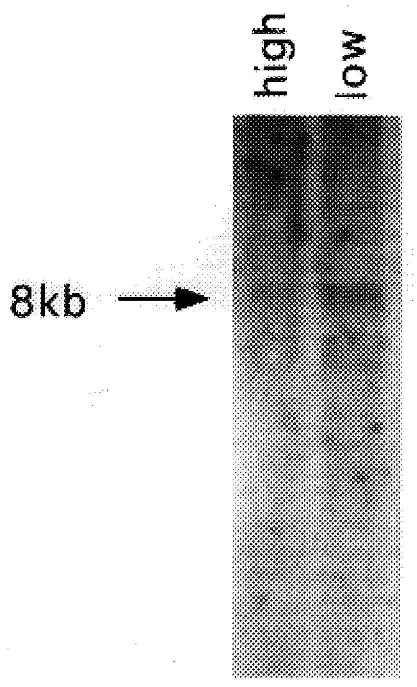

FIG. 2. Band #14 Northern blot analysis. A random primer-labeled band #14 probe was hybridized with a Northern blot prepared from the same patient's monocytes used in differential display. An 8 kb band was seen in the low fat/low cholesterol conditions, and not in the high fat/high cholesterol conditions.

Figure 3:
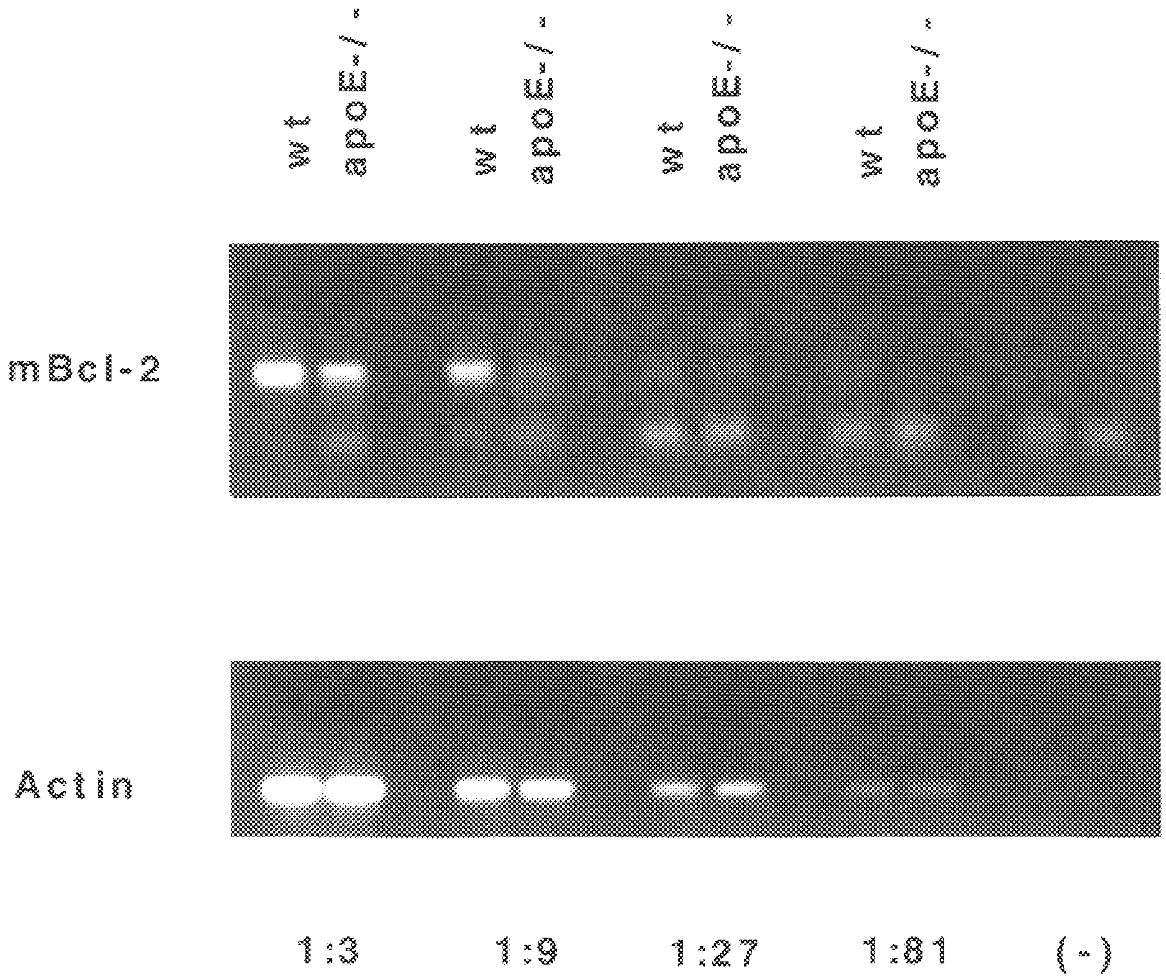

FIG. 3. Quantitative RT-PCR analysis of mouse bcl-2 mRNA levels in apoE-deficient mice. Monocyte RNA from apoE-deficient and control mice was compared using primers for mouse bcl-2 (for-cacccctggcatcttctccttcc (SEQ ID NO:10)/rev-atcctcccccagttcaccccatcc SEQ ID NO:11) shown in the upper panel and mouse γActin (for-cctgatagatgggcactgtgt (SEQ ID NO:12)/rev-gaacacggcattgtcactaact (SEQ ID NO:13)) shown in the lower panel. A 1:3 dilution series of each input cDNA was done in pairs with the left band in each pair deriving from wild-type cDNA and the right band from apoE-deficient cDNA.

Figure 4:
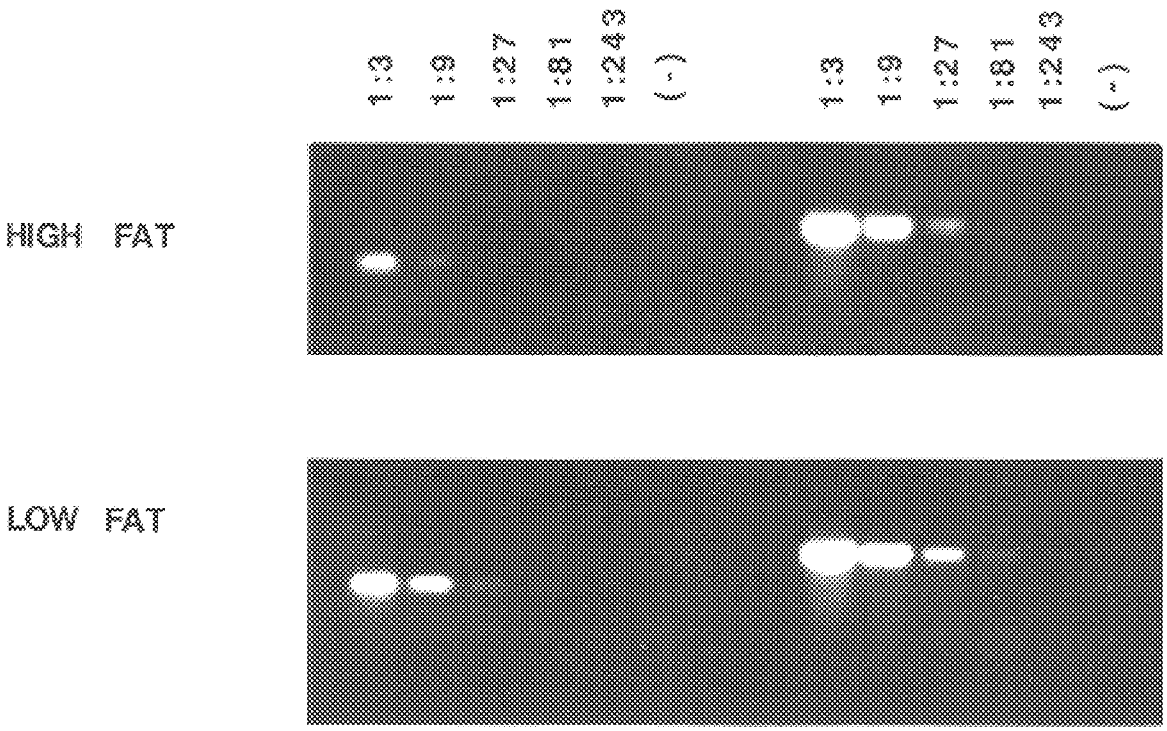

FIG. 4. RT-PCR quantification of human glutathione peroxidase (HUMGPXP1) cDNA from human clinical samples cDNA prepared from RNA derived from blood monocytes of the same patient under a high fat diet (serum cholesterol level=200; top panel) and a low fat diet (serum cholesterol level=170; bottom panel). Dilution series of amplification products using GPX1.3 primers derived from HUMGPXP1 sequences 1121–1142 (for-aagtcgcgcccgcccctgaaat SEQ ID NO:14) and 1260–1237 (rev-gatccctggccaccgtccgtctga; SEQ ID NO:15) is shown in the left portion of each panel. Dilution series of amplification products using human actin primers (for-accctgaagtacccat; SEQ ID NO:16/rev-tagaagcatttgcggtg; SEQ ID NO:17) is shown in the right portion of each panel. The HUMGPXP1 band decreased in intensity under a high fat diet (compare top left to bottom left), whereas the actin control band was equally intense under each diet (compare top right to bottom right).

Figure 5:
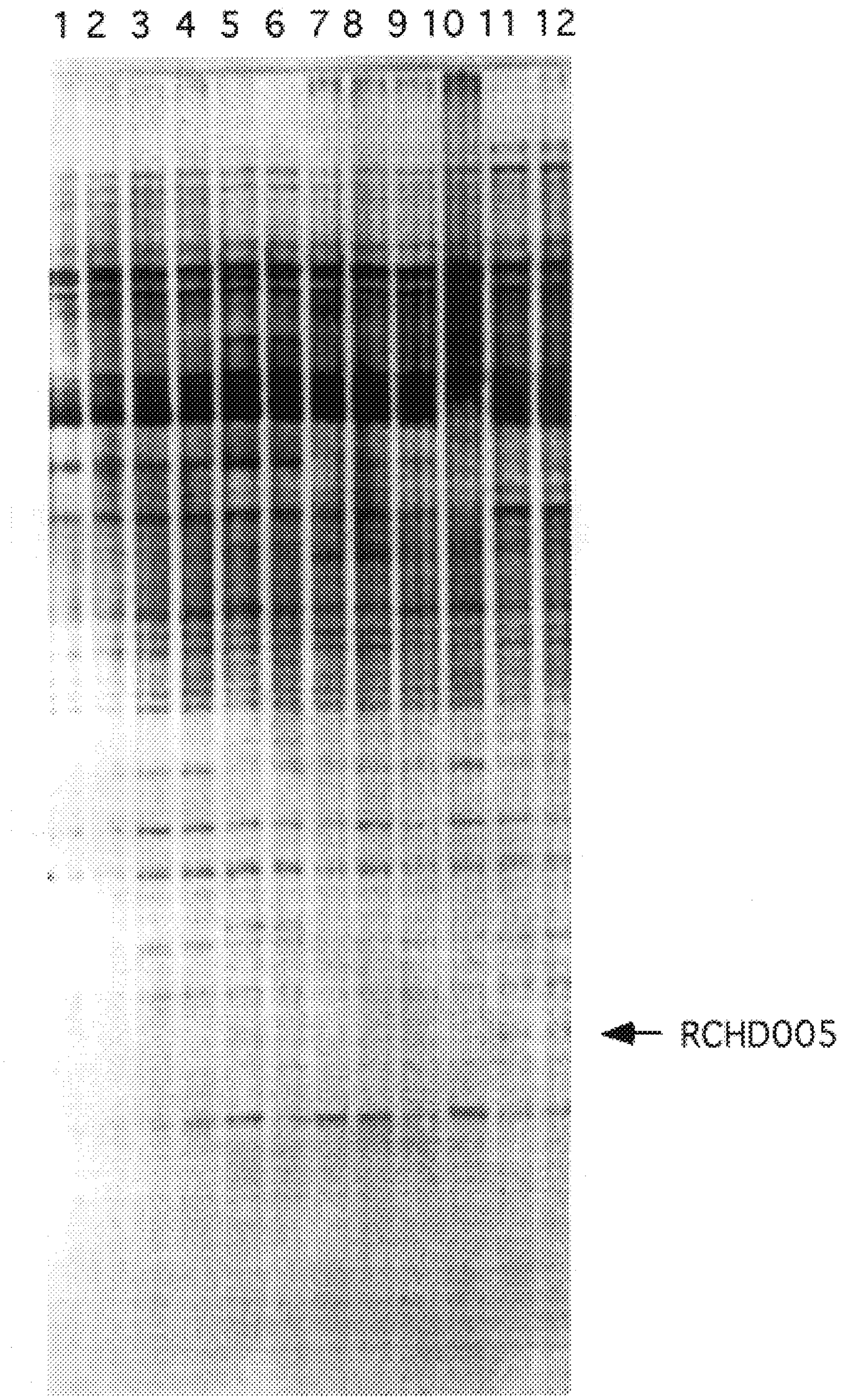

FIG. 5. IL-1 activated HUVEC differential display. mRNA prepared from control HUVEC (lanes 9,10), 1 hr. of 10 units/ml IL-1 treatment (lanes 7,8), or 6 hr. treatment (lanes 11,12), was used in differential display reactions with the forward primer OPE7 (agatgcagcc; SEQ ID NO:18) and reverse primer $T_{11}XA$ (SEQ ID NO:19), which is an equimolar mix of oligonucleotides where X is G, C, or A. The DNA corresponding to marked band, rchd005, was excised and amplified for Northern analysis and subcloning.

Figure 6:
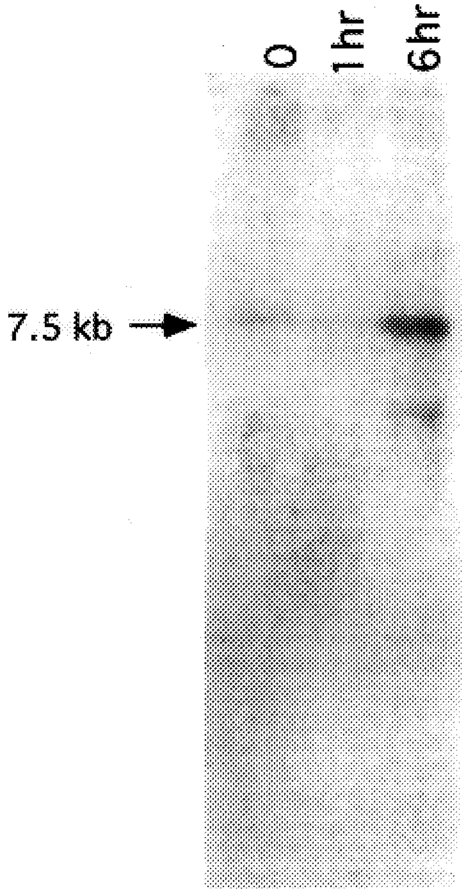

FIG. 6. Northern blot analysis of endothelial IL-1 inducible rchd005. 2 $\mu$g of total RNA from control, 1 hr. and 6 hr. samples was eluted on an agarose gel, blotted, and incubated with a $^{32}$P labeled probe prepared from amplified rchd005 sequences. The indicated band migrated with markers corresponding to approximately 7.5 kb.

Figure 7:
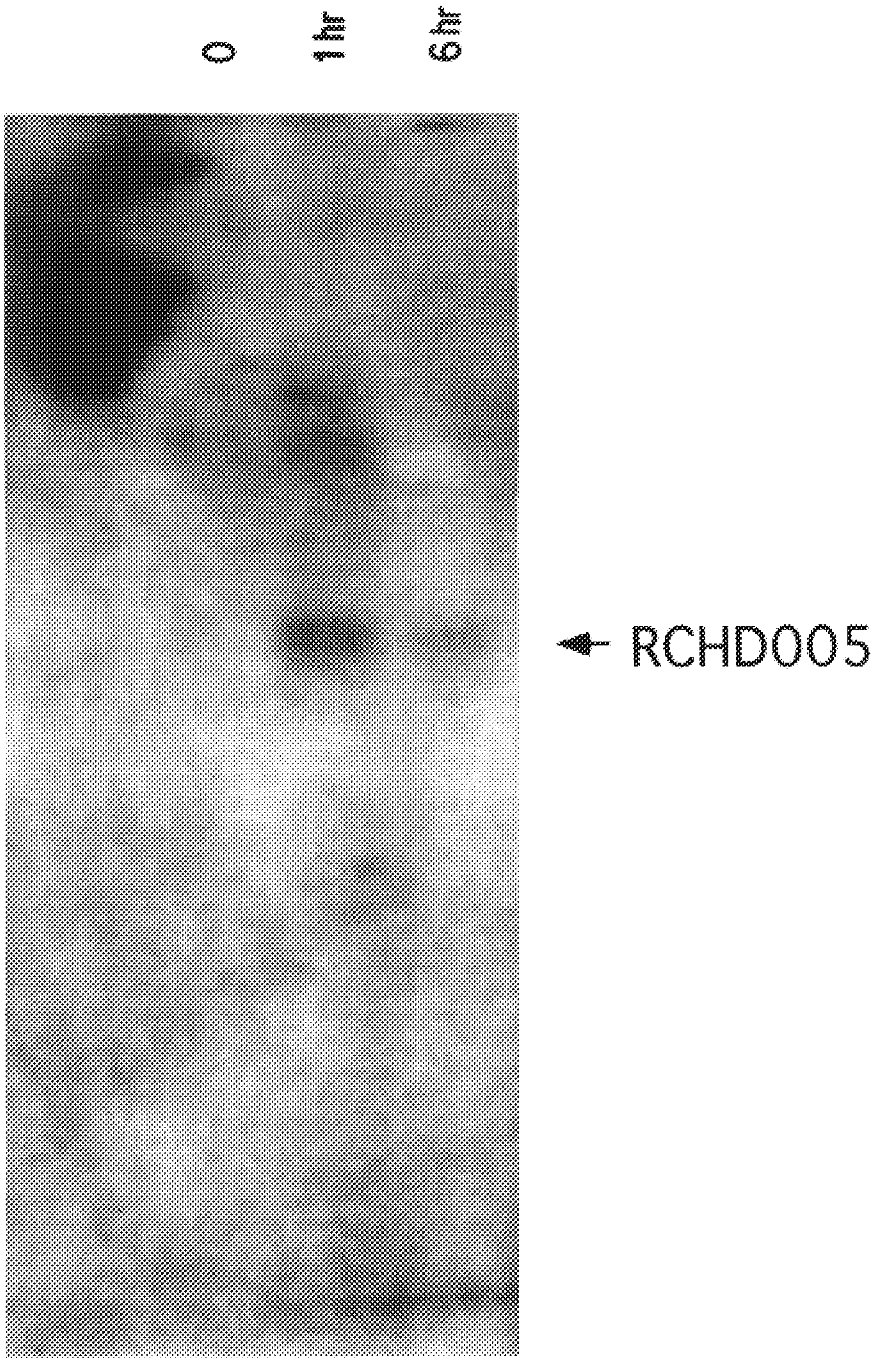

FIG. 7. A Northern blot prepared from shear stressed RNA and hybridized with the same rchd005 probe detects a 7.5 kb band up-regulated most strongly at 1 hr.

FIG. 8. Band rchd005 DNA sequence; SEQ ID NO:1. The sequence was determined by sequencing the insert of pRCHD005, resulting from the ligation of amplified rchd005 sequences into the TA cloning vector.

Figure 9:
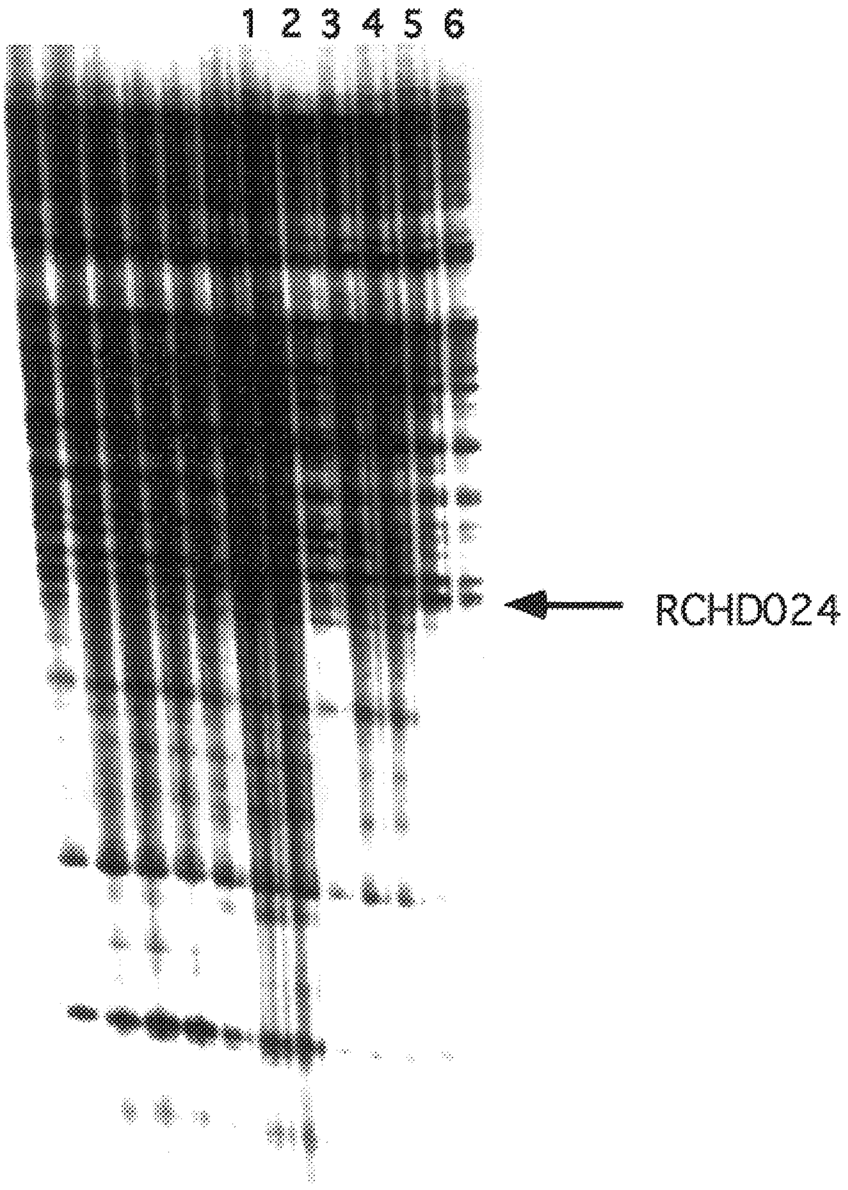

FIG. 9. IL-1 activated HUVEC differential display. mRNA prepared from control HUVEC (lanes 3,4), 1 hr. of 10 units/ml IL-1 treatment (lanes 1,2), or 6 hr. treatment (lanes 5,6), was used in differential display reactions with the forward primer OPG20 (tctccctcag; SEQ ID NO:20) and reverse primer $T_{11}XC$, (SEQ ID NO:21) which is an equimolar mix of oligonucleotides where X is G, C, or A. The DNA corresponding to marked band, rchd024, was excised and amplified for Northern analysis and subcloning.

Figure 10:
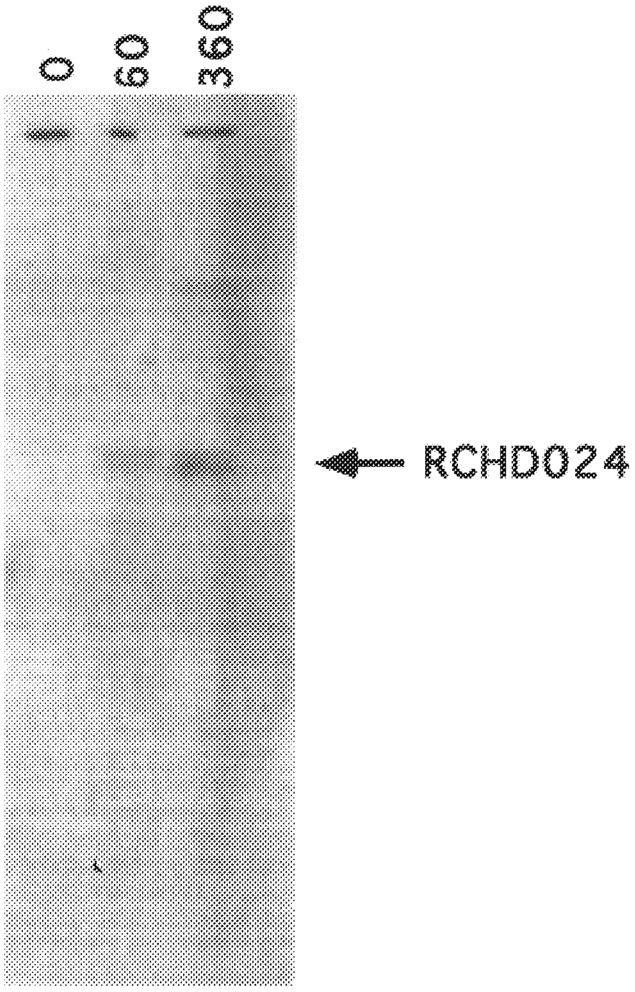

FIG. 10. Northern blot analysis of endothelial IL-1 inducible band rchd024. 2 $\mu$g of total RNA from control, 1 hr. and 6 hr. samples was eluted on an agarose gel, blotted, and incubated with a $^{32}$P labeled probe prepared from amplified band rchd024 sequences. The indicated band migrated with markers corresponding to approximately 10 kb.

Figure 11:
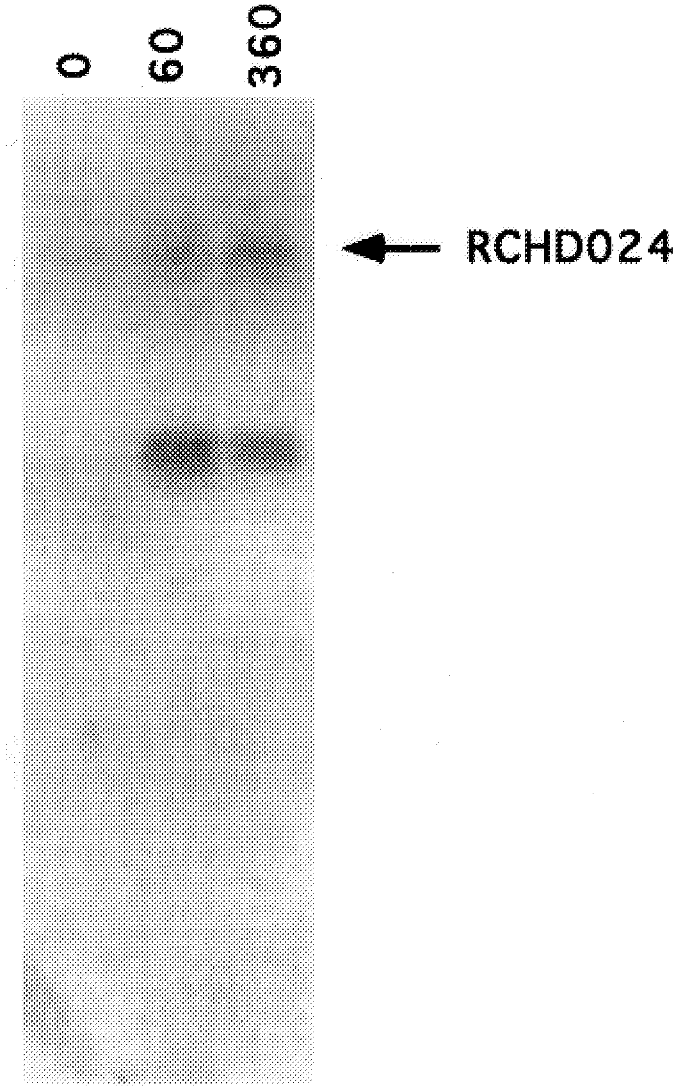

FIG. 11.Shear stress Northern blot analysis of endothelial IL-1 inducible band rchd024. A Northern blot prepared from shear stressed RNA and hybridized with the same rchd024 probe detected a 10 kb band up-regulated most strongly at 6 hr.

FIG. 12.Band rchd024 DNA sequence; SEQ ID NO:2. The sequence was determined by sequencing the insert of pRCHD024, resulting from the ligation of amplified rchd024 sequences into the TA cloning vector.

Figure 13:
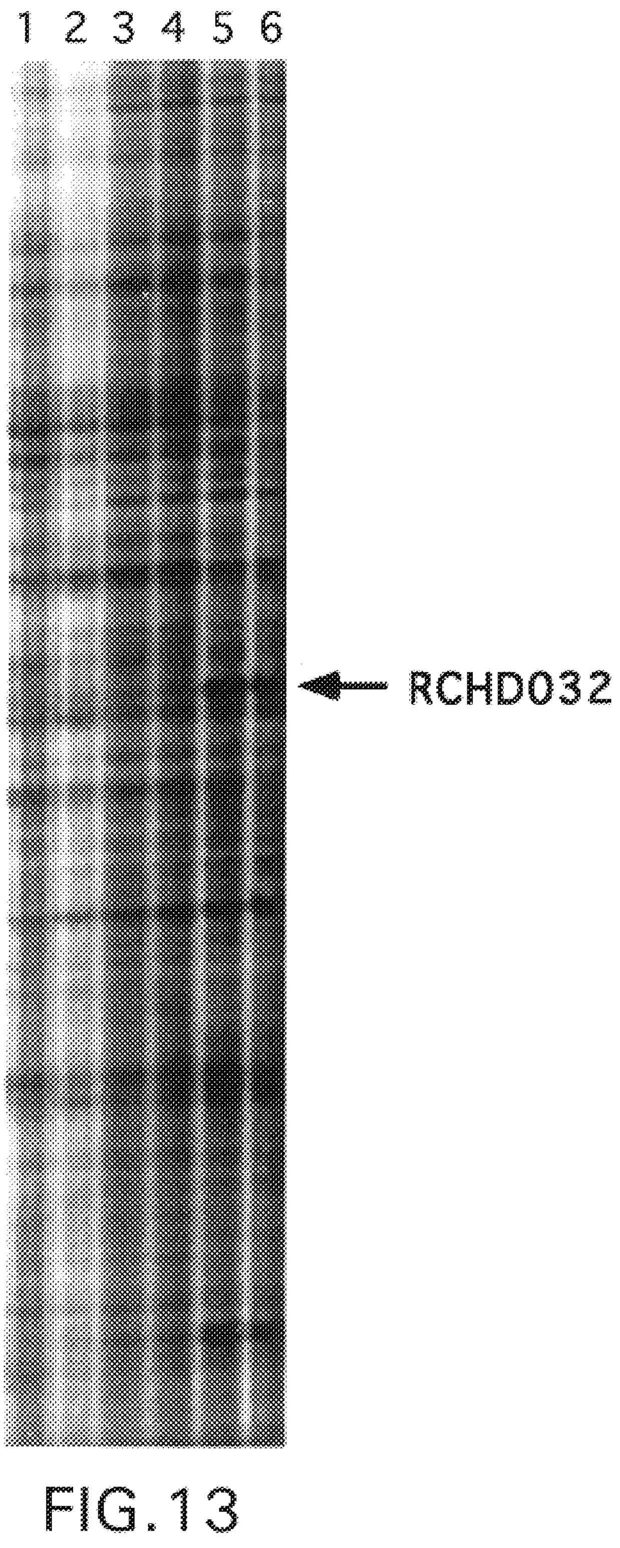

FIG. 13. IL-1 activated HUVEC differential display for rchd032. mRNA prepared from control HUVEC (lanes 3,4), 1 hr. of 10 units/ml IL-1 treatment (lanes 1,2), or 6 hr. treatment (lanes 5,6), was used in differential display reactions with the forward primer OPI9 (tggagagcag; SEQ ID NO:22) and reverse primer $T_{11}XA$, (SEQ ID NO:19) which is an equimolar mix of oligonucleotides where X is G, C, or A. The DNA corresponding to marked band, rchd032, was excised and amplified for Northern analysis and subcloning.

FIG. 14. RT-PCR quantification of rchd032 cDNA from IL-1 activated HUVEC's cDNA prepared from RNA derived from control, 1 hr., and 6 hr. IL-1 activated HUVEC's. Shown in lanes 1,2, and 3 are a 5 fold dilution series of input cDNA amplified in the upper panel with rchd032 primers (for-atttataaaggggtaattcatta (SEQ ID NO:23)/rev-ttaaagccaatttcaaaataat; SEQ ID NO:24), and in the lower panel with human actin primers (for-accctgaagtaccccat (SEQ ID NO:16)/rev-tagaagcatttgcggtg; SEQ ID NO:17). A band at the 1:125 dilution in lane 3 is visible in the 6 hr. sample but not in the control.

FIG. 15. Band rchd032 DNA sequence; SEQ ID NO:3. The sequence was determined by sequencing the insert of pRCHD032, resulting from the ligation of amplified rchd032 sequences into the TA cloning vector.

Figure 16:
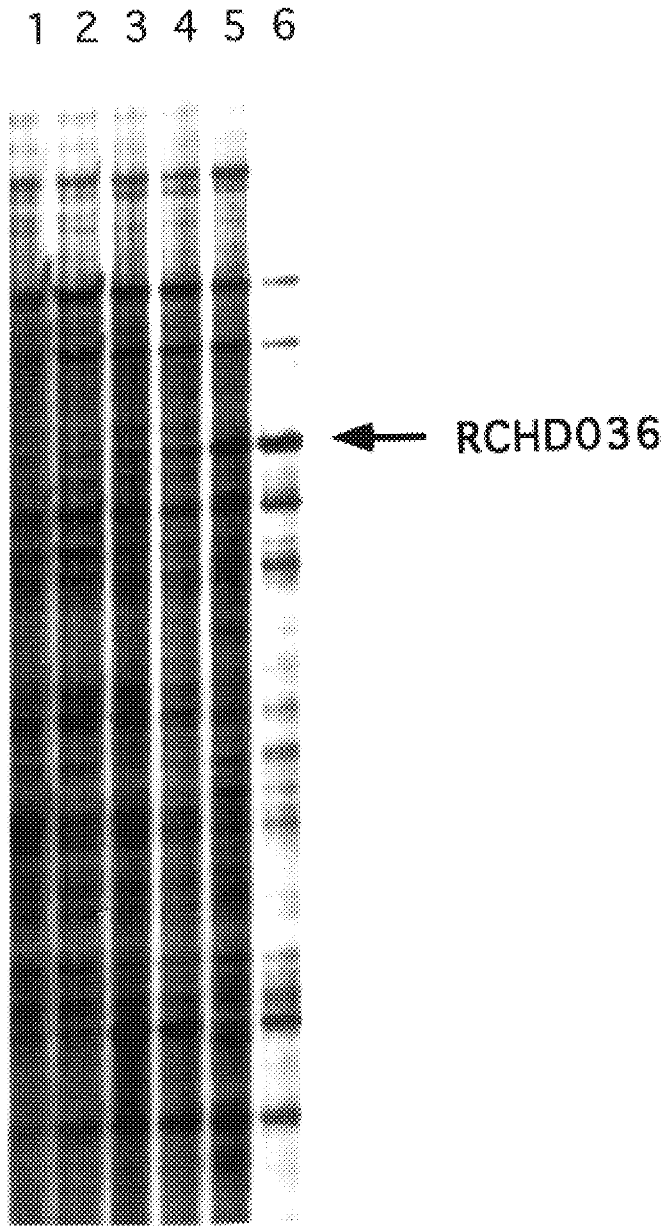

FIG. 16. IL-1 activated HUVEC differential display for rchd036. mRNA prepared from control HUVEC (lanes 3,4). 1 hr. of 10 units/ml IL-1 treatment (lanes 1,2), or 6 hr. treatment (lanes 5,6), was used in differential display reactions with the forward primer OPI17 (ggtggtgatg; SEQ ID NO:25) and reverse primer $T_{11}XC$, (SEQ ID NO:21) which is an equimolar mix of oligonucleotides where X is G, C, or A. The DNA corresponding to marked band, rchd036, was excised and amplified for Northern analysis and subcloning.

Figure 17:

FIG. 17. Northern blot analysis of endothelial IL-1 inducible band rchd036. 2 $\mu$g of total RNA from control (lane 1), 1 hr. (lane 2), and 6 hr. (lane 3) samples was eluted on an agarose gel, blotted, and incubated with a $^{32}$p labeled probe prepared from amplified band rchd036 sequences. The indicated band migrated with markers corresponding to approximately 8 kb.

FIG. 18. Band rchd036 DNA sequence; SEQ ID NO:4. The sequence was determined by sequencing the insert of pRCHD036, resulting from the ligation of amplified rchd036 sequences into the TA cloning vector.

Figure 19:
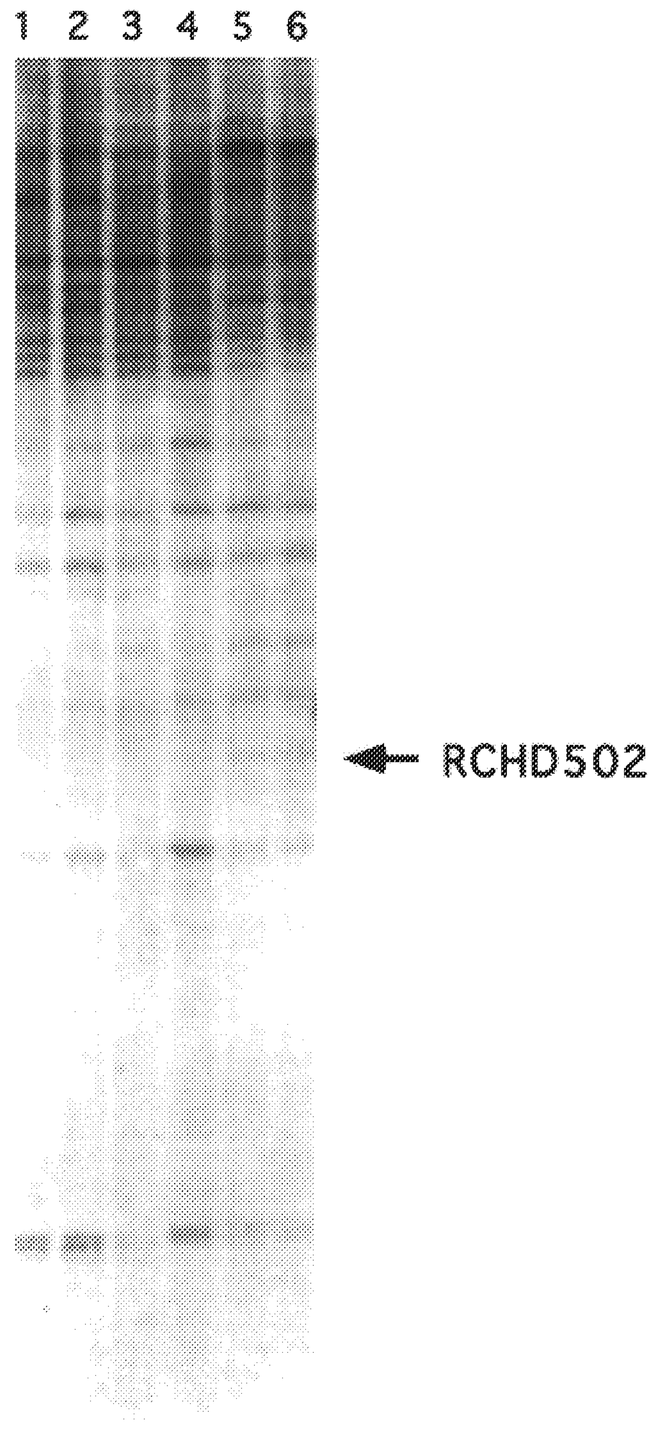

FIG. 19. Laminar shear stress HUVEC differential display. mRNA prepared from control HUVEC (lanes 3,4), 1 hr.

(lanes 1,2) of 10 dyn/$cm^2$ laminar shear stress treatment or 6 hr. treatment (lanes 5,6), was used in differential display reactions with the forward primer OPE7 (agatgcagcc) and reverse primer $T_{11}XA$, which is an equimolar mix of oligonucleotides where X is G, C, or A. The DNA corresponding to marked band, rchd502, was excised and amplified for Northern analysis and subcloning.

Figure 20:
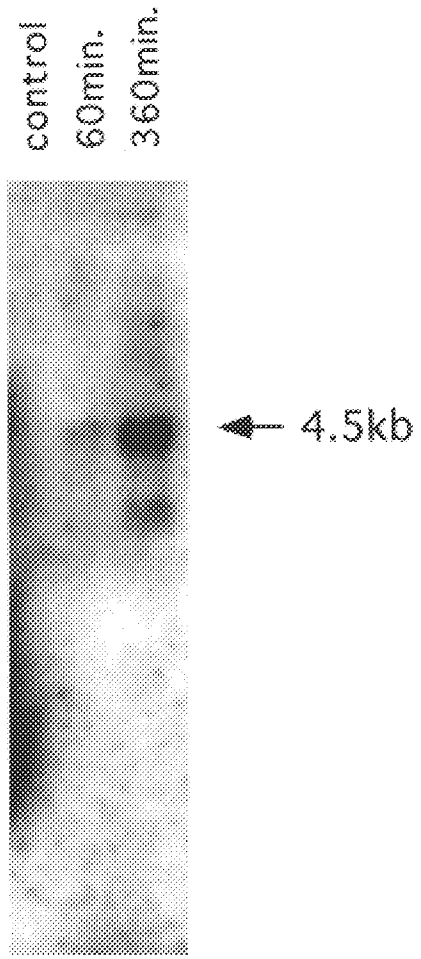

FIG. 20. Northern blot analysis of shear stress inducible band rchd502. 2 $\mu$g of total RNA from control, 1 hr. and 6 hr. shear stressed samples was eluted on an agarose gel, blotted, and incubated with a $^{32}P$ labeled probe prepared from amplified band rchd502 sequences. The indicated band migrates with markers corresponding to approximately 4.5 kb.

Figure 21:
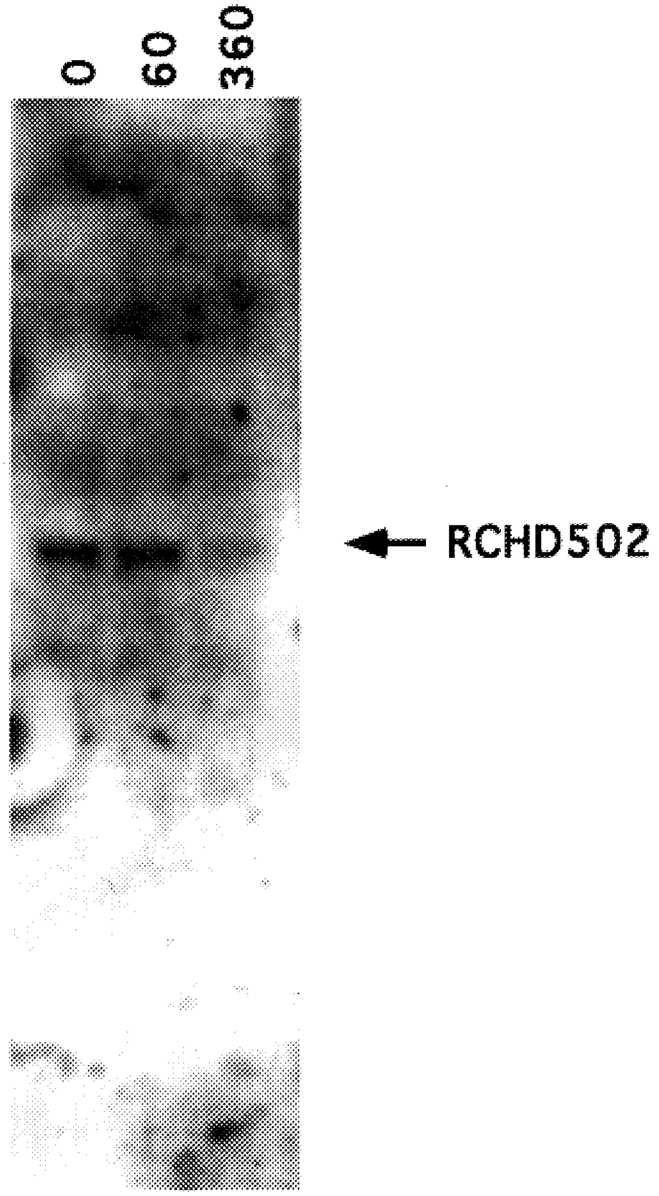

FIG. 21. Northern blot analysis of shear stress inducible band rchd502 on IL-1 blot. 2 $\mu$g of total RNA from control (lane 1), 1 hr. (lane 2), and 6 hr. (lane 3) IL-1 induced HUVEC samples was eluted on an agarose gel, blotted, and incubated with a $^{32}P$ labeled probe prepared from amplified band rchd502 sequences. A 4.5 kb band is seen which was not up-regulated by IL-1.

FIGS. 22A–D. DNA (SEQ ID NO:5) and encoded amino acid (SEQ ID NO:39) sequence of the rchd502 gene.

Figure 23:
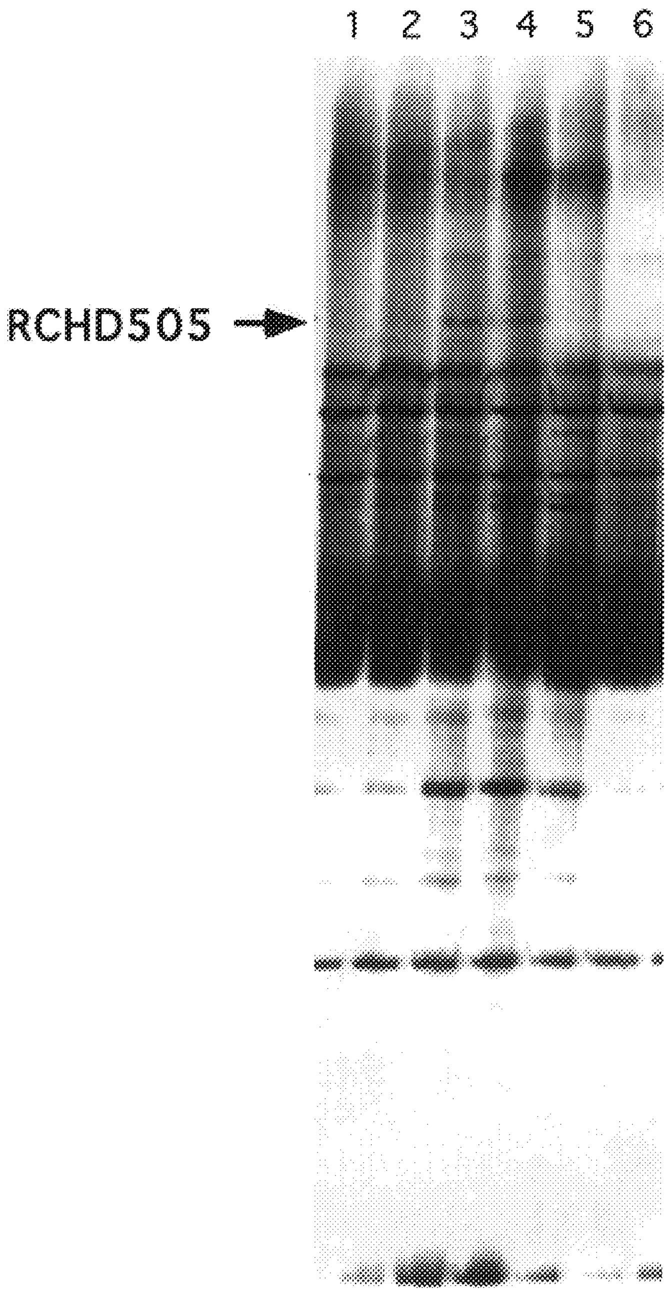

FIG. 23.Laminar shear stress HUVEC differential display for rchd505. mRNA prepared from control HUVEC (lanes 3,4), 1 hr. (lanes 1,2) or 6 hr. (lanes 5,6) of 10 dyn/$cm^2$ laminar shear stress treatment was used in differential display reactions with the forward primer OPE2 (ggtgcgggaa; SEQ ID NO:26) and reverse primer $T_{11}XA$, (SEQ ID NO:19) which is an equimolar mix of oligonucleotides where X is G,C, or A. The DNA corresponding to marked band, rchd505, was excised and amplified for Northern analysis and subcloning.

Figure 24:
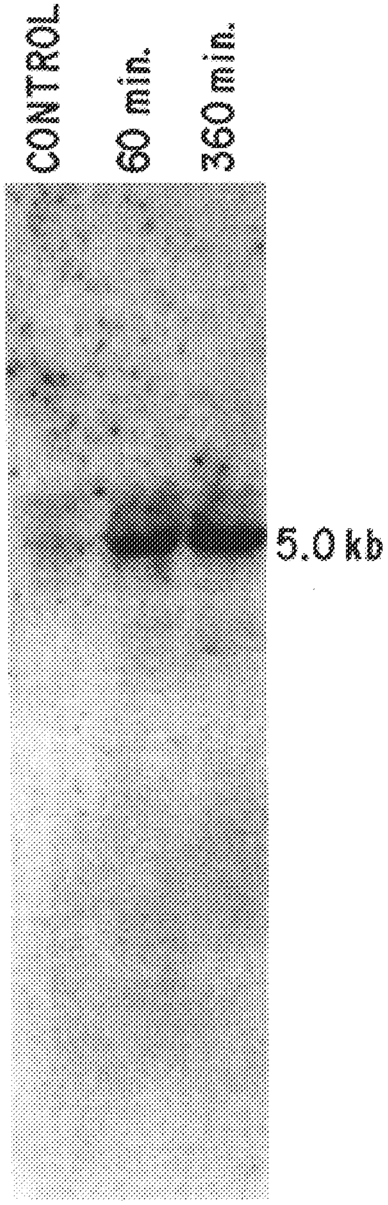

FIG. 24. Northern blot analysis of shear stress inducible band rchd505. 2 $\mu$g of total RNA from control, 1 hr. and 6 hr. shear stressed samples was eluted on an agarose gel, blotted, and incubated with a $^{32}P$ labeled probe prepared from amplified band rchd505 sequences. The indicated band migrated with markers corresponding to approximately 5.0 kb.

Figure 25:
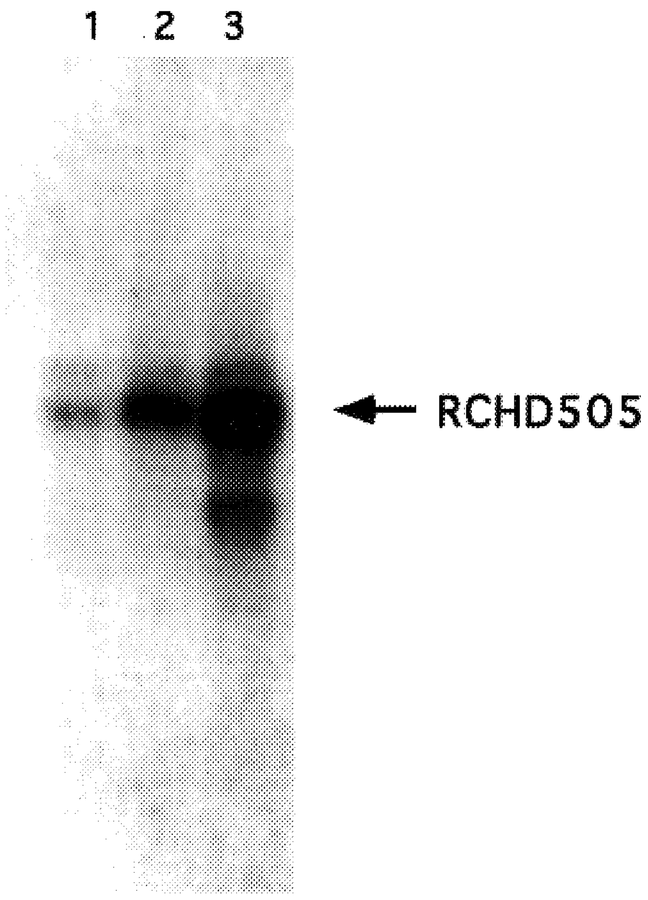

FIG. 25. Northern blot analysis of shear stress inducible band rchd505 on IL-1 blot. 2 $\mu$g of total RNA from control (lane 1), 1 hr. (lane 2), and 6 hr. (lane 3) IL-1 induced HUVEC samples was eluted on an agarose gel, blotted, and incubated with a $^{32}P$ labeled probe prepared from amplified band rchd505 sequences. A 5.0 kb inducible band is seen.

Figure 26:
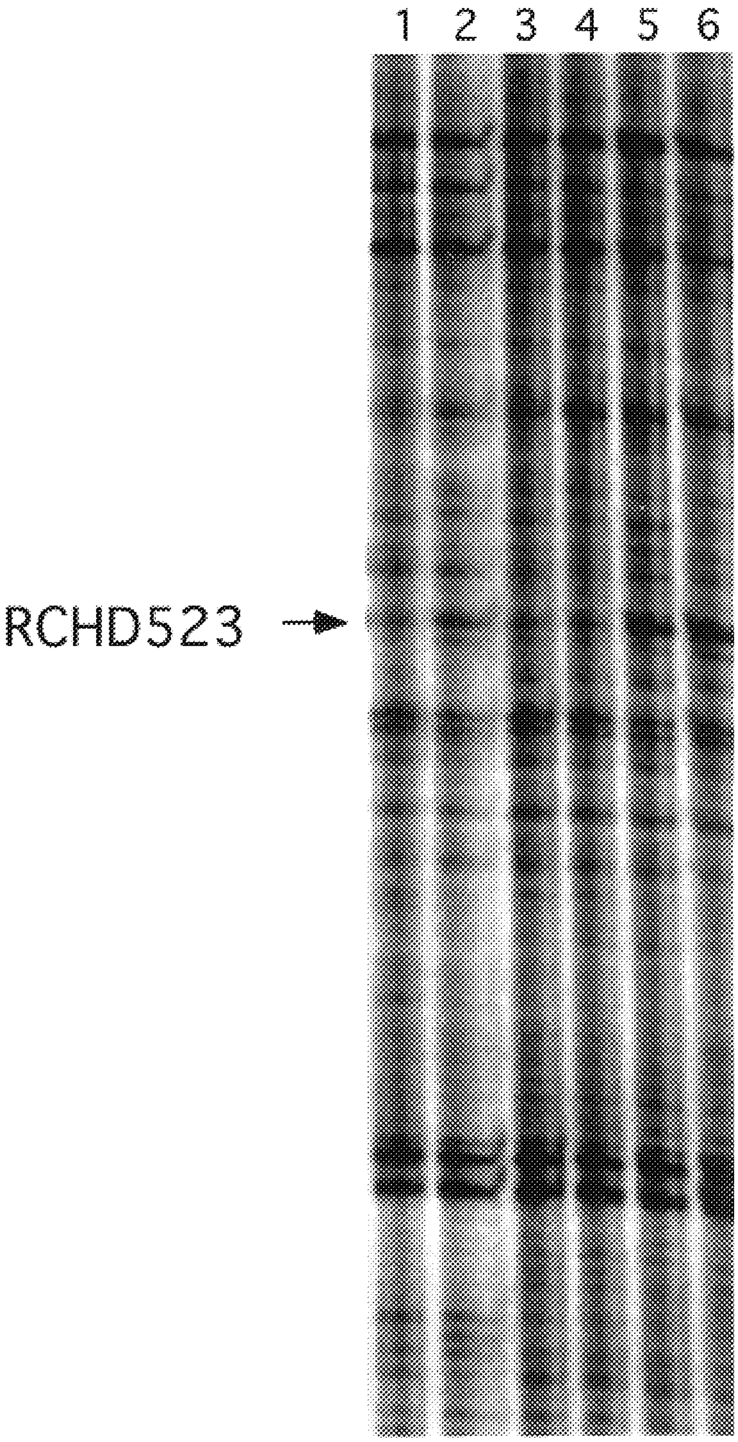

FIG. 26. Laminar shear stress HUVEC differential display for rchd523. mRNA prepared from control HUVEC (lanes 3,4), 1 hr. (lanes 1,2) or 6 hr. (lanes 5,6) of 10 dyn/$cm^2$ laminar shear stress treatment was used in differential display reactions with the forward primer OPI11 (acatgccgtg; SEQ ID NO:27) and reverse primer $T_{11}XC$, (SEQ ID NO:21) which is an equimolar mix of oligonucleotides where X is G,C, or A. The DNA corresponding to marked band, rchd523, was excised and amplified for Northern analysis and subcloning.

FIG. 27A–D. DNA (SEQ ID NO:6) and encoded amino acid (SEQ ID NO:38) sequence of the rchd523 gene.

Figure 28:
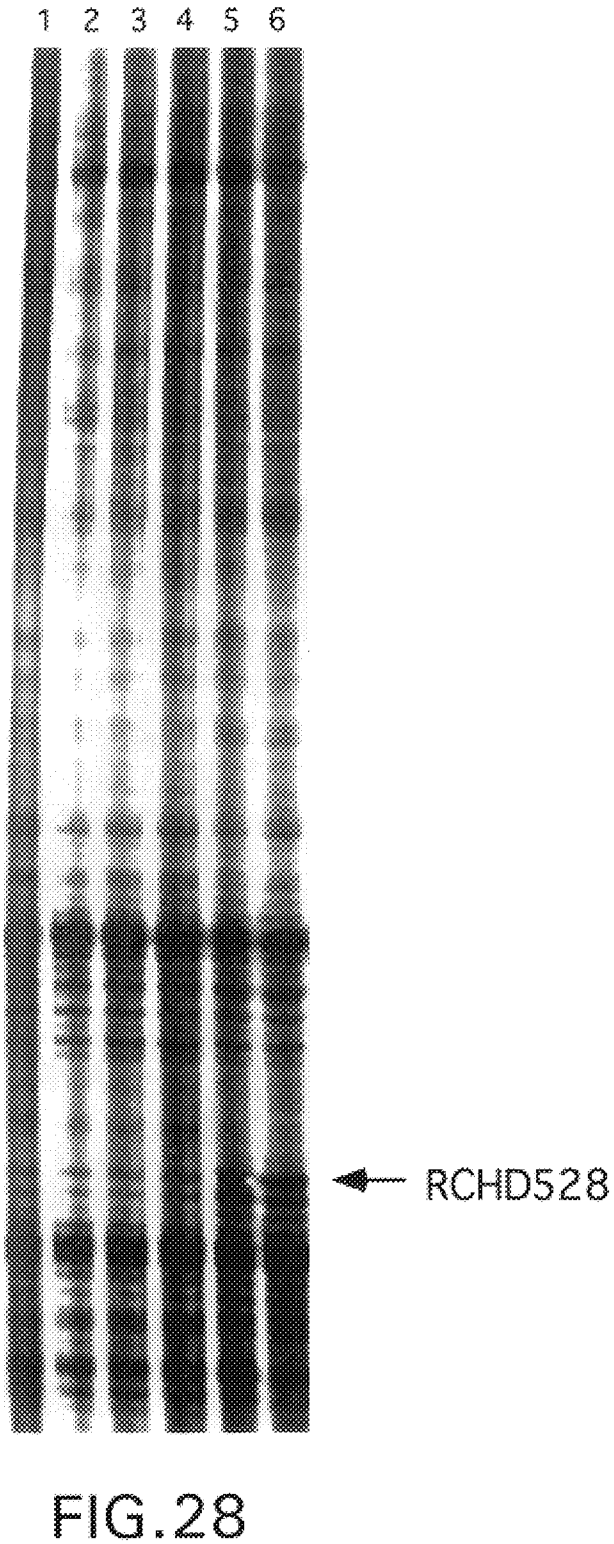

FIG. 28. Laminar shear stress HUVEC differential display for rchd528. mRNA prepared from control HUVEC (lanes 3,4), 1 hr. (lanes 1,2) or 6 hr. (lanes 5,6) of 10 dyn/$cm^2$ laminar shear stress treatment was used in differential display reactions with the forward primer OPI19 (aatgcgggag; SEQ ID NO:30) and reverse primer $T_{11}XG$, (SEQ ID NO:8) which is an equimolar mix of oligonucleotides where X is G,C, or A. The DNA corresponding to marked band, rchd528, was excised and amplified for Northern analysis and subcloning.

Figure 29:
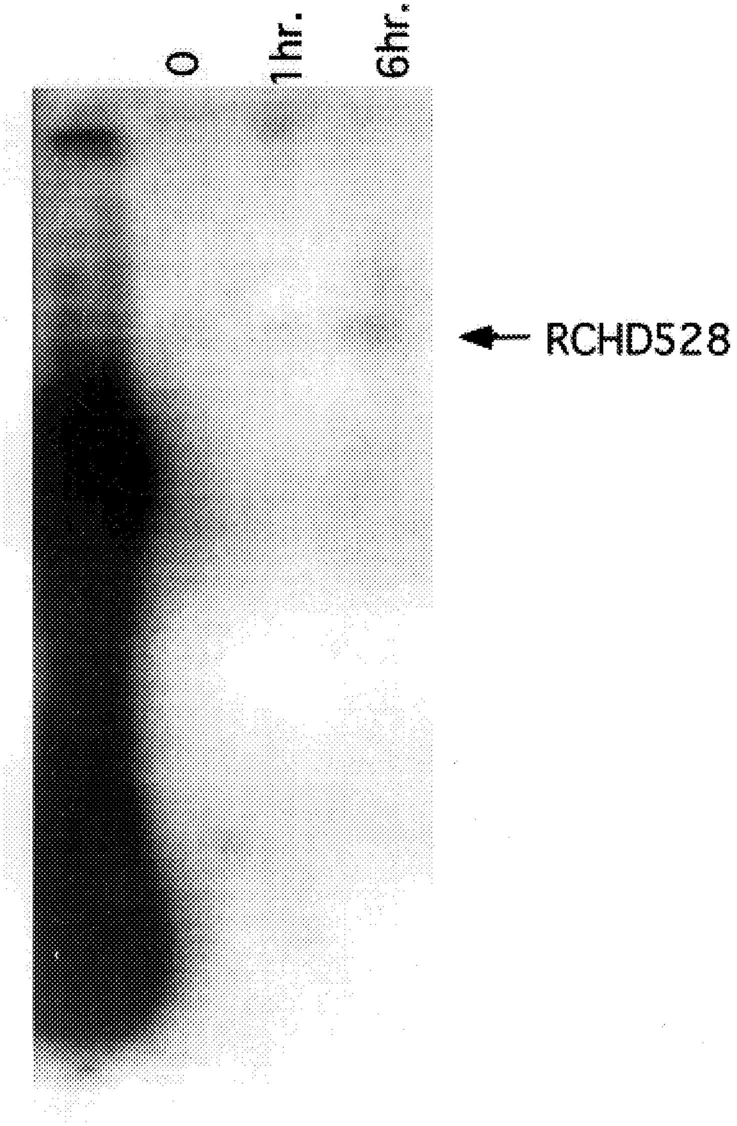

FIG. 29. Northern blot analysis of shear stress inducible band rchd528. 2 $\mu$g of total RNA from control (lane 1), 1 hr. (lane 2), and 6 hr. (lane 3) shear stressed samples was eluted on an agarose gel, blotted, and incubated with a $^{32}P$ labeled probe prepared from amplified band rchd528 sequences. The indicated band migrated with markers corresponding to approximately 5.0 kb.

FIGS. 30A–K. DNA (SEQ ID NO:7) and encoded amino acid (SEQ ID NO:40) sequence of the rchd528 gene.

Figure 31:
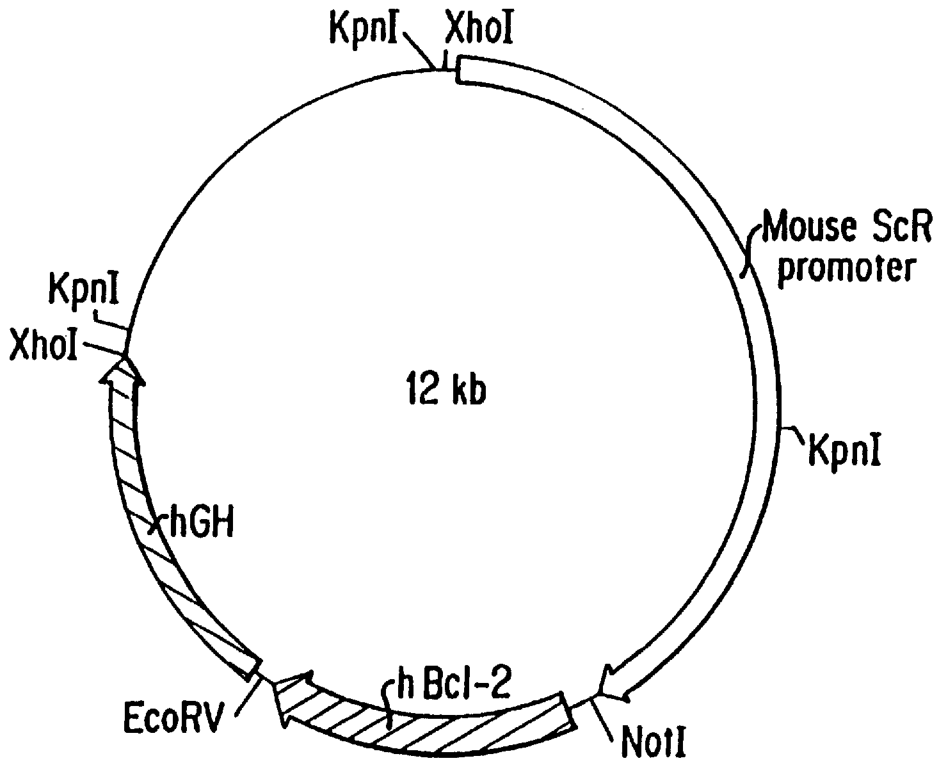

FIG. 31. Restriction map of plasmid pScR-bcl2.

Figure 32:
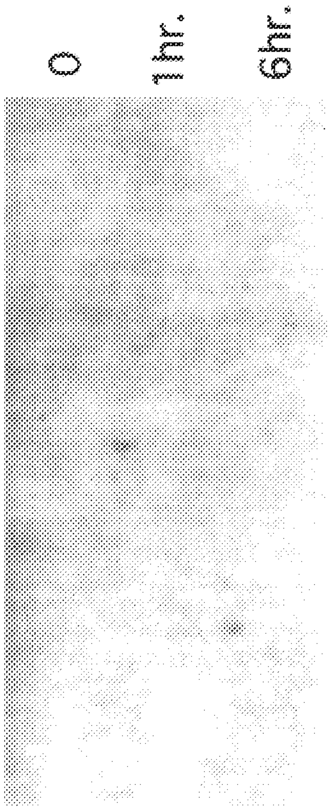

FIG. 32. Northern blot analysis of expression of rchd036 mRNA under shear stress. RNA was prepared from HUVEC's that were untreated (control) and treated with shear stress for 1 hr. and 6 hr. The blot was probed with labeled rchd036 DNA.

Figure 33:
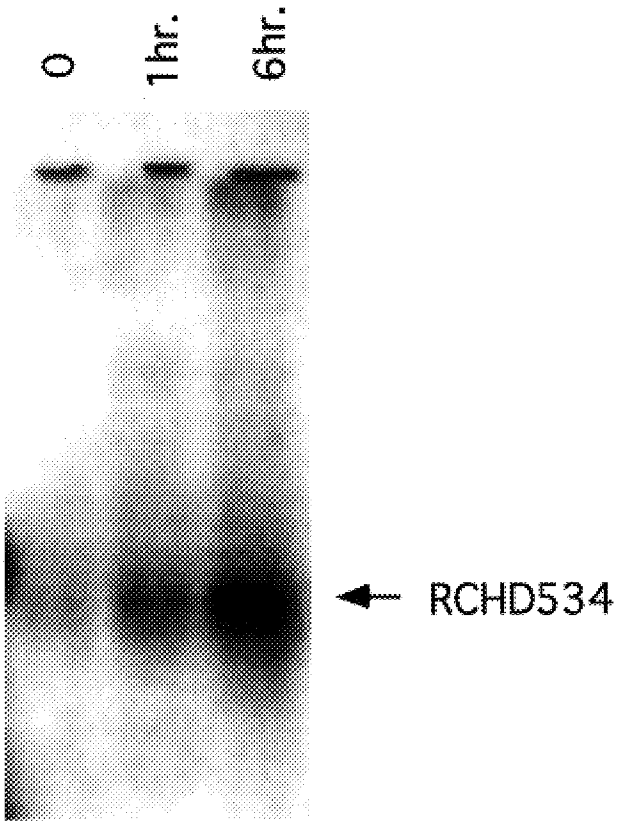

FIG. 33. Northern blot analysis of expression of rchd534 mRNA under shear stress. RNA was prepared from HUVEC's that were untreated (control) and treated with shear stress for 1 hr. and 6 hr. The blot was probed with labeled rchd534 DNA.

FIGS. 34A–D. DNA (SEQ ID NO:36) and encoded amino acid (SEQ ID NO:37) sequence of the rchd534 gene.

5. DETAILED DESCRIPTION OF THE INVENTION

Methods and compositions for the diagnosis and treatment of cardiovascular disease, including but not limited to atherosclerosis, ischemia/reperfusion, hypertension, restenosis, and arterial inflammation, are described. The invention is based, in part, on the evaluation of the expression and role of all genes that are differentially expressed in paradigms that are physiologically relevant to the disease condition. This permits the definition of disease pathways and the identification of targets in the pathway that are useful both diagnostically and therapeutically.

Genes, termed "target genes" and/or "fingerprint genes" which are differentially expressed in cardiovascular disease conditions, relative to their expression in normal, or non-cardiovascular disease conditions, are described in Section 5.4. Additionally, genes, termed "pathway genes" whose gene products exhibit an ability to interact with gene products involved in cardiovascular disease are also described in Section 5.4. Pathway genes may additionally have fingerprint and/or target gene characteristics. Methods for the identification of such fingerprint, target, and pathway genes are described in Sections 5.1, 5.2, and 5.3.

Further, the gene products of such fingerprint, target, and pathway genes are described in Section 5.4.2, antibodies to such gene products are described in Section 5.4.3, as are cell- and animal-based models of cardiovascular disease to which such gene products may contribute, in Section 5.4.4.

Methods for the identification of compounds which modulate the expression of genes or the activity of gene products involved in cardiovascular disease are described in Section 5.5. Methods for monitoring the efficacy of compounds during clinical trials are described in Section 5.5.4. Additionally described below, in Section 5.6, are methods for the treatment of cardiovascular disease.

Also discussed below, in Section 5.8, are methods for prognostic and diagnostic evaluation of cardiovascular disease, including the identification of subjects exhibiting a predisposition to this disease, and the imaging of cardiovascular disease conditions.

5.1. Identification of Differentially Expressed Genes

This section describes methods for the identification of genes which are involved in cardiovascular disease, including but not limited to atherosclerosis, ischemia/reperfusion, hypertension, restenosis, and arterial inflammation. Such genes may represent genes which are differentially expressed in cardiovascular disease conditions relative to their expression in normal, or non-cardiovascular disease conditions. Such differentially expressed genes may represent "target" and/or "fingerprint" genes. Methods for the identification of such differentially expressed genes are described, below, in this section. Methods for the further characterization of such differentially expressed genes, and for their identification as target and/or fingerprint genes, are presented, below, in Section 5.3.

"Differential expression" as used herein refers to both quantitative as well as qualitative differences in the genes' temporal and/or tissue expression patterns. Thus, a differentially expressed gene may have its expression activated or completely inactivated in normal versus cardiovascular disease conditions (e.g., treated with oxidized LDL versus untreated), or under control versus experimental conditions. Such a qualitatively regulated gene will exhibit an expression pattern within a given tissue or cell type which is detectable in either control or cardiovascular disease subjects, but is not detectable in both. Alternatively, such a qualitatively regulated gene will exhibit an expression pattern within a given tissue or cell type which is detectable in either control or experimental subjects, but is not detectable in both. "Detectable", as used herein, refers to an RNA expression pattern which is detectable via the standard techniques of differential display, reverse transcriptase-(RT-) PCR and/or Northern analyses, which are well known to those of skill in the art.

Alternatively, a differentially expressed gene may have its expression modulated, i.e., quantitatively increased or decreased, in normal versus cardiovascular disease states, or under control versus experimental conditions. The degree to which expression differs in normal versus cardiovascular disease or control versus experimental states need only be large enough to be visualized via standard characterization techniques, such as, for example, the differential display technique described below. Other such standard characterization techniques by which expression differences may be visualized include but are not limited to quantitative RT-PCR and Northern analyses.

Differentially expressed genes may be further described as target genes and/or fingerprint genes. "Fingerprint gene," as used herein, refers to a differentially expressed gene whose expression pattern may be utilized as part of a prognostic or diagnostic cardiovascular disease evaluation, or which, alternatively, may be used in methods for identifying compounds useful for the treatment of cardiovascular disease. A fingerprint gene may also have the characteristics of a target gene.

"Target gene", as used herein, refers to a differentially expressed gene involved in cardiovascular disease in a manner by which modulation of the level of target gene expression or of target gene product activity may act to ameliorate symptoms of cardiovascular disease. A target gene may also have the characteristics of a fingerprint gene.

A variety of methods may be utilized for the identification of genes which are involved in cardiovascular disease. These methods include but are not limited to the experimental paradigms described, below, in Section 5.1.1. Material from the paradigms may be characterized for the presence of differentially expressed gene sequences as discussed, below, in Section 5.1.2.

5.1.1. Paradigms for the Identification of Differentially Expressed Genes

One strategy for identifying genes that are involved in cardiovascular disease is to detect genes that are expressed differentially under conditions associated with the disease versus non-disease conditions. The sub-sections below describe a number of experimental systems, called paradigms, which may be used to detect such differentially expressed genes. In general, the paradigms include at least one experimental condition in which subjects or samples are treated in a manner associated with cardiovascular disease, in addition to at least one experimental control condition lacking such disease associated treatment. Differentially expressed genes are detected, as described herein, below, by comparing the pattern of gene expression between the experimental and control conditions.

Once a particular gene has been identified through the use of one such paradigm, its expression pattern may be further characterized by studying its expression in a different paradigm. A gene may, for example, be regulated one way in a given paradigm (e.g., up-regulation), but may be regulated differently in some other paradigm (e.g., down-regulation). Furthermore, while different genes may have similar expression patterns in one paradigm, their respective expression patterns may differ from one another under a different paradigm. Such use of multiple paradigms may be useful in distinguishing the roles and relative importance of particular genes in cardiovascular disease.

5.1.1.1. Foam Cell Paradigm—1

Among the paradigms which may be utilized for the identification of differentially expressed genes involved in atherosclerosis, for example, are paradigms designed to analyze those genes which may be involved in foam cell formation. Such paradigms may serve to identify genes involved in the differentiation of this cell type, or their uptake of oxidized LDL.

One embodiment of such a paradigm, hereinafter referred to as Paradigm A. First, human blood is drawn and peripheral monocytes are isolated by methods routinely practiced in the art. These human monocytes can then be used immediately or cultured in vitro, using methods routinely practiced in the art, for 5 to 9 days where they develop more macrophage-like characteristics such as the up-regulation of scavenger receptors. These cells are then treated for various lengths of time with agents thought to be involved in foam cell formation. These agents include but are not limited to oxidized LDL, acetylated LDL, lysophosphatidylcholine, and homocysteine. Control monocytes that are untreated or treated with native LDL are grown in parallel. At a certain time after addition of the test agents, the cells are harvested and analyzed for differential expression as described in detail in Section 5.1.2., below. The Example presented in Section 6, below, demonstrates in detail the use of such a foam cell paradigm to identify genes which are differentially expressed in treated versus control cells.

5.1.1.2. Foam Cell Paradigm—2

Alternative paradigms involving monocytes for detecting differentially expressed genes associated with atherosclerosis involve the simulation of the phenomenon of transmigration. When monocytes encounter arterial injury, they adhere to the vascular endothelial layer, transmigrate across this layer, and locate between the endothelium and the layer of smooth muscle cells that ring the artery. This phenomenon can be mimicked in vitro by culturing a layer of endothelial cells isolated, for example, from human umbilical cord. Once the endothelial monolayer forms, monocytes drawn from peripheral blood are cultured on top of the endothelium in the presence and absence of LDL. After several hours, the monocytes transmigrate through the endothelium and develop into foam cells after 3 to 5 days when exposed to LDL. In this system, as in vivo, the endothelial cells carry out the oxidation of LDL which is then taken up by the monocytes. As described in sub-section 5.1.2. below, the pattern of gene expression can then be compared between these foam cells and untreated monocytes.

5.1.1.3. Foam Cell Paradigm—3

Yet another system includes the third cell type, smooth muscle cell, that plays a critical role in atherogenesis (Navab et al., 1988, J. Clin. Invest., 82: 1853). In this system, a multilayer of human aortic smooth muscle cells was grown on a micropore filter covered with a gel layer of native collagen, and a monolayer of human aortic endothelial cells was grown on top of the collagen layer. Exposure of this coculture to human monocytes in the presence of chemotactic factor rFMLP resulted in monocyte attachment to the endothelial cells followed by migration across the endothelial monolayer into the collagen layer of the subendothelial space. This type of culture can also be treated with LDL to generate foam cells. The foam cells can then be harvested and their pattern of gene expression compared to that of untreated cells as explained below in sub-section 5.1.2.

5.1.1.4. In Vivo Monocyte Paradigm

An alternative embodiment of such paradigms for the study of monocytes, hereinafter referred to as Paradigm B, involves differential treatment of human subjects through the dietary control of lipid consumption. Such human subjects are held on a low fat/low cholesterol diet for three weeks, at which time blood is drawn, monocytes are isolated according to the methods routinely practiced in the art, and RNA is purified, as described below, in sub-section 5.1.2. These same patients are subsequently switched to a high fat/high cholesterol diet and monocyte RNA is purified again. The patients may also be fed a third, combination diet containing high fat/low cholesterol and monocyte RNA may be purified once again. The order in which patients receive the diets may be varied. The RNA derived from patients maintained on two of the diets, or on all three diets, may then be compared and analyzed for differential gene expression as, explained below in sub-section 5.1.2.

The Example presented in Section 7, below, demonstrates the use of such an in vivo monocyte paradigm to identify genes which are expressed differentially in monocytes of patients maintained on an atherogenic diet versus their expression under a control diet. Such a paradigm may also be used in conjunction with an in vitro preliminary detection system, as described in Section 7, below.

5.1.1.5. Endothelial Cell—IL-1 Paradigm

In addition to the detection of differential gene expression in monocytes, paradigms focusing on endothelial cells may be used to detect genes involved in cardiovascular disease. In one such paradigm, hereinafter referred to as Paradigm C, human umbilical vein endothelial cells (HUVEC's) are grown in vitro. Experimental cultures are treated with human IL-1β, a factor known to be involved in the inflammatory response, in order to mimic the physiologic conditions involved in the atherosclerotic state. Alternatively experimental HUVEC cultures may be treated with lysophosphatidylcholine, a major phospholipid component of atherogenic lipoproteins or oxidized human LDL. Control cultures are grown in the absence of these compounds.

After a certain period of exposure treatment, experimental and control cells are harvested and analyzed for differential gene expression as described in sub-section 5.1.2, below. The Example presented in Section 8, below, demonstrates the use of such an IL-1 induced endothelial cell paradigm to identify sequences which are differentially expressed in treated versus control cells.

5.1.1.6. Endothelial Cell—Shear Stress Paradigm

In another paradigm involving endothelial cells, hereinafter referred to as Paradigm D, cultures are exposed to fluid shear stress which is thought to be responsible for the prevalence of atherosclerotic lesions in areas of unusual circulatory flow. Unusual blood flow also plays a role in the harmful effects of ischemia/reperfusion, wherein an organ receiving inadequate blood supply is suddenly reperfused with an overabundance of blood when the obstruction is overcome.

Cultured HUVEC monolayers are exposed to laminar sheer stress by rotating the culture in a specialized apparatus containing liquid culture medium (Nagel et al., 1994, J. Clin. Invest. 94: 885–891). Static cultures grown in the same medium serve as controls. After a certain period of exposure to shear stress, experimental and control cells are harvested and analyzed for differential gene expression as described in sub-section 5.1.2, below. The Example presented in Section 9, below, demonstrates the use of such a shear stressed endothelial cell paradigm to identify sequences which are differentially expressed in exposed versus control cells.

In all such paradigms designed to identify genes which are involved in cardiovascular disease, including but not limited to those described above in Sections 5.1.1.1 through 5.1.1.6, compounds such as drugs known to have an ameliorative effect on the disease symptoms may be incorporated into the experimental system. Such compounds may include known therapeutics, as well as compounds that are not useful as therapeutics due to their harmful side effects. Test cells that are cultured as explained in the paradigms described in Sections 5.1.1.1 through 5.1.1.6, for example, may be exposed to one of these compounds and analyzed for differential gene expression with respect to untreated cells, according to the methods described below in Section 5.1.2. In principle, according to the particular paradigm, any cell type involved in the disease may be treated at any stage of the disease process by these compounds.

Test cells may also be compared to unrelated cells (e.g., fibroblasts) that are also treated with the compound, in order to screen out generic effects on gene expression that might not be related to the disease. Such generic effects might be manifest by changes in gene expression that are common to the test cells and the unrelated cells upon treatment with the compound.

By these methods, the genes and gene products upon which these compounds act can be identified and used in the assays described below to identify novel therapeutic compounds for the treatment of cardiovascular disease.

5.1.2. Analysis of Paradigm Material

In order to identify differentially expressed genes, RNA, either total or mRNA, may be isolated from one or more tissues of the subjects utilized in paradigms such as those described earlier in this Section. RNA samples are obtained from tissues of experimental subjects and from corresponding tissues of control subjects. Any RNA isolation technique which does not select against the isolation of mRNA may be utilized for the purification of such RNA samples. See, for example, Sambrook et al., 1989, Molecular Cloning, A Laboratory Manual, Cold Spring Harbor Press, N.Y.; and Ausubel, F. M. et al., eds., 1987–1993, Current Protocols in Molecular Biology, John Wiley & Sons, Inc. New York, both of which are incorporated herein by reference in their entirety. Additionally, large numbers of tissue samples may readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes may be identified by utilizing a variety of methods which are well known to those of skill in the art. For example, differential screening (Tedder, T. F. et al., 1988, Proc. Natl. Acad. Sci. USA 85:208–212), subtractive hybridization (Hedrick, S. M. et al., 1984, Nature 308:149–153; Lee, S. W. et al., 1984, Proc. Natl. Acad. Sci. USA 88:2825), and, preferably, differential display (Liang, P., and Pardee, A. B., 1993, U.S. Pat. No. 5,262,311, which is incorporated herein by reference in its entirety), may be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe may correspond to a total cell cDNA probe of a cell type derived from a control subject, while the second cDNA probe may correspond to a total cell cDNA probe of the same cell type derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, e.g., control and experimental tissue, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

The differential display technique describes a procedure, utilizing the well known polymerase chain reaction (PCR; the experimental embodiment set forth in Mullis, K. B., 1987, U.S. Pat. No. 4,683,202) which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction may include, but are not limited to, oligo dT-containing primers, preferably of the reverse primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts may be identified those which have been produced from differentially expressed genes.

The reverse oligonucleotide primer of the primer pairs may contain an oligo dT stretch of nucleotides, preferably eleven nucleotides long, at its 5' end, which hybridizes to the poly(A) tail of mRNA or to the complement of a cDNA reverse transcribed from an mRNA poly(A) tail. Second, in order to increase the specificity of the reverse primer, the primer may contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The forward primer may contain a nucleotide sequence expected, statistically, to have the ability to hybridize to cDNA sequences derived from the tissues of interest. The nucleotide sequence may be an arbitrary one, and the length of the forward oligonucleotide primer may range from about 9 to about 13 nucleotides, with about 10 nucleotides being preferred. Arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which may be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified via bulk techniques such as, for example, those described above, the differential expression of such putatively differentially expressed genes should be corroborated. Corroboration may be accomplished via, for example, such well known techniques as Northern analysis and/or RT-PCR.

Upon corroboration, the differentially expressed genes may be further characterized, and may be identified as target and/or fingerprint genes, as discussed, below, in Section 5.3.

Also, amplified sequences of differentially expressed genes obtained through, for example, differential display may be used to isolate full length clones of the corresponding gene. The full length coding portion of the gene may readily be isolated, without undue experimentation, by molecular biological techniques well known in the art. For example, the isolated differentially expressed amplified fragment may be labeled and used to screen a cDNA library. Alternatively, the labeled fragment may be used to screen a genomic library.

PCR technology may also be utilized to isolate full length cDNA sequences. As described, above, in this Section, the isolated, amplified gene fragments obtained through differential display have 5' terminal ends at some random point within the gene and have 3' terminal ends at a position preferably corresponding to the 3' end of the transcribed portion of the gene. Once nucleotide sequence information from an amplified fragment is obtained, the remainder of the gene (i.e., the 5' end of the gene, when utilizing differential display) may be obtained using, for example, RT-PCR.

In one embodiment of such a procedure for the identification and cloning of full length gene sequences, RNA may be isolated, following standard procedures, from an appropriate tissue or cellular source. A reverse transcription reaction may then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid may then be "tailed" with guanines using a standard terminal transferase reaction, the hybrid may be digested with RNAase H, and second strand synthesis may then be primed with a poly-C primer. Using the two primers, the 5' portion of the gene is amplified using PCR. Sequences obtained may then be isolated and recombined with previously isolated sequences to generate a full-length cDNA of the differentially expressed genes of the invention. For a review of cloning strategies and recombinant DNA techniques, see e.g., Sambrook et al., 1989, supra; and Ausubel et al., 1989, supra.

5.2. Identification of Pathway Genes

This section describes methods for the identification of genes, termed "pathway genes", involved in cardiovascular disease. "Pathway gene", as used herein, refers to a gene whose gene product exhibits the ability to interact with gene products involved in cardiovascular disease. A pathway gene may be differentially expressed and, therefore, may additionally have the characteristics of a target and/or fingerprint gene.

Any method suitable for detecting protein-protein interactions may be employed for identifying pathway gene products by identifying interactions between gene products and gene products known to be involved in cardiovascular disease. Such known gene products may be cellular or extracellular proteins. Those gene products which interact with such known gene products represent pathway gene products and the genes which encode them represent pathway genes.

Among the traditional methods which may be employed are co-immunoprecipitation, crosslinking and co-purification through gradients or chromatographic columns. Utilizing procedures such as these allows for the identification of pathway gene products. Once identified, a pathway gene product may be used, in conjunction with standard techniques, to identify its corresponding pathway gene. For example, at least a portion of the amino acid sequence of the pathway gene product may be ascertained using techniques well known to those of skill in the art, such as via the Edman degradation technique (see, e.g., Creighton, 1983, Proteins: Structures and Molecular Principles, W. H. Freeman & Co., N.Y., pp. 34–49). The amino acid sequence obtained may be used as a guide for the generation of oligonucleotide mixtures that can be used to screen for pathway gene sequences. Screening made be accomplished, for example by standard hybridization or PCR techniques. Techniques for the generation of oligonucleotide mixtures and screening are well-known. (See, e.g., Ausubel, supra., and PCR Protocols: A Guide to Methods and Applications, 1990, Innis, M. et al., eds. Academic Press, Inc., New York).

Additionally, methods may be employed which result in the simultaneous identification of pathway genes which encode the protein interacting with a protein involved in cardiovascular disease. These methods include, for example, probing expression libraries with labeled protein known or suggested to be involved in cardiovascular disease, using this protein in a manner similar to the well known technique of antibody probing of λgt11 libraries.

One such method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, and the other consists of the activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the activator's binding sites. Either hybrid protein alone cannot activate transcription of the reporter gene, the DNA-binding domain hybrid because it does not provide activation function and the activation domain hybrid because it cannot localize to the activator's binding sites. Interaction of the two proteins reconstitutes the functional activator protein and results in expression of the reporter gene, which is detected by an assay for the reporter gene product.

The two-hybrid system or related methodology may be used to screen activation domain libraries for proteins that interact with a known "bait" gene protein. Total genomic or cDNA sequences may be fused to the DNA encoding an activation domain. Such a library and a plasmid encoding a hybrid of the bait gene protein fused to the DNA-binding domain may be cotransformed into a yeast reporter strain, and the resulting transformants may be screened for those that express the reporter gene. These colonies may be purified and the library plasmids responsible for reporter gene expression may be isolated. DNA sequencing may then be used to identify the proteins encoded by the library plasmids.

For example, and not by way of limitation, the bait gene may be cloned into a vector such that it is translationally fused to the DNA encoding the DNA-binding domain of the GAL4 protein. Also by way of example, for the isolation of genes involved in cardiovascular disease, previously isolated genes known or suggested to play a part in cardiovascular disease may be used as the bait genes. These include but are not limited to the genes for bFGF, IGF-I, VEGF, IL-1, M-CSF, TGFβ, TGFα, TNFα, HB-EGF, PDGF, IFN-γ, and GM-CSF, to name a few.

A cDNA library of the cell line from which proteins that interact with bait gene are to be detected can be made using methods routinely practiced in the art. According to the particular system described herein, for example, the cDNA fragments may be inserted into a vector such that they are translationally fused to the activation domain of GAL4. This library may be co-transformed along with the bait gene-GAL4 fusion plasmid into a yeast strain which contains a lacZ gene driven by a promoter which contains the GAL4 activation sequence. A cDNA encoded protein, fused to the GAL4 activation domain, that interacts with bait gene will reconstitute an active GAL4 protein and thereby drive expression of the lacZ gene. Colonies which express lacZ may be detected by their blue color in the presence of X-gal. The cDNA may then be purified from these strains, and used to produce and isolate the bait gene-interacting protein using techniques routinely practiced in the art.

Once a pathway gene has been identified and isolated, it may be further characterized as, for example, discussed below, in Section 5.3.

5.3. Characterization of Differentially Expressed and Pathway Genes

Differentially expressed genes, such as those identified via the methods discussed, above, in Section 5.1.1, pathway genes, such as those identified via the methods discussed, above, in Section 5.2, as well as genes identified by alternative means, may be further characterized by utilizing, for example, methods such as those discussed herein. Such genes will be referred to herein as "identified genes".

Analyses such as those described herein will yield information regarding the biological function of the identified genes. An assessment of the biological function of the differentially expressed genes, in addition, will allow for their designation as target and/or fingerprint genes. Specifically, any of the differentially expressed genes whose further characterization indicates that a modulation of the gene's expression or a modulation of the gene product's activity may ameliorate cardiovascular disease will be designated "target genes", as defined, above, in Section 5.1. Such target genes and target gene products, along with those discussed below, will constitute the focus of the compound discovery strategies discussed, below, in Section 5.5.

Any of the differentially expressed genes whose further characterization indicates that such modulations may not positively affect cardiovascular disease, but whose expression pattern contributes to a gene expression "fingerprint pattern" correlative of, for example, a cardiovascular disease condition will be designated a "fingerprint gene". "Fingerprint patterns" will be more fully discussed, below, in Section 5.8. It should be noted that each of the target genes may also function as fingerprint genes, as may all or a subset of the pathway genes.

It should further be noted that the pathway genes may also be characterized according to techniques such as those described herein. Those pathway genes which yield information indicating that they are differentially expressed and that modulation of the gene's expression or a modulation of the gene product's activity may ameliorate cardiovascular disease will be also be designated "target genes". Such target genes and target gene products, along with those discussed above, will constitute the focus of the compound discovery strategies discussed, below, in Section 5.5.

It should be additionally noted that the characterization of one or more of the pathway genes may reveal a lack of differential expression, but evidence that modulation of the gene's activity or expression may, nonetheless, ameliorate cardiovascular disease symptoms. In such cases, these genes and gene products would also be considered a focus of the compound discovery strategies of Section 5.5, below.

In instances wherein a pathway gene's characterization indicates that modulation of gene expression or gene product activity may not positively affect cardiovascular disease, but whose expression is differentially expressed and which contributes to a gene expression fingerprint pattern correlative of, for example, a cardiovascular disease state, such pathway genes may additionally be designated as fingerprint genes.

Among the techniques whereby the identified genes may be further characterized, the nucleotide sequence of the identified genes, which may be obtained by utilizing standard techniques well known to those of skill in the art, may be used to further characterize such genes. For example, the sequence of the identified genes may reveal homologies to one or more known sequence motifs which may yield information regarding the biological function of the identified gene product.

Second, an analysis of the tissue distribution of the mRNA produced by the identified genes may be conducted, utilizing standard techniques well known to those of skill in the art. Such techniques may include, for example, Northern analyses and RT-PCR. Such analyses provide information as to whether the identified genes are expressed in tissues expected to contribute to cardiovascular disease. Such analyses may also provide quantitative information regarding steady state mRNA regulation, yielding data concerning which of the identified genes exhibits a high level of regulation in, preferably, tissues which may be expected to contribute to cardiovascular disease.

Such analyses may also be performed on an isolated cell population of a particular cell type derived from a given tissue. Additionally, standard in situ hybridization techniques may be utilized to provide information regarding which cells within a given tissue express the identified gene. Such analyses may provide information regarding the biological function of an identified gene relative to cardiovascular disease in instances wherein only a subset of the cells within the tissue is thought to be relevant to cardiovascular disease.

Such an in situ hybridization analysis is described in the example in Section 14, below. Specifically, the roles of the rchd502 and rchd528 genes in cardiovascular disease were further demonstrated by detecting high levels of their expression specifically within the endothelial cells of diseased tissue removed from a human cardiovascular disease patient, and not in any other cell type present in the tissue, including smooth muscle cells and macrophages. These results clearly demonstrate how detection of differentially expressed genes in the paradigms described herein leads to biologically relevant, novel, specific targets for the treatment and diagnosis of cardiovascular disease.

Third, the sequences of the identified genes may be used, utilizing standard techniques, to place the genes onto genetic maps, e.g., mouse (Copeland & Jenkins, 1991, Trends in Genetics 7: 113–118) and human genetic maps (Cohen, et al., 1993, Nature 366: 698–701). Such mapping information may yield information regarding the genes' importance to human disease by, for example, identifying genes which map near genetic regions to which known genetic cardiovascular disease tendencies map.

Fourth, the biological function of the identified genes may be more directly assessed by utilizing relevant in vivo and in vitro systems. In vivo systems may include, but are not limited to, animal systems which naturally exhibit cardiovascular disease predisposition, or ones which have been engineered to exhibit such symptoms, including but not limited to the apoE-deficient atherosclerosis mouse model (Plump et al., 1992, Cell 71: 343–353). Such systems are discussed in Section 5.4.4.1, below.

The use of such an in vivo system is described in detail in the example provided in Section 7, below, confirming the role of the target gene bcl-2 (see Table 1, in Section 5.4.1, below). Briefly, bcl-2 expression first was shown to be down-regulated in the apoE-deficient atherosclerosis mouse model. Then, a transgenic mouse was engineered bearing the human bcl-2 gene under the control of a promoter which is induced in monocyte foam cells under atherogenic conditions. To test the effect of the induction of bcl-2 under such conditions, the transgenic mouse is crossed with the apoE-deficient mouse. apoE-deficient progeny bearing the highly expressible bcl-2 gene are then examined for plaque formation and development. Reduction in plaque formation and development in these progeny confirms the effectiveness of intervening in cardiovascular disease through this target gene.

In vitro systems may include, but are not limited to, cell-based systems comprising cell types known or suspected of involvement in cardiovascular disease. Such systems are discussed in detail, below, in Section 5.4.4.2.

In further characterizing the biological function of the identified genes, the expression of these genes may be modulated within the in vivo and/or in vitro systems, i.e., either over- or underexpressed, and the subsequent effect on the system then assayed. Alternatively, the activity of the product of the identified gene may be modulated by either increasing or decreasing the level of activity in the in vivo and/or in vitro system of interest, and its subsequent effect then assayed.

The information obtained through such characterizations may suggest relevant methods for the treatment of cardiovascular disease involving the gene of interest. For example, treatment may include a modulation of gene expression and/or gene product activity. Characterization procedures such as those described herein may indicate where such modulation should involve an increase or a decrease in the expression or activity of the gene or gene product of interest.

For example, genes which are up-regulated under disease conditions may be involved in causing or exacerbating the disease condition. Treatments directed at down-regulating the activity of such harmfully expressed genes will ameliorate the disease condition. On the other hand, the up-regulation of genes under disease conditions may be part of a protective response by affected cells. Treatments directed at increasing or enhancing the activity of such up-regulated gene products, especially in individuals lacking normal up-regulation, will similarly ameliorate disease conditions. Such methods of treatment are discussed, below, in Section 5.6.

5.4. Differentially Expressed and Pathway Genes

Identified genes, which include but are not limited to differentially expressed genes such as those identified in Section 5.1.1, above, and pathway genes, such as those identified in Section 5.2, above, are described herein. Specifically, the nucleic acid sequences and gene products of such identified genes are described herein. Further, antibodies directed against the identified genes' products, and cell- and animal-based models by which the identified genes may be further characterized and utilized are also discussed in this Section.

5.4.1. Differentially Expressed and Pathway Gene Sequences

The differentially expressed and pathway genes of the invention are listed below, in Table 1. Differentially expressed and pathway gene nucleotide sequences are shown in FIGS. 8, 12, 15, 18, 22A–D, 27A–D, 30A–K, and 34A–D.

Table 1 lists differentially expressed genes identified through, for example, the paradigms discussed, above, in Section 5.1.1, and below, in the examples presented in Sections 6 through 9. Table 1 also summarizes information regarding the further characterization of such genes.

First, the paradigm used initially to detect the differentially expressed gene is described under the column headed "Paradigm of Original Detection". The expression patterns of those genes which have been shown to be differentially expressed, for example, under one or more of the paradigm conditions described in Section 5.1.1 are summarized under the column headed "Paradigm Expression Pattern". For each of the tested genes, the paradigm which was used and the difference in the expression of the gene among the samples generated is shown. "↑" indicates that gene expression is up-regulated (i.e., there is an increase in the amount of detectable mRNA) among the samples generated, while "↓" indicates that gene expression is down-regulated (i.e., there is a decrease in the amount of detectable mRNA) among the samples generated. "Detectable" as used herein, refers to levels of mRNA which are detectable via, for example, standard Northern and/or RT-PCR techniques which are well known to those of skill in the art.

Cell types in which differential expression was detected are also summarized in Table 1 under the column headed "Cell Type Detected in". The column headed "Chromosomal Location" provides the human chromosome number on which the gene is located. Additionally, in instances wherein the genes contain nucleotide sequences similar or homologous to sequences found in nucleic acid databases, references to such similarities are listed.

The genes listed in Table 1 may be obtained using cloning methods well known to those skilled in the art, including but not limited to the use of appropriate probes to detect the genes within an appropriate cDNA or gDNA (genomic DNA) library. (See, for example, Sambrook et al., 1989, Molecular Cloning: A Laboratory Manual, Cold Spring Harbor Laboratories, which is incorporated by reference herein in its entirety). Probes for the novel sequences reported herein may be obtained directly from the isolated clones deposited with the NRRL or ATCC, as indicated in Table 2, below. Alternatively, oligonucleotide probes for the novel genes may be synthesized based on the DNA sequences disclosed herein in FIGS. 8, 12, 15, 18, 22A–D, 27A–D, 30A–K, and 34A–D. Such synthetic oligonucleotides may be similarly produced based on the sequences provided for the previously known genes described in the following references: Cleary et al., 1986, Cell 47: 19–28 (bcl-2); Takahashi et al., 1990, J. Biochem 108: 145–148 (glutathione peroxidase); and Jones et al., 1993, J. Biol. Chem. 268: 9049–9054 (prostaglandin endoperoxide synthase II), each of which is incorporated herein in its entirety.

The sequence obtained from clones containing partial coding sequences or non-coding sequences can be used to obtain the entire coding region by using the RACE method (Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Oligonucleotides can be designed based on the sequence obtained from the partial clone that can amplify a reverse transcribed mRNA encoding the entire coding sequence. This method was used, as described in the example in Section 9, below, to obtain the entire coding region of the rchd523 gene.

Alternatively, probes can be used to screen cDNA libraries prepared from an appropriate cell or cell line in which the gene is transcribed. For example, the genes described herein that were detected in monocytes may be cloned from a cDNA library prepared from monocytes isolated as described in Section 7.1.1, below. In fact, as described in detail in the example in Section 9, below, this method was applied in order to obtain the entire coding region of the rchd534 gene. Briefly, the up-regulation of this gene was detected, under Paradigm D, in HUVEC's subjected to shear stress. Then, amplified partial sequence of the rchd534 gene was subcloned. The insert was then isolated and used to probe a cDNA library prepared from shear stress treated HUVEC's. A cDNA clone containing the entire rchd534 coding region was detected, isolated, and sequenced.

The genes described herein that were detected in endothelial cells may also be cloned from a cDNA library constructed from endothelial cells isolated as described in Progress in Hemostasis and Thrombosis, Vol. 3, P. Spaet, editor, Grune & Stratton Inc., New York, 1–28. Alternatively, the genes may be retrieved from a human placenta cDNA library (Clontech Laboratories, Palo Alto, Calif.), according to Takahashi et al., 1990, supra; a HUVEC cDNA library as described in Jones et al. 1993, supra; or an acute lymphoblastic leukemia (SUP-B2) cDNA library as described in Cleary et al., 1986, supra, for example. Genomic DNA libraries can be prepared from any source.

TABLE 1

| Differentially Expressed and Pathway Genes | | | | | | | |
|---|---|---|---|---|---|---|---|
| Gene | Seq. ID # | Paradigm of Original Detection | Paradigm Expr. Pattern | Cell Type Detected in | Chromosomal Location | Ref | Seq. |
| Band 14: bcl-2 | | B (Section 5.1.1.4) | ⇓ | Monocytes | | 1 | |
| Glutathione peroxidase | | B | ⇓ | Monocytes | | 2 | |
| rchd005 | 1 | C (Section 5.1.1.5) | ⇑ | Endothelial | | New 3 | FIG. 8 |
| rchd024 | 2 | C | ⇑ | Endothelial | 4 | New | FIG. 12 |
| rchd032 | 3 | C | ⇑ | Endothelial | | New | FIG. 15 |
| rchd036 | 4 | C | ⇑ | Endothelial | 15 | New | FIG. 18 |
| rchd502 | 5 | D (Section 5.1.1.6) | ⇑ | Endothelial | | New 4 | FIG. 22 |
| rchd505: COX II | | D | ⇑ | Endothelial | | 5 | |
| rchd523 | 6 | D | ⇑ | Endothelial | 7 | New | FIGS. 27A–D |
| rchd528 | 7 | D | ⇑ | Endothelial | | New 6 | FIGS. 30A–K |
| rchd530: MnSOD | | D | ⇑ | Endothelial | | 7 | |
| rchd534 | 36 | D | ⇑ | Endothelial | 15 | New 8 | FIGS. 34A–D |

1 Cleary et al., 1986, Cell 47: 19–28.
2 Takahashi et al., 1990, J. Biochem. 108: 145–148.
3 Shark Na—K—Cl cotransporter, Ku et al., 1994 Proc. Natl. Acad. Sci. U.S.A. 91: 2201–2205.
4 Rat matrin P/G, Hakes et al., 1991 Proc. Natl. Acad. Sci. U.S.A. 88: 6186–6190.
5 Jones et al., 1993, J. Biol. Chem. 268: 9049–9054.
6 Xenopus Xotch (homolog of Drosophila Notch), Coffman et al., 1990, Science 249: 1438–1441.
7 Heckl, 1988, Nucl. Acids Res. 16: 6224.
8 Drosohila Mothers against dpp (Mad), Sekelsky et al., 1995, Genetics 139: 1347–1358.

Table 2, below, lists isolated clones that contain sequences of the novel genes listed in Table 1. Such clones were produced from amplified sequences of the indicated differential display band which were subcloned into the TA cloning vector (Invitrogen, San Diego, Calif.), as described in Section 6.1, below. Also listed in Table 2, below, are the strains deposited with the NRRL or ATCC which contain each such clone. Such strains were produced by transforming *E. coli* strain INVαF' (Invitrogen) with the indicated plasmid, as described in Section 6.1, below. The names of the plasmids containing the entire coding region of a novel gene bear the prefix pFCHD, and the names of the strains carrying these plasmids bear the prefix FCHD.

TABLE 2

| GENE | Strain Deposited with NRRL | Plasmid Clone Contained within Deposited Strain |
|---|---|---|
| rchd005 | RCHD005 | pRCHD005 |
| rchd024 | RCHD024 | pRCHD024 |
| rchd032 | RCHD032 | pRCHD032 |
| rchd036 | RCHD036 | pRCHD036 |
| rchd502 | FCHD502SF | pFCHD502SF |
| | FCHD502SJ | pFCHD502SJ |
| | RCHD502 | pRCHD502 |
| rchd523 | FCHD523 | pFCHD523 |
| | RCDH523 | pRCHD523 |
| rchd528 | FCHD528A | pFCHD528A |
| | FCHD528B | pFCHD528B |
| | FCHD528C | pFCHD528C |
| | RCHD528 | pRCHD528 |
| rchd534 | FCHD534 | pFCHD534 |

As used herein, "differentially expressed gene" (i.e. target and fingerprint gene) or "pathway gene" refers to (a) a gene containing at least one of the DNA sequences disclosed herein (as shown in FIGS. 8, 12, 15, 18, 22A–D, 27A–D, 30A–K, and 34A–D, or contained in the clones listed in Table 2, as deposited with the NRRL or ATCC; (b) any DNA sequence that encodes the amino acid sequence encoded by the DNA sequences disclosed herein (as shown in FIGS. 8, 12, 15, 18, 22A–D, 27A–D, 30A–K, and 34A–D, contained in the clones, listed in Table 2, as deposited with the NRRL or ATCC or contained within the coding region of the gene to which the DNA sequences disclosed herein (as shown in FIGS. 8, 12, 15, 18, 22A–D, 27A–D, 30A–K, and 34A–D or contained in the clones listed in Table 2, as deposited with the NRRL or ATCC, belong; (c) any DNA sequence that hybridizes to the complement of the coding sequences disclosed herein, contained in the clones listed in Table 2, as deposited with the NRRL or ATCC, or contained within the coding region of the gene to which the DNA sequences disclosed herein (as shown in FIGS. 8, 12, 15, 18, 22A–D, 27A–D, 30A–K and 34A–D or contained in the clones listed in Table 2, as deposited with the NRRL or ATCC, belong, under highly stringent conditions, e.g., hybridization to filter-bound DNA in 0.5M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a gene product functionally equivalent to a gene product encoded by sequences contained within the clones listed in Table 2; and/or (d) any DNA sequence that hybridizes to the complement of the coding sequences disclosed herein, (as shown in FIGS. 8, 12, 15, 18, 22, 27, 30, and 34) contained in the clones listed in Table 2, as deposited with the NRRL or ATCC, or contained within the coding region of the gene to which DNA sequences disclosed herein (as shown in FIGS. 8, 12, 15, 18, 22A–D, 27A–D, 30A–K, and 34A–D or contained in the clones, listed in Table 2, as deposited with the NRRL or ATCC, belong, under less stringent conditions, such as moderately stringent conditions, e.g., washing in 0.2×SSC/0.1% SDS at 42° C. (Ausubel et al., 1989, supra), yet which still encodes a functionally equivalent gene product.

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target gene antisense molecules, useful, for example, in target gene regulation and/or as antisense primers in amplification reactions of target gene nucleic acid sequences. Further, such sequences may be used as part of ribozyme and/or triple helix sequences, also useful for target gene regulation. Still further, such molecules may be used as components of diagnostic methods whereby the presence of a cardiovascular disease-causing allele, may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. The invention includes fragments of any of the DNA sequences disclosed herein.

In addition to the gene sequences described above, homologues of such sequences, as may, for example be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated differentially expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Further, a previously unknown differentially expressed or pathway gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a differentially expressed or pathway gene allele.

The PCR product may be subcloned and sequenced to insure that the amplified sequences represent the sequences of a differentially expressed or pathway gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the differentially expressed or pathway gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to cardiovascular disease symptoms. Mutant alleles and mutant allele products may then be utilized in the therapeutic and diagnostic assay systems described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified through methods routinely practiced in the art, and subjected to sequence analysis as described, above, in this Section.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.4.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described in this Section, above.

5.4.2. Differentially Expressed and Pathway Gene Products

Differentially expressed and pathway gene products include those proteins encoded by the differentially expressed and pathway gene sequences described in Section 5.4.1, above. Specifically, differentially expressed and pathway gene products may include differentially expressed and pathway gene polypeptides encoded by the differentially expressed and pathway gene sequences contained in the clones listed in Table 2, above, as deposited with the NRRL or ATCC, or contained in the coding regions of the genes to which DNA sequences disclosed herein (in FIGS. 8, 12, 15, 18, 22A–D, 27A–D, 30A–K and 34A–D or contained in the clones, listed in Table 2, as deposited with the NRRL or ATCC, belong, for example.

In addition, differentially expressed and pathway gene products may include proteins that represent functionally equivalent gene products. Such an equivalent differentially expressed or pathway gene product may contain deletions, additions or substitutions of amino acid residues within the amino acid sequence encoded by the differentially expressed or pathway gene sequences described, above, in Section 5.4.1, but which result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous differentially expressed or pathway gene products encoded by the differentially expressed or pathway gene sequences described in Section 5.4.1, above. Alternatively, when utilized as part of assays such as those described, below, in Section 5.5, "functionally equivalent" may refer to peptides capable of interacting with other cellular or extracellular molecules in a manner substantially similar to the way in which the corresponding portion of the endogenous differentially expressed or pathway gene product would.

The differentially expressed or pathway gene products may be produced by recombinant DNA technology using techniques well known in the art. Thus, methods for preparing the differentially expressed or pathway gene polypeptides and peptides of the invention by expressing nucleic acid encoding differentially expressed or pathway gene sequences are described herein. Methods which are well known to those skilled in the art can be used to construct expression vectors containing differentially expressed or pathway gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding differentially expressed or pathway gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed or pathway gene coding sequences of the invention. Such host-expression systems represent vehicles by which the coding sequences of interest may be produced and subsequently purified, but also represent cells which may, when transformed or transfected with the appropriate nucleotide coding sequences, exhibit the differentially expressed or pathway gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed or pathway gene protein coding sequences; yeast (e.g. Saccharomyces, Pichia) transformed with recombinant yeast expression vectors containing the differentially expressed or pathway gene protein coding sequences; insect cell systems infected with recombinant virus expression vectors (e.g., baculovirus) containing the differentially expressed or pathway gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed or pathway gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the differentially expressed or pathway gene protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the differentially expressed or pathway gene protein coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In a preferred embodiment, full length cDNA sequences are appended with in-frame Bam HI sites at the amino terminus and Eco RI sites at the carboxyl terminus using standard PCR methodologies (Innis et al., 1990, supra) and ligated into the pGEX-2TK vector (Pharmacia, Uppsala, Sweden). The resulting cDNA construct contains a kinase recognition site at the amino terminus for radioactive labelling and glutathione S-transferase sequences at the carboxyl terminus for affinity purification (Nilsson, et al., 1985, EMBO J. 4: 1075; Zabeau and Stanley, 1982, EMBO J. 1: 1217.

In an insect system, *Autographa californica* nuclear polyhedrosis virus (AcNPV) is used as a vector to express foreign genes. The virus grows in *Spodoptera frugiperda* cells. The differentially expressed or pathway gene coding sequence may be cloned individually into non-essential regions (for example the polyhedrin gene) of the virus and placed under control of an AcNPV promoter (for example the polyhedrin promoter). Successful insertion of differentially expressed or pathway gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the differentially expressed or pathway gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts. (E.g., See Logan & Shenk, 1984, Proc. Natl. Acad. Sci. USA 81:3655–3659). Specific initiation signals may also be required for efficient translation of inserted differentially expressed or pathway gene coding sequences. These signals include the ATG initiation codon and adjacent sequences. In cases where an entire differentially expressed or pathway gene, including its own initiation codon and adjacent sequences, is inserted into the appropriate expression vector, no additional translational control signals may be needed. However, in cases where only a portion of the differentially expressed or pathway gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In a preferred embodiment, cDNA sequences encoding the full-length open reading frames are ligated into pCMVβ replacing the β-galactosidase gene such that cDNA expression is driven by the CMV promoter (Alam, 1990, Anal. Biochem. 188: 245–254; MacGregor & Caskey, 1989, Nucl. Acids Res. 17: 2365; Norton & Corrin, 1985, Mol. Cell. Biol. 5: 281).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed or pathway gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed or pathway gene protein. Such engineered cell lines may be particularly useful in screening and evaluation of compounds that affect the endogenous activity of the differentially expressed or pathway gene protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in $tk^-$, $hgprt^-$ or $aprt^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described, below, in Section 5.5, the differentially expressed or pathway gene protein may be labeled, either directly or indirectly, to facilitate detection of a complex formed between the differentially expressed or pathway gene protein and a test substance. Any of a variety of suitable labeling systems may be used including but not limited to radioisotopes such as $^{125}I$; enzyme labelling systems that generate a detectable colorimetric signal or light when exposed to substrate; and fluorescent labels.

Where recombinant DNA technology is used to produce the differentially expressed or pathway gene protein for such assay systems, it may be advantageous to engineer fusion proteins that can facilitate labeling, immobilization and/or detection.

Indirect labeling involves the use of a protein, such as a labeled antibody, which specifically binds to either a differentially expressed or pathway gene product. Such antibodies include but are not limited to polyclonal, monoclonal, chimeric, single chain, Fab fragments and fragments produced by an Fab expression library.

5.4.3. Differentially Expressed or Pathway Gene Product Antibodies

Described herein are methods for the production of antibodies capable of specifically recognizing one or more differentially expressed or pathway gene epitopes. Such antibodies may include, but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above. Such antibodies may be used, for example, in the detection of a fingerprint, target, or pathway gene in a biological sample, or, alternatively, as a method for the inhibition of abnormal target gene activity. Thus, such antibodies may be utilized as part of cardiovascular disease treatment methods, and/or may be used as part of diagnostic techniques whereby patients may be tested for abnormal levels of fingerprint, target, or pathway gene proteins, or for the presence of abnormal forms of the such proteins.

For the production of antibodies to a differentially expressed or pathway gene, various host animals may be immunized by injection with a differentially expressed or pathway gene protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

In a preferred embodiment, peptide sequences corresponding to amino sequences of target gene products were selected and submitted to Research Genetics (Huntsville, Ala.) for synthesis and antibody production. Peptides were modified as described (Tam, J. P., 1988, Proc. Natl. Acad. Sci. USA 85: 5409–5413; Tam, J. P., and Zavala, F., 1989, J. Immunol. Methods 124: 53–61; Tam, J. P., and Lu, Y. A., 1989, Proc. Natl. Acad. Sci. USA 86: 9084–9088), emulsified in an equal volume of Freund's adjuvant and injected into rabbits at 3 to 4 subcutaneous dorsal sites for a total volume of 1.0 ml (0.5 mg peptide) per immunization. The animals were boosted after 2 and 6 weeks and bled at weeks 4, 8, and 10. The blood was allowed to clot and serum was collected by centrifugation.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with differentially expressed or pathway gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce differentially expressed or pathway gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed (Huse et al., 1989, Science, 246:1275–1281) to allow rapid and easy identification of monoclonal Fab fragments with the desired specificity.

5.4.4. Cell- and Animal-Based Model Systems

Described herein are cell- and animal-based systems which act as models for cardiovascular disease. These systems may be used in a variety of applications. For example, the cell- and animal-based model systems may be used to further characterize differentially expressed and pathway genes, as described, above, in Section 5.3. Such further characterization may, for example, indicate that a differentially expressed gene is a target gene. Second, such assays may be utilized as part of screening strategies designed to identify compounds which are capable of ameliorating cardiovascular disease symptoms, as described, below, in Section 5.5.4. Thus, the animal- and cell-based models may be used to identify drugs, pharmaceuticals, therapies and interventions which may be effective in treating cardiovascular disease. In addition, as described in detail, below, in Section 5.7.1, such animal models may be used to determine the $LD_{50}$ and the $ED_{50}$ in animal subjects, and such data can be used to determine the in vivo efficacy of potential cardiovascular disease treatments.

5.4.4.1. Animal-Based Systems

Animal-based model systems of cardiovascular disease may include, but are not limited to, non-recombinant and engineered transgenic animals.

Non-recombinant animal models for cardiovascular disease may include, for example, genetic models. Such genetic cardiovascular disease models may include, for example, apoB or apoR deficient pigs (Rapacz, et al., 1986, Science 234:1573–1577) and Watanabe heritable hyperlipidemic (WHHL) rabbits (Kita et al., 1987, Proc. Natl. Acad. Sci USA 84: 5928–5931).

Non-recombinant, non-genetic animal models of atherosclerosis may include, for example, pig, rabbit, or rat models in which the animal has been exposed to either chemical wounding through dietary supplementation of LDL, or mechanical wounding through balloon catheter angioplasty, for example.

Additionally, animal models exhibiting cardiovascular disease symptoms may be engineered by utilizing, for example, target gene sequences such as those described, above, in Section 5.4.1, in conjunction with techniques for producing transgenic animals that are well known to those of skill in the art. For example, target gene sequences may be introduced into, and overexpressed in, the genome of the animal of interest, or, if endogenous target gene sequences are present, they may either be overexpressed or, alternatively, be disrupted in order to underexpress or inactivate target gene expression, such as described for the disruption of apoE in mice (Plump et al., 1992, Cell 71: 343–353).

In order to overexpress a target gene sequence, the coding portion of the target gene sequence may be ligated to a regulatory sequence which is capable of driving gene expression in the animal and cell type of interest. Such regulatory regions will be well known to those of skill in the art, and may be utilized in the absence of undue experimentation.

The use of such a genetically engineered animal-based system is described in detail in the example provided in Section 7, below, for the target gene bcl-2 (see Table 1, in Section 5.4.1, above). Briefly, bcl-2 expression first was shown to be down-regulated in the apoE-deficient atherosclerosis mouse model. Then, a transgenic mouse was engineered bearing the human bcl-2 gene under the control of a promoter which is induced under atherogenic conditions. To test the effect of the induction of bcl-2 under such conditions, the transgenic mouse is crossed with the apoE-deficient mouse. apoE-deficient progeny bearing the highly expressible bcl-2 gene are then examined for plaque formation and development. Reduction in plaque formation and development in these progeny confirms the effectiveness of intervening in cardiovascular disease through this target gene.

For underexpression of an endogenous target gene sequence, such a sequence may be isolated and engineered such that when reintroduced into the genome of the animal of interest, the endogenous target gene alleles will be inactivated. Preferably, the engineered target gene sequence is introduced via gene targeting such that the endogenous target sequence is disrupted upon integration of the engineered target gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, monkeys, and chimpanzees may be used to generate cardiovascular disease animal models.

Any technique known in the art may be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of the nucleotide sequence of the endogenous target gene. The transgene may also be selectively introduced into a particular cell type, thus inactivating the endogenous gene of interest in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art. Recombinant methods for expressing target genes are described in Section 5.4.2, above.

Once transgenic animals have been generated, the expression of the recombinant target gene and protein may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques which include but are not limited to Northern blot analysis of tissue samples obtained from the animal, in situ hybridization analysis, and RT-PCR. Samples of target gene-expressing tissue, may also be evaluated immunocytochemically using antibodies specific for the target gene transgene gene product of interest.

The target gene transgenic animals that express target gene mRNA or target gene transgene peptide (detected immunocytochemically, using antibodies directed against the target gene product's epitopes) at easily detectable levels should then be further evaluated to identify those animals which display characteristic cardiovascular disease symptoms. Such symptoms may include, for example, increased prevalence and size of fatty streaks and/or cardiovascular disease plaques.

Additionally, specific cell types within the transgenic animals may be analyzed and assayed for cellular phenotypes characteristic of cardiovascular disease. In the case of monocytes, such phenotypes may include but are not limited to increases in rates of LDL uptake, adhesion to endothelial cells, transmigration, foam cell formation, fatty streak formation, and production of foam cell specific products. Cellular phenotype assays are discussed in detail in Section 5.4.4.2, below. Further, such cellular phenotypes may include a particular cell type's fingerprint pattern of expression as compared to known fingerprint expression profiles of the particular cell type in animals exhibiting cardiovascular disease symptoms. Fingerprint profiles are described in detail in Section 5.8.1, below. Such transgenic animals serve as suitable model systems for cardiovascular disease.

Once target gene transgenic founder animals are produced, they may be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order both to augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target gene transgene and the development of cardiovascular disease symptoms. One such approach is to cross the target gene transgenic founder animals with a wild type strain to produce an F1 generation that exhibits cardiovascular disease symptoms. The F1 generation may then be inbred in order to develop a homozygous line, if it is found that homozygous target gene transgenic animals are viable.

5.4.4.2. Cell-Based Assays

Cells that contain and express target gene sequences which encode target gene protein, and, further, exhibit cellular phenotypes associated with cardiovascular disease, may be utilized to identify compounds that exhibit anti-cardiovascular disease activity.

Such cells may include non-recombinant monocyte cell lines, such as U937 (ATCC#CRL-1593), THP-1 (ATCC#TIB-202), and P388D1 (ATCC#TIB-63); endothelial cells such as HUVEC's and bovine aortic endothelial cells (BAEC's); as well as generic mammalian cell lines such as HeLa cells and COS cells, e.g., COS-7 (ATCC#CRL-1651). Further, such cells may include recombinant, transgenic cell lines. For example, the cardiovascular disease animal models of the invention, discussed, above, in Section 5.4.4.1, may be used to generate cell lines, containing one or more cell types involved in cardiovascular disease, that can be used as cell culture models for this disorder. While primary cultures derived from the cardiovascular disease transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

Alternatively, cells of a cell type known to be involved in cardiovascular disease may be transfected with sequences capable of increasing or decreasing the amount of target gene expression within the cell. For example, target gene sequences may be introduced into, and overexpressed in, the genome of the cell of interest, or, if endogenous target gene sequences are present, they may be either overexpressed or, alternatively disrupted in order to underexpress or inactivate target gene expression.

In order to overexpress a target gene sequence, the coding portion of the target gene sequence may be ligated to a regulatory sequence which is capable of driving gene expression in the cell type of interest. Such regulatory regions will be well known to those of skill in the art, and may be utilized in the absence of undue experimentation. Recombinant methods for expressing target genes are described in Section 5.4.2, above.

For underexpression of an endogenous target gene sequence, such a sequence may be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell's genome. Transfection of host cells with target genes is discussed, above, in Section 5.4.4.1.

Cells treated with compounds or transfected with target genes can be examined for phenotypes associated with cardiovascular disease. In the case of monocytes, such henotypes include but are not limited to increases in rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ, and GM-CSF. Transmigration rates, for example, may be measured using the in vitro system of Navab et al., described in Section 5.1.1.3, above, by quantifying the number of monocytes that migrate across the endothelial monolayer and into the collagen layer of the subendothelial space.

Similarly, HUVEC's can be treated with test compounds or transfected with genetically engineered target genes described in Section 5.4.2, above. The HUVEC's can then be examined for phenotypes associated with cardiovascular disease, including, but not limited to changes in cellular morphology, cell proliferation, cell migration, and mononuclear cell adhesion; or for the effects on production of other proteins involved in cardiovascular disease such as ICAM, VCAM, PDGF-β, and E-selectin.

Transfection of target gene sequence nucleic acid may be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production. In instances wherein a decrease in target gene expression is desired, standard techniques may be used to demonstrate whether a decrease in endogenous target gene expression and/or in target gene product production is achieved.

5.5. Screening Assays for Compounds That Interact with the Target Gene Product

The following assays are designed to identify compounds that bind to target gene products, bind to other cellular or extracellular proteins that interact with a target gene product, and interfere with the interaction of the target gene product with other cellular or extracellular proteins. For example, in the case of the rchd523 gene product, which is a transmembrane receptor-type protein, such techniques can identify ligands for such a receptor. An rchd523 gene product ligand can, for example, act as the basis for amelioration of such cardiovascular diseases as atherosclerosis, ischemia/reperfusion, hypertension, restenosis, and arterial inflammation, given that rchd523 up-regulation is specific to endothelial cells. Such compounds may include, but are not limited to peptides, antibodies, or small organic or inorganic compounds. Methods for the identification of such compounds are described in Section 5.5.1, below. Such compounds may also include other cellular proteins. Methods for the identification of such cellular proteins are described, below, in Section 5.5.2.

Compounds identified via assays such as those described herein may be useful, for example, in elaborating the biological function of the target gene product, and for ameliorating cardiovascular disease. In instances whereby a cardiovascular disease condition results from an overall lower level of target gene expression and/or target gene product in a cell or tissue, compounds that interact with the target gene product may include compounds which accentuate or amplify the activity of the bound target gene protein. Such compounds would bring about an effective increase in the level of target gene product activity, thus ameliorating symptoms.

In some cases, a target gene observed to be up-regulated under disease conditions may be exerting a protective effect. Compounds that enhance the expression of such up-regulated genes, or the activity of their gene products, would also ameliorate disease symptoms, especially in individuals whose target gene is not normally up-regulated.

In other instances mutations within the target gene may cause aberrant types or excessive amounts of target gene proteins to be made which have a deleterious effect that leads to cardiovascular disease. Similarly, physiological conditions may cause an excessive increase in target gene expression leading to cardiovascular disease. In such cases, compounds that bind target gene protein may be identified that inhibit the activity of the bound target gene protein. Assays for testing the effectiveness of compounds, identified by, for example, techniques such as those described in this Section are discussed, below, in Section 5.5.4.

5.5.1. In Vitro Screening Assays for Compounds That Bind to the Target Gene Product In vitro systems may be designed to identify compounds capable of binding the target gene of the invention. Such compounds may include, but are not limited to, peptides made of D-and/or L-configuration amino acids (in, for example, the form of random peptide libraries; see e.g., Lam, K. S. et al., 1991, Nature 354:82–84), phosphopeptides (in, for example, the form of random or partially degenerate, directed phosphopeptide libraries; see, e.g., Songyang, Z. et al., 1993, Cell 72:767–778), antibodies, and small organic or inorganic molecules. Compounds identified may be useful, for example, in modulating the activity of target gene proteins, preferably mutant target gene proteins, may be useful in elaborating the biological function of the target gene protein, may be utilized in screens for identifying compounds that disrupt normal target gene interactions, or may in themselves disrupt such interactions.

The principle of the assays used to identify compounds that bind to the target gene protein involves preparing a reaction mixture of the target gene protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring the target gene or the test substance onto a solid phase and detecting target gene/test substance complexes anchored on the solid phase at the end of the reaction. In one embodiment of such a method, the target gene protein may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

Compounds that are shown to bind to a particular target gene product through one of the methods described above can be further tested for their ability to elicit a biochemical response from the target gene protein. A particular embodiment is described herein for receptor proteins involved in signal transduction, including but not limited to the rchd523 gene product. Compounds that interact with a target gene product receptor domain, can be screened for their ability to function as ligands, i.e., to bind to the receptor protein in a manner that triggers the signal transduction pathway. Useful receptor fragments or analogs in the invention are those which interact with ligand. The receptor component can be assayed functionally, i.e., for its ability to bind ligand and mobilize $Ca^{++}$ (see below). These assays include, as components, ligand and a recombinant target gene product (or a suitable fragment or analog) configured to permit detection of binding.

For example, and not by way of limitation, a recombinant receptor may be used to screen for ligands by its ability to mediate ligand-dependent mobilization of calcium. Cells, preferably myeloma cells or Xenopus oocytes, transfected with a target gene expression vector (constructed according to the methods described in Section 5.4.2, above) are loaded with FURA-2 or INDO-1 by standard techniques. Mobilization of $Ca^{2+}$ induced by ligand is measured by fluorescence spectroscopy as previously described (Grynkiewicz et al., 1985, *J. Biol. Chem.* 260:3440). Ligands that react with the target gene product receptor domain, therefore, can be identified by their ability to produce a fluorescent signal. Their receptor binding activities can be quantified and compared by measuring the level of fluorescence produced over background.

The rchd523 gene product consists of a G protein-coupled receptor with multiple transmembrane domains. The $Ca^{2+}$ mobilization assay, therefore, can be used to screen compounds that are ligands of the rchd523 receptor. This screening method is described in detail with respect to rchd523 in the example in Section 12, below. Identification of rchd523 ligand, and measuring the activity of the ligand-receptor complex, leads to the identification of antagonists of this interaction, as described in Section 5.5.3, below.

Such antagonists are useful in the treatment of cardiovascular disease.

5.5.2. Assays for Cellular or Extracellular Proteins That Interact with the Target Gene Product Any method suitable for detecting protein-protein interactions may be employed for identifying novel target protein-cellular or extracellular protein interactions. These methods are outlined in Section 5.2., supra, for the identification of pathway genes, and may be utilized herein with respect to the identification of proteins which interact with identified target proteins. In such a case, the target-gene serves as the known "bait" gene.

5.5.3. Assays for Compounds That Interfere with Interaction between Target Gene Product and Other Compounds The target gene proteins of the invention may, in vivo, interact with one or more cellular or extracellular proteins. Such proteins may include, but are not limited to, those proteins identified via methods such as those described, above, in Section 5.5.2. For the purposes of this discussion, target gene products and such cellular and extracellular proteins are referred to herein as "binding partners". Compounds that disrupt such interactions may be useful in regulating the activity of the target gene proteins, especially mutant target gene proteins. Such compounds may include, but are not limited to molecules such as antibodies, peptides, and the like described in Section 5.5.1. above.

The basic principle of the assay systems used to identify compounds that interfere with the interaction between the target gene protein, and its cellular or extracellular protein binding partner or partners involves preparing a reaction mixture containing the target gene protein and the binding partner under conditions and for a time sufficient to allow the two proteins to interact and bind, thus forming a complex. In order to test a compound for inhibitory activity, the reaction mixture is prepared in the presence and absence of the test compound. The test compound may be initially included in the reaction mixture or may be added at a time subsequent to the addition of target gene and its cellular or extracellular binding partner. Control reaction mixtures are incubated without the test compound or with a placebo. The formation of any complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner protein. Additionally, complex formation within reaction mixtures containing the test compound and a normal target gene protein may also be compared to complex formation within reaction mixtures containing the test compound and mutant target gene protein. This comparison may be important in those cases wherein it is desirable to identify compounds that disrupt interactions of mutant but not normal target gene proteins.

The assay for compounds that interfere with the interaction of the binding partners can be conducted in a heterogeneous or homogeneous format. Heterogeneous assays involve anchoring one of the binding partners onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the binding partners, e.g., by competition, can be identified by conducting the reaction in the presence of the test substance; i.e., by adding the test substance to the reaction mixture prior to or simultaneously with the target gene protein and interactive cellular or extracellular protein. Alternatively, test compounds that disrupt preformed complexes, e.g. compounds with higher binding constants that displace one of the binding partners from the complex, can be tested by adding the test compound to the reaction mixture after complexes have been formed. The various formats are described briefly below.

In a heterogeneous assay system, either the target gene protein or the interactive cellular or extracellular binding partner protein, is anchored onto a solid surface, and its binding partner, which is not anchored, is labeled, either directly or indirectly. In practice, microtitre plates are conveniently utilized. The anchored species may be immobilized by non-covalent or covalent attachments. Non-covalent attachment may be accomplished simply by coating the solid surface with a solution of the protein and drying. Alternatively, an immobilized antibody specific for the protein may be used to anchor the protein to the solid surface. The surfaces may be prepared in advance and stored.

In order to conduct the assay, the binding partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one binding partner to anchor any complexes formed in solution, and a labeled antibody specific for the other binding partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene protein and the interactive cellular or extracellular protein is prepared in which one of the binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the binding partners from the preformed complex will result in the generation of a signal above background. In this way, test substances which disrupt target gene protein-cellular or extracellular protein interaction can be identified.

In a particular embodiment, the target gene protein can be prepared for immobilization using recombinant DNA techniques described in Section 5.4.2, supra. For example, the target gene coding region can be fused to a glutathione-S-transferase (GST) gene, using a fusion vector such as pGEX-5X-1, in such a manner that its binding activity is maintained in the resulting fusion protein. The interactive cellular or extracellular protein can be purified and used to raise a monoclonal antibody, using methods routinely practiced in the art and described above, in Section 5.4.3. This antibody can be labeled with the radioactive isotope $^{125}I$, for example, by methods routinely practiced in the art. In a heterogeneous assay, e.g., the GST-target gene fusion protein can be anchored to glutathione-agarose beads. The interactive cellular or extracellular binding partner protein can then be added in the presence or absence of the test compound in a manner that allows interaction and binding to occur. At the end of the reaction period, unbound material can be washed away, and the labeled monoclonal antibody can be added to the system and allowed to bind to the complexed binding partners. The interaction between the target gene protein and the interactive cellular or extracellular binding partner protein can be detected by measuring the amount of radioactivity that remains associated with the glutathione-agarose beads. A successful inhibition of the interaction by the test compound will result in a decrease in measured radioactivity.

Alternatively, the GST-target gene fusion protein and the interactive cellular or extracellular binding partner protein can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the target gene protein and the interactive cellular or extracellular protein, respectively, in place of one or both of the full length proteins. Any number of methods routinely practiced in the art can be used to identify and isolate the protein's binding site. These methods include, but are not limited to, mutagenesis of one of the genes encoding the proteins and screening for disruption of binding in a co-immunoprecipitation assay. Compensating mutations in the target gene can be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the for the cellular or extracellular protein is obtained, short gene segments can be engineered to express peptide fragments of the protein, which can then be tested for binding activity and purified or synthesized.

For example, and not by way of limitation, target gene can be anchored to a solid material as described above in this Section by making a GST-target gene fusion protein and allowing it to bind to glutathione agarose beads. The interactive cellular or extracellular binding partner protein can be labeled with a radioactive isotope, such as $^{35}S$, and cleaved with a proteolytic enzyme such as trypsin. Cleavage products can then be added to the anchored GST-target gene fusion protein and allowed to bind. After washing away unbound peptides, labeled bound material, representing the cellular or extracellular binding partner protein binding domain, can be eluted, purified, and analyzed for amino acid sequence by techniques well known in the art; e.g., using the Edman degradation procedure (see e.g., Creighton, 1983, Proteins: Structures and Molecular Principles, W. H. Freeman & Co., N.Y., pp. 34–49). Peptides so identified can be produced, using techniques well known in the art, either synthetically (see e.g., Creighton, 1983, supra at pp. 50–60) or, if the gene has already been isolated, by using recombinant DNA technology, as described in Section 5.4.2, supra.

A particular embodiment of the invention features a method of screening candidate compounds for their ability to antagonize the interaction between ligand and the receptor domain of a target gene product, including but not limited to the receptor domain of the rchd523 gene product. The rchd523 gene product, which is a G protein-coupled receptor protein containing multiple transmembrane domains, is especially useful in screening for antagonists of ligand-receptor interactions. The method involves: a) mixing a candidate antagonist compound with a first compound which includes a recombinant target gene product comprising a receptor domain (or ligand-binding fragment or analog) on the one hand and with a second compound which includes ligand on the other hand; b) determining whether the first and second compounds bind; and c) identifying antagonistic compounds as those which interfere with the binding of the first compound to the second compound and/or which reduce the ligand-mediated release of intracellular $Ca^{++}$.

By an "antagonist" is meant a molecule which inhibits a particular activity, in this case, the ability of ligand to interact with a target gene product receptor domain and/or to trigger the biological events resulting from such an interaction (e.g., release of intracellular $Ca^{++}$). Preferred therapeutics include antagonists, e.g., peptide fragments (particularly, fragments derived from the N-terminal extracellular domain), antibodies (particularly, antibodies which recognize and bind the N-terminal extracellular domain), or drugs, which block ligand or target gene product function by interfering with the ligand-receptor interaction.

Because the receptor component of the target gene product can be produced by recombinant techniques and because candidate antagonists may be screened in vitro, the instant invention provides a simple and rapid approach to the identification of useful therapeutics.

Specific receptor fragments of interest include any portions of the target gene products that are capable of interaction with ligand, for example, all or part of the N-terminal extracellular domain. Such portions include the transmembrane segments and portions of the receptor deduced to be extracellular. Such fragments may be useful as antagonists (as described above), and are also useful as immunogens for producing antibodies which neutralize the activity of the target gene product in vivo (e.g., by interfering with the interaction between the receptor and ligand; see below).

Extracellular regions may be identified by comparison with related proteins of similar structure (e.g., other members of the G-protein-coupled receptor superfamily); useful regions are those exhibiting homology to the extracellular domains of well-characterized members of the family.

Alternatively, from the primary amino acid sequence, the secondary protein structure and, therefore, the extracellular domain regions may be deduced semi-empirically using a hydrophobicity/hydrophilicity calculation such as the Chou-Fasman method (see, e.g., Chou and Fasman, *Ann. Rev. Biochem.* 47:251, 1978). Hydrophilic domains, particularly ones surrounded by hydrophobic stretches (e.g., transmembrane domains) present themselves as strong candidates for extracellular domains. Finally, extracellular domains may be identified experimentally using standard enzymatic digest analysis, e.g., tryptic digest analysis.

Candidate fragments (e.g., all or part of the transmembrane segments or any extracellular fragment) are tested for interaction with ligand by the assays described herein (e.g., the assay described above). Such fragments are also tested for their ability to antagonize the interaction between ligand and its endogenous receptor using the assays described herein. Analogs of useful receptor fragments (as described above) may also be produced and tested for efficacy as screening components or antagonists (using the assays described herein); such analogs are also considered to be useful in the invention.

Of particular interest are receptor fragments encompassing the extracellular main-terminal domain (or a 1ligand binding fragment thereof). Also of interest are the target gene product extracellular loops. Peptide fragments derived from these extracellular loops may also be used as antagonists, particularly if the loops cooperate with the amino-terminal domain to facilitate ligand binding. Alternatively, such loops and extracellular N-terminal domain (as well as the full length target gene product) provide immunogens for producing anti-target gene product antibodies.

Binding of ligand to its receptor may be assayed by any of the methods described above in Section 5.5.1. Preferably, cells expressing recombinant target gene product (or a suitable target gene product fragment or analog) are immobilized on a solid substrate (e.g., the wall of a microtitre plate or a column) and reacted with detectably-labelled ligand (as described above). Binding is assayed by the detection label in association with the receptor component (and, therefore, in association with the solid substrate). Binding of labelled ligand to receptor-bearing cells is used as a "control" against which antagonist assays are measured. The antagonist assays involve incubation of the target gene product-bearing cells with an appropriate amount of candidate antagonist. To this mix, an equivalent amount to labelled ligand is added. An antagonist useful in the invention specifically interferes with labelled ligand binding to the immobilized receptor-expressing cells.

An antagonist is then tested for its ability to interfere with ligand function, i.e., to specifically interfere with labelled ligand binding without resulting in signal transduction normally mediated by the receptor. To test this using a functional assay, stably transfected cell lines containing the target gene product can be produced as described herein and reporter compounds such as the calcium binding agent, FURA-2, loaded into the cytoplasm by standard techniques. Stimulation of the heterologous target gene product with ligand or another agonist leads to intracellular calcium release and the concomitant fluorescence of the calcium-FURA-2 complex. This provides a convenient means for measuring agonist activity. Inclusion of potential antagonists along with ligand allows for the screening and identification of authentic receptor antagonists as those which effectively block ligand binding without producing fluorescence (i.e., without causing the mobilization of intracellular $Ca^{++}$). Such an antagonist may be expected to be a useful therapeutic agent for cardiovascular disorders.

Appropriate candidate antagonists include target gene product fragments, particularly fragments containing a ligand-binding portion adjacent to or including one or more transmembrane segments or an extracellular domain of the receptor (described above); such fragments would preferably including five or more amino acids. Other candidate antagonists include analogs of ligand and other peptides as well as non-peptide compounds and anti-target gene product antibodies designed or derived from analysis of the receptor.

This screening method is described in detail with respect to the rchd523 gene in the example in Section 12, below. Because the rchd523 gene product is a G protein-coupled receptor, antagonists of the interaction between the rchd523 gene product and its natural ligand provide excellent candidates for compounds effective in the treatment of cardiovascular disease.

5.5.4. Assays for Amelioration of Cardiovascular Disease Symptoms

Any of the binding compounds, including but not limited to compounds such as those identified in the foregoing assay systems, may be tested for the ability to ameliorate cardiovascular disease symptoms. Cell-based and animal model-based assays for the identification of compounds exhibiting such an ability to ameliorate cardiovascular disease symptoms are described below.

First, cell-based systems such as those described, above, in Section 5.4.4.2., may be used to identify compounds which may act to ameliorate cardiovascular disease symptoms. For example, such cell systems may be exposed to a compound, suspected of exhibiting an ability to ameliorate cardiovascular disease symptoms, at a sufficient concentration and for a time sufficient to elicit such an amelioration of cardiovascular disease symptoms in the exposed cells. After exposure, the cells are examined to determine whether one or more of the cardiovascular disease cellular phenotypes has been altered to resemble a more normal or more wild type, non-cardiovascular disease phenotype. For example, and not by way of limitation, in the case of monocytes, such more normal phenotypes may include but are not limited to decreased rates of LDL uptake, adhesion to endothelial cells, transmigration, foam cell formation, fatty streak formation, and production by foam cells of growth factors such as bFGF, IGF-I, VEGF, IL-1, M-CSF, TGFβ, TGFα, TNFα, HB-EGF, PDGF, IFN-γ, and GM-CSF. Transmigration rates, for example, may be measured using the in vitro system of Navab et al., described in Section 5.1.1.3, above, by quantifying the number of monocytes that migrate across the endothelial monolayer and into the collagen layer of the subendothelial space.

In addition, animal-based cardiovascular disease systems, such as those described, above, in Section 5.4.4.1, may be used to identify compounds capable of ameliorating cardiovascular disease symptoms. Such animal models may be used as test substrates for the identification of drugs, pharmaceuticals, therapies, and interventions which may be effective in treating cardiovascular disease. For example, animal models may be exposed to a compound, suspected of exhibiting an ability to ameliorate cardiovascular disease symptoms, at a sufficient concentration and for a time sufficient to elicit such an amelioration of cardiovascular disease symptoms in the exposed animals. The response of the animals to the exposure may be monitored by assessing the reversal of disorders associated with cardiovascular disease, for example, by counting the number of atherosclerotic plaques and/or measuring their size before and after treatment.

With regard to intervention, any treatments which reverse any aspect of cardiovascular disease symptoms should be considered as candidates for human cardiovascular disease therapeutic intervention. Dosages of test agents may be determined by deriving dose-response curves, as discussed in Section 5.7.1, below.

Additionally, gene expression patterns may be utilized to assess the ability of a compound to ameliorate cardiovascular disease symptoms. For example, the expression pattern of one or more fingerprint genes may form part of a "fingerprint profile" which may be then be used in such an assessment. "Fingerprint profile", as used herein, refers to the pattern of mRNA expression obtained for a given tissue or cell type under a given set of conditions. Such conditions may include, but are not limited to, atherosclerosis, ischemia/reperfusion, hypertension, restenosis, and arterial inflammation, including any of the control or experimental conditions described in the paradigms of Section 5.1.1, above. Fingerprint profiles may be generated, for example, by utilizing a differential display procedure, as discussed, above, in Section 5.1.2, Northern analysis and/or RT-PCR. Any of the gene sequences described, above, in Section 5.4.1. may be used as probes and/or PCR primers for the generation and corroboration of such fingerprint profiles.

Fingerprint profiles may be characterized for known states, either cardiovascular disease or normal, within the cell- and/or animal-based model systems. Subsequently, these known fingerprint profiles may be compared to ascertain the effect a test compound has to modify such fingerprint profiles, and to cause the profile to more closely resemble that of a more desirable fingerprint.

For example, administration of a compound may cause the fingerprint profile of a cardiovascular disease model system to more closely resemble the control system. Administration of a compound may, alternatively, cause the fingerprint profile of a control system to begin to mimic a cardiovascular disease state. Such a compound may, for example, be used in further characterizing the compound of interest, or may be used in the generation of additional animal models.

5.5.5. Monitoring of Effects during Clinical Trials

Monitoring the influence of compounds on cardiovascular disease states may be applied not only in basic drug screening, but also in clinical trials. In such clinical trials, the expression of a panel of genes that have been discovered in one of the paradigms described in Section 5.1.1.1 through 5.1.1.6 may be used as a "read out" of a particular drug's effect on a cardiovascular disease state.

For example, and not by way of limitation, Paradigm A provides for the identification of fingerprint genes that are up-regulated in monocytes treated with oxidized LDL. Thus, to study the effect of anti-oxidant drugs, for example, in a clinical trial, blood may be drawn from patients before and at different stages during treatment with such a drug. Their monocytes may then be isolated and RNA prepared and analyzed by differential display as described in Sections 6.1.1 and 6.1.2. The levels of expression of these fingerprint genes may be quantified by Northern blot analysis or RT-PCR, as described in Section 6.1.2, or by one of the methods described in Section 5.8.1, or alternatively by measuring the amount of protein produced, by one of the methods described in Section 5.8.2. In this way, the fingerprint profiles may serve as surrogate markers indicative of the physiological response of monocytes that have taken up oxidized LDL. Accordingly, this response state may be determined before, and at various points during, drug treatment. This method is described in further detail in the example in Section 10, below.

This method may also be applied to the other paradigms disclosed herein. For example, and not by way of limitation, the fingerprint profile of Paradigm B reveals that bcl-2 and glutathione peroxidase are both down-regulated in the monocytes of patients exposed to a high lipid diet, e.g. cholesterol or fat, that leads to high serum LDL levels. Drugs may be tested, for example, for their ability to ameliorate the effects of hypercholesterolemia in clinical trials. Patients with high LDL levels may have their monocytes isolated before, and at different stages after, drug treatment. The drug's efficacy may be measured by determining the degree of restored expression of bcl-2 and glutathione peroxidase, as described above for the Paradigm A fingerprint profile.

5.6. Compounds and Methods for Treatment of Cardiovascular Disease

Described below are methods and compositions whereby cardiovascular disease symptoms may be ameliorated. Certain cardiovascular diseases are brought about, at least in part, by an excessive level of gene product, or by the presence of a gene product exhibiting an abnormal or excessive activity. As such, the reduction in the level and/or activity of such gene products would bring about the amelioration of cardiovascular disease symptoms. Techniques for the reduction of target gene expression levels or target gene product activity levels are discussed in Section 5.6.1, below.

Alternatively, certain other cardiovascular diseases are brought about, at least in part, by the absence or reduction of the level of gene expression, or a reduction in the level of a gene product's activity. As such, an increase in the level of gene expression and/or the activity of such gene products would bring about the amelioration of cardiovascular disease symptoms.

In some cases, the up-regulation of a gene in a disease state reflects a protective role for that gene product in responding to the disease condition. Enhancement of such a target gene's expression, or the activity of the target gene product, will reinforce the protective effect it exerts. Some cardiovascular disease states may result from an abnormally low level of activity of such a protective gene. In these cases also, an increase in the level of gene expression and/or the activity of such gene products would bring about the amelioration of cardiovascular disease symptoms. Techniques for increasing target gene expression levels or target gene product activity levels are discussed in Section 5.6.2, below.

5.6.1. Compounds That Inhibit Expression, Synthesis or Activity of Mutant Target Gene Activity As discussed above, target genes involved in cardiovascular disease disorders can cause such disorders via an increased level of target gene activity. As summarized in Table 1, above, and detailed in the examples in Sections 8 and 9, below, a number of genes are now known to be up-regulated in endothelial cells under disease conditions. Specifically, rchd005, rchd024, rchd032, and rchd036 are all up-regulated in endothelial cells treated with IL-1. Furthermore, rchd502, rchd523, rchd528, rchd534, COX II, and MnSOD are all up-regulated in endothelial cells subjected to shear stress. In some cases, such up-regulation may have a causative or exacerbating effect on the disease state.

A variety of techniques may be utilized to inhibit the expression, synthesis, or activity of such target genes and/or proteins.

For example, compounds such as those identified through assays described, above, in Section 5.5, which exhibit inhibitory activity, may be used in accordance with the invention to ameliorate cardiovascular disease symptoms. As discussed in Section 5.5, above, such molecules may include, but are not limited to small organic molecules, peptides, antibodies, and the like. Inhibitory antibody techniques are described, below, in Section 5.6.1.2.

For example, compounds can be administered that compete with endogenous ligand for the rchd523 gene product. The resulting reduction in the amount of ligand-bound rchd523 gene transmembrane protein will modulated endothelial cell physiology. Compounds that can be particularly useful for this purpose include, for example, soluble proteins or peptides, such as peptides comprising one or more of the extracellular domains, or portions and/or analogs thereof, of the rchd523 gene product, including, for example, soluble fusion proteins such as Ig-tailed fusion proteins. (For a discussion of the production of Ig-tailed fusion proteins, see, for example, U.S. Pat. No. 5,116,964.). Alternatively, compounds, such as ligand analogs or antibodies, that bind to the rchd523 gene product receptor site, but do not activate the protein, (e.g., receptor-ligand antagonists) can be effective in inhibiting rchd523 gene product activity.

Further, antisense and ribozyme molecules which inhibit expression of the target gene may also be used in accordance with the invention to inhibit the aberrant target gene activity. Such techniques are described, below, in Section 5.6.1.1. Still further, also as described, below, in Section 5.6.1.1, triple helix molecules may be utilized in inhibiting the aberrant target gene activity.

5.6.1.1. Inhibitory Antisense, Ribozyme and Triple Helix Approaches

Among the compounds which may exhibit the ability to ameliorate cardiovascular disease symptoms are antisense, ribozyme, and triple helix molecules. Such molecules may be designed to reduce or inhibit mutant target gene activity. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and $CGC^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC paris, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant target gene alleles. In order to ensure that substantially normal levels of target gene activity are maintained, nucleic acid molecules that encode and express target gene polypeptides exhibiting normal activity may be introduced into cells via gene therapy methods such as those described, below, in Section 5.7. that do not contain sequences susceptible to whatever antisense, ribozyme, or triple helix treatments are being utilized. Alternatively, it may be preferable to coadminister normal target gene protein into the cell or tissue in order to maintain the requisite level of cellular or tissue target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

5.6.1.2. Antibodies for Target Gene Products

Antibodies that are both specific for target gene protein and interfere with its activity may be used to inhibit target gene function. Such antibodies may be generated using standard techniques described in Section 5.4.3., supra, against the proteins themselves or against peptides corresponding to portions of the proteins. Such antibodies include but are not limited to polyclonal, monoclonal, Fab fragments, single chain antibodies, chimeric antibodies, etc.

In instances where the target gene protein is intracellular and whole antibodies are used, internalizing antibodies may be preferred. However, lipofectin liposomes may be used to deliver the antibody or a fragment of the Fab region which binds to the target gene epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein may be used. Such peptides may be synthesized chemically or produced via recombinant DNA technology using methods well known in the art (e.g., see Creighton, 1983, supra; and Sambrook et al., 1989, supra). Alternatively, single chain neutralizing antibodies which bind to intracellular target gene epitopes may also be administered. Such single chain antibodies may be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. USA 90:7889–7893).

In some instances, the target gene protein is extracellular, or is a transmembrane protein, such as the rchd523 gene product. Antibodies that are specific for one or more extracellular domains of the rchd523 gene product, for example, and that interfere with its activity, are particularly useful in treating cardiovascular disease. Such antibodies are especially efficient because they can access the target domains directly from the bloodstream. Any of the administration techniques described, below in Section 5.7 which are appropriate for peptide administration may be utilized to effectively administer inhibitory target gene antibodies to their site of action.

5.6.2. Methods for Restoring or Enhancing Target Gene Activity

Target genes that cause cardiovascular disease may be underexpressed within cardiovascular disease situations. As summarized in Table 1, above, and detailed in the example in Sections 7, below, several genes are now known to be down-regulated in monocytes under disease conditions. Specifically, bcl-2 and glutathione peroxidase gene expression is down-regulated in the monocytes of patients exposed to a high lipid diet, e.g. cholesterol or fat, that leads to high serum LDL levels. Alternatively, the activity of target gene products may be decreased, leading to the development of cardiovascular disease symptoms. Such down-regulation of target gene expression or decrease of target gene product activity might have a causative or exacerbating effect on the disease state.

In some cases, target genes that are up-regulated in the disease state might be exerting a protective effect. As summarized in Table 1, above, and detailed in the examples in Sections 8 and 9, below, a number of genes are now known to be up-regulated in endothelial cells under disease conditions. Specifically, rchd005, rchd024, rchd032, and rchd036 are all up-regulated in endothelial cells treated with IL-1. Furthermore, rchd502, rchd523, rchd528, rchd534, COX II, and MnSOD are all up-regulated in endothelial cells subjected to shear stress. A variety of techniques may be utilized to increase the expression, synthesis, or activity of such target genes and/or proteins, for those genes that exert a protective effect in response to disease conditions.

Described in this Section are methods whereby the level of target gene activity may be increased to levels wherein cardiovascular disease symptoms are ameliorated. The level of gene activity may be increased, for example, by either increasing the level of target gene product present or by increasing the level of active target gene product which is present.

For example, a target gene protein, at a level sufficient to ameliorate cardiovascular disease symptoms may be administered to a patient exhibiting such symptoms. Any of the techniques discussed, below, in Section 5.7, may be utilized for such administration. One of skill in the art will readily know how to determine the concentration of effective, non-toxic doses of the normal target gene protein, utilizing techniques such as those described, below, in Section 5.7.1.

Additionally, RNA sequences encoding target gene protein may be directly administered to a patient exhibiting cardiovascular disease symptoms, at a concentration sufficient to produce a level of target gene protein such that cardiovascular disease symptoms are ameliorated. Any of the techniques discussed, below, in Section 5.7, which achieve intracellular administration of compounds, such as, for example, liposome administration, may be utilized for the administration of such RNA molecules. The RNA molecules may be produced, for example, by recombinant techniques such as those described, above, in Section 5.4.2.

Further, patients may be treated by gene replacement therapy. One or more copies of a normal target gene, or a portion of the gene that directs the production of a normal target gene protein with target gene function, may be inserted into cells using vectors which include, but are not limited to adenovirus, adeno-associated virus, and retrovirus vectors, in addition to other particles that introduce DNA into cells, such as liposomes. Additionally, techniques such as those described above may be utilized for the introduction of normal target gene sequences into human cells.

Cells, preferably, autologous cells, containing normal target gene expressing gene sequences may then be introduced or reintroduced into the patient at positions which allow for the amelioration of cardiovascular disease symptoms. Such cell replacement techniques may be preferred, for example, when the target gene product is a secreted, extracellular gene product.

5.7. PHARMACEUTICAL PREPARATIONS AND METHODS OF ADMINISTRATION

The identified compounds that inhibit target gene expression, synthesis and/or activity can be administered to a patient at therapeutically effective doses to treat or ameliorate cardiovascular disease. A therapeutically effective dose refers to that amount of the compound sufficient to result in amelioration of symptoms of cardiovascular disease.

5.7.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

5.7.2. Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

5.8. DIAGNOSIS OF CARDIOVASCULAR DISEASE ABNORMALITIES

A variety of methods may be employed, utilizing reagents such as fingerprint gene nucleotide sequences described in Section 5.4.1, and antibodies directed against differentially expressed and pathway gene peptides, as described, above, in Sections 5.4.2. (peptides) and 5.4.3 . (antibodies). Specifically, such reagents may be used, for example, for the detection of the presence of target gene mutations, or the detection of either over or under expression of target gene mRNA.

The methods described herein may be performed, for example, by utilizing pre-packaged diagnostic kits comprising at least one specific fingerprint gene nucleic acid or anti-fingerprint gene antibody reagent described herein, which may be conveniently used, e.g., in clinical settings, to diagnose patients exhibiting cardiovascular disease symptoms or at risk for developing cardiovascular disease.

Any cell type or tissue, preferably monocytes, endothelial cells, or smooth muscle cells, in which the fingerprint gene is expressed may be utilized in the diagnostics described below.

5.8.1. Detection of Fingerprint Gene Nucleic Acids

DNA or RNA from the cell type or tissue to be analyzed may easily be isolated using procedures which are well known to those in the art. Diagnostic procedures may also be performed "in situ" directly upon tissue sections (fixed and/or frozen) of patient tissue obtained from biopsies or resections, such that no nucleic acid purification is necessary. Nucleic acid reagents such as those described in Section 5.1. may be used as probes and/or primers for such in situ procedures (see, for example, Nuovo, G. J., 1992, PCR in situ hybridization: protocols and applications, Raven Press, NY).

Fingerprint gene nucleotide sequences, either RNA or DNA, may, for example, be used in hybridization or amplification assays of biological samples to detect cardiovascular disease-related gene structures and expression. Such assays may include, but are not limited to, Southern or Northern analyses, single stranded conformational polymorphism analyses, in situ hybridization assays, and polymerase chain reaction analyses. Such analyses may reveal both quantitative aspects of the expression pattern of the fingerprint gene, and qualitative aspects of the fingerprint gene expression and/or gene composition. That is, such aspects may include, for example, point mutations, insertions, deletions, chromosomal rearrangements, and/or activation or inactivation of gene expression.

Such an in situ hybridization analysis is described in the example in Section 14, below. Specifically, high levels of expression of the rchd502 and rchd528 genes were detected specifically within the endothelial cells of diseased tissue removed from a human cardiovascular disease patient, and not in any other cell type present in the tissue, including smooth muscle cells and macrophages. These results clearly demonstrate how the target genes described herein provide for novel diagnoses of cardiovascular disease. Furthermore, because these diagnoses are correlated with specific target genes, they allow for more specifically directed methods of treatment of cardiovascular disease.

Preferred diagnostic methods for the detection of fingerprint gene-specific nucleic acid molecules may involve for example, contacting and incubating nucleic acids, derived from the cell type or tissue being analyzed, with one or more labeled nucleic acid reagents as are described in Section 5.1, under conditions favorable for the specific annealing of these reagents to their complementary sequences within the nucleic acid molecule of interest. Preferably, the lengths of these nucleic acid reagents are at least 9 to 30 nucleotides. After incubation, all non-annealed nucleic acids are removed from the nucleic acid:fingerprint molecule hybrid. The presence of nucleic acids from the fingerprint tissue which have hybridized, if any such molecules exist, is then detected. Using such a detection scheme, the nucleic acid from the tissue or cell type of interest may be immobilized, for example, to a solid support such as a membrane, or a plastic surface such as that on a microtitre plate or polystyrene beads. In this case, after incubation, non-annealed, labeled fingerprint nucleic acid reagents of the type described in Section 5.1. are easily removed. Detection of the remaining, annealed, labeled nucleic acid reagents is accomplished using standard techniques well-known to those in the art.

Alternative diagnostic methods for the detection of fingerprint gene specific nucleic acid molecules may involve their amplification, e.g., by PCR (the experimental embodiment set forth in Mullis, K. B., 1987, U.S. Pat. No. 4,683,202), ligase chain reaction (Barany, F., 1991, Proc. Natl. Acad. Sci. USA 88:189–193), self sustained sequence replication (Guatelli, J. C. et al., 1990, Proc. Natl. Acad. Sci. USA 87:1874–1878), transcriptional amplification system (Kwoh, D. Y et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild type fingerprint gene is known to be expressed, including, but not limited, to monocytes, endothelium, and/or smooth muscle. A fingerprint sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the fingerprint gene nucleic acid reagents described in Section 5.1. The preferred lengths of such nucleic acid reagents are at least 15–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

In addition to methods which focus primarily on the detection of one nucleic acid sequence, fingerprint profiles, as discussed in Section 5.5.4, may also be assessed in such detection schemes. Fingerprint profiles may be generated, for example, by utilizing a differential display procedure, as discussed, above, in Section 5.1.2, Northern analysis and/or RT-PCR. Any of the gene sequences described, above, in Section 5.4.1. may be used as probes and/or PCR primers for the generation and corroboration of such fingerprint profiles.

5.8.2. Detection of Fingerprint Gene Peptides

Antibodies directed against wild type or mutant fingerprint gene peptides, which are discussed, above, in Section 5.4.3, may also be used as cardiovascular disease diagnostics and prognostics, as described, for example, herein. Such diagnostic methods, may be used to detect abnormalities in the level of fingerprint gene protein expression, or abnormalities in the structure and/or tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be detected or isolated using techniques which are well known to those of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Preferred diagnostic methods for the detection of wild type or mutant fingerprint gene peptide molecules may involve, for example, immunoassays wherein fingerprint gene peptides are detected by their interaction with an anti-fingerprint gene specific peptide antibody.

For example, antibodies, or fragments of antibodies, such as those described, above, in Section 5.4.3, useful in the present invention may be used to quantitatively or qualitatively detect the presence of wild type or mutant fingerprint gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention may, additionally, be employed histologically, as in immunofluorescence or immunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled fingerprint gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant fingerprint gene peptide antibody may be determined according to well known methods. Those skilled in the art will be able to determine operative and optimal assay conditions for each determination by employing routine experimentation.

One of the ways in which the fingerprint gene peptide-specific antibody can be detectably labeled is by linking the same to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay,* CRC Press, Boca Raton, Fla., 1980; Ishikawa, et al., (eds.) *Enzyme Immunoassay,* Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

5.8.3. Imaging Cardiovascular Disease Cconditions

In some cases, differentially expressed gene products identified herein may be up-regulated under cardiovascular disease conditions and expressed on the surface of the affected tissue. Such target gene products allow for the non-invasive imaging of damaged or diseased cardiovascular tissue for the purposed of diagnosis and directing of treatment of the disease. For example, such differentially expressed gene products may include but are not limited to atherosclerosis specific adhesion molecules responsible for atherogenesis, or monocyte scavenger receptors that are up-regulated in response to oxidized LDL, which are discussed in Section 2, above. Alternatively, other such surface proteins may be specifically up-regulated in tissues suffering from ischemia/reperfusion or other tissues with atherosclerotic or restenotic lesions.

As described in the example in Section 9, below, the rchd523 gene is a gene that is up-regulated in endothelial cells under shear stress. Furthermore, the rchd523 gene encodes a novel G protein-coupled receptor, containing an extracellular amino terminal domain, in addition to seven transmembrane domains. The rchd523 gene product, therefore, provides an excellent tool for imaging cardiovascular disease conditions. This technique can be applied similarly to other transmembrane gene products, such as the rchd502 and rchd528 gene products. An example illustrating the use of this method in accordance with the invention is provided in Section 11, below.

Monoclonal antibodies, as described in Section 5.6.1.2, above, which specifically bind to such surface proteins, such as the rchd523 gene product, may be used for the diagnosis of cardiovascular disease by in vivo tissue imaging techniques. An antibody specific for a target gene product, or preferably an antigen binding fragment thereof, is conjugated to a label (e.g., a gamma emitting radioisotope) which generates a detectable signal and administered to a subject (human or animal) suspected of having cardiovascular disease. After sufficient time to allow the detectably-labeled antibody to localize at the diseased or damaged tissue site (or sites), the signal generated by the label is detected by a photoscanning device. The detected signal is then converted to an image of the tissue. This image makes it possible to localize the tissue in vivo. This data can then be used to develop an appropriate therapeutic strategy.

Antibody fragments, rather than whole antibody molecules, are generally preferred for use in tissue imaging. Antibody fragments accumulate at the tissue(s) more rapidly because they are distributed more readily than are entire antibody molecules. Thus an image can be obtained in less time than is possible using whole antibody. These fragments are also cleared more rapidly from tissues, resulting in a lower background signal. See, e.g., Haber et al., U.S. Pat. No. 4,036,945; Goldenberg et al., U.S. Pat. No. 4,331,647. The divalent antigen binding fragment $(Fab')_2$ and the monovalent Fab are especially preferred. Such fragments can be prepared by digestion of the whole immunoglobulin molecule with the enzymes pepsin or papain according to any of several well known protocols. The types of labels that are suitable for conjugation to a monoclonal antibody for diseased or damaged tissue localization include, but are not limited to radiolabels (i.e., radioisotopes), fluorescent labels and biotin labels.

Among the radioisotopes that can be used to label antibodies or antibody fragments, gamma-emitters, positron-emitters, X-ray-emitters and fluorescence-emitters are suitable for localization. Suitable radioisotopes for labeling antibodies include Iodine-131, Iodine-123, Iodine-125, Iodine-126, Iodine-133, Bromine-77, Indium-111, Indium-113m, Gallium-67, Gallium-68, Ruthenium-95, Ruthenium-97, Ruthenium-103, Ruthenium-105, Mercury-107, Mercury-203, Rhenium-99m, Rhenium-105, Rhenium-101, Tellurium-121m, Tellurium-122m, Tellurium-125m, Thulium-165, Thulium-167, Thulium-168, Technetium-99m and Fluorine-18. The halogens can be used more or less interchangeably as labels since halogen-labeled antibodies and/or normal immunoglobulins would have substantially the same kinetics and distribution and similar metabolism.

The gamma-emitters Indium-111 and Technetium-99m are preferred because these radiometals are detectable with a gamma camera and have favorable half lives for imaging in vivo. Antibody can be labelled with Indium-111 or Technetium-99m via a conjugated metal chelator, such as DTPA (diethlenetriaminepentaacetic acid). See Krejcarek et al., 1977, Biochem. Biophys. Res. Comm. 77:581; Khaw et al., 1980, Science 209:295; Gansow et al., U.S. Pat. No. 4,472,509; Hnatowich, U.S. Pat. No. 4,479,930, the teachings of which are incorporated herein by reference.

Fluorescent compounds that are suitable for conjugation to a monoclonal antibody include fluorescein sodium, fluorescein isothiocyanate, and Texas Red sulfonyl chloride. See, DeBelder & Wik, 1975, Carbohydrate Research 44:254–257. Those skilled in the art will know, or will be able to ascertain with no more than routine experimentation, other fluorescent compounds that are suitable for labeling monoclonal antibodies.

6. EXAMPLE: IDENTIFICATION OF GENES DIFFERENTIALLY EXPRESSED IN RESPONSE TO PARADIGM A: IN VITRO FOAM CELL PARADIGM

According to the invention, differential display may be used to detect genes that are differentially expressed in monocytes that were treated so as to simulate the conditions under which foam cells develop during atherogenesis.

6.1. MATERIALS AND METHODS 6.1.1. Cell Isolation and Culturing

Blood (~200 ml) was drawn into chilled 20 ml vacutainer tubes to which 3 ml of citrate phosphate dextrose (Sigma) was added. Blood was then pooled into 50 ml tubes and spun in the Beckman GS-6R at 1250 RPM for 15 minutes at 4° C. The upper clear layer (~25 ml) was then removed with a pipette and discarded and replaced with the same volume of 4° C. PBS. The blood was then mixed, and spun again at 2680 RPM for 15 minutes at 4° C. The upper layer was then removed and discarded, and the buffy coat at the interface was removed in ~5 ml and placed in a separate 50 ml tube, and the pipette was washed with 20 ml PBS. Cells were added to a T flask and stored at 4° C. for 16 hours. A small aliquot of the cells were then removed and counted using a hemacytometer. The final red blood cell concentration in the buffy coat population was then adjusted to $1.5\times10^9$/ml with PBS, the cells were added to Leucoprep tubes (Becton Dickinson) after being allowed to come to room temperature, and spun at 2300 RPM for 25 minutes at 25° C. The upper clear layer was removed and discarded and the turbid layer over the gel was removed and pooled in 50 ml tubes. Samples were then diluted to 50 ml with PBS (25° C.) and spun at 1000 RPM for 10 minutes. The supernatant was then removed, and the pellet was resuspended in 50 ml PBS. This procedure was repeated 3 more times. After the last spin, the cells were resuspended in a small volume of PBS and counted.

Tissue culture dishes were coated with bovine collagen before monocytes were plated out. ⅙ volume of 7× RPMI (JRH Biosciences) was added to Vitrogen 100 collagen (Celtrix) which was then diluted 1:10 with RPMI to a final concentration of 0.35 mg/ml. Collagen mixture was then added to plates (2.5 ml/100 mm dish) and placed at 37° C. for at least one hour to allow for gel formation. After gel formation has taken place, the RPMI was removed and cells were added in RPMI/10% plasma derived serum (PDS). PDS was prepared by drawing blood into chilled evacuated tubes containing 1/10th volume 3.8% sodium citrate. Blood was then transferred into new Sorvall tubes and spun at 14,000–16,000 RPM for 20 minutes at 4° C. Plasma layer was removed and pooled in new tubes to which 1/50th volume 1M $CaCl_2$ was added. Plasma was mixed and aliquoted into new Sorvall tubes and incubated at 37° for 2 hours to allow for fibrin clot formation. The clot was then disturbed with a pipette to allow it to contract and tubes were spun at 14,500 RPM for 20 minutes at 25° C. Supernatant was collected, pooled, and heat inactivated at 56° C. prior to sterile filtration and freezing.

Purified human monocytes were cultured in 10% PDS/RPMI containing 5 units/ml of Genzyme recombinant human MCSF for 5 days before being treated with LDL, oxidized LDL, acetylated LDL (all LDL at 50 μg/ml), lysophosphatidylcholine (Sigma, 37.5 μM), or homocysteine (Sigma, 1 mM). After 30 incubation with these reagents for periods ranging from 2 hours up to 3 days, the media was withdrawn and the cells were dissolved in RNA lysis buffer and RNA was prepared as described, above, in Section 6.1.

Lipoproteins For oxidation, human LDL (Sigma) was first diluted to 1 mg/ml with PBS and then dialyzed against PBS at 4° C. overnight. LDL was then diluted to 0.3 mg/ml with PBS. $CuSO_4.5H_2O$ was then added to 5 uM final concentration, and the solution was incubated in a T flask in a 37° C. incubator for 24 hr. LDL solution was then dialyzed at 4° C. against 0.15M NaCl/0.3 mM EDTA for 2 days with several changes, before being removed and concentrated using an Amicon spin column by spinning for 1 hr. 4000 RPM at 4° C.

For acetylation, 1 ml of 5 mg/ml LDL was added to 1 ml of a saturated solution of NaOAc in a 15 ml tube on ice on a shaker at 4° C. 8 μl of acetic anhydride was added 2 μl at a time over 1 hr. LDL was then dialyzed for 48 hr. against 0.15M NaCl/0.3 mM EDTA at 4° C. for 48 hr. with several changes. Final concentrations of derivatized LDL's were determined by comparing to a dilution curve of native LDL analyzed at $OD_{280}$, with 0.15M NaCl/0.3 mM EDTA used as diluent in all cases.

6.1.2. Analysis of Paradigm Material

Differential Display:

Removal of DNA: The RNA pellet was resuspended in $H_2O$ and quantified by spectrophotometry at $OD_{260}$. Approximately half of the sample was then treated with DNAse I to remove contaminating chromosomal DNA. RNA was amplified by PCR using the following procedure. 50 ul RNA sample (10∝20 μg), 5.7 μl 10× PCR buffer (Perkin-Elmer/Cetus), 1 μl RNAse inhibitor (40 units/μl) (Boehringer Mannheim, Germany) were mixed together, vortexed, and briefly spun. 2 μl DNAse I (10 units/μl) (Boehringer Mannheim) was added to the reaction which was incubated for 30 min. at 37° C. The total volume was brought to 200 μl with DEPC $H_2O$, extracted once with phenol/chloroform, once with chloroform, and precipitated by adding 20 μl 3M NaOAc, pH 4.8, (DEPC-treated), 500 μl absolute ETOH and incubating for 1 hour on dry ice or −20° C. overnight. The precipitated sample was centrifuged for 15 min., and the pellet was washed with 70% ETOH. The sample was re-centrifuged, the remaining liquid was aspirated, and the pellet was resuspended in 100 μl $H_2O$. The concentration of RNA was measured by reading the $OD_{260}$.

First strand cDNA synthesis: For each RNA sample duplicate reactions were carried out in parallel. 400 ng RNA plus DEPC $H_2O$ in a total volume of 10 μl were added to 4 μl $T_{11}XX$ (SEQ ID NO:31) reverse primer (10 μM) (Operon). The specific primers used in each experiment are provided in the Description of the Figures in Section 4, above. The mixture was incubated at 70° C. for 5 min. to denature the RNA and then placed at r.t. 26 μl of reaction mix containing the following components was added to each denatured RNA/primer sample: 8 μl 5× First Strand Buffer (Gibco/BRL, Gaithersburg, Md.), 4 μl 0.1M DTT (Gibco/BRL), 2 μl RNAse inhibitor (40 units/μl) (Boehringer Mannheim), 4 μl 200 μM dNTP mix, 6 μl $H_2O$, 2 μl Superscript reverse transcriptase (200 units/μl) (Gibco/BRL). The reactions were mixed gently and incubated for 30 min. at 42° C. 60 μl of $H_2O$ (final volume=100 μl) were then added and the samples were denatured for 5 min. at 85° C. and stored at −20° C.

PCR reactions: 13 μl of reaction mix was added to each tube of a 96 well plate on ice. The reaction mix contained 6.4 μl $H_2O$, 2 μl 10× PCR Buffer (Perkin-Elmer), 2 μl 20 μM dNTP's, 0.4 μl $^{35}S$ dATP (12.5 μCi/μl; 50 μCi total) (Dupont/NEN), 2 μl forward primer (10 μM) (Operon), and 0.2 μl AmpliTaq Polymerase (5 units/μl) (Perkin-Elmer). Next, 2 μl of reverse primer ($T_{11}XX$, 10 μM) were added to the side of each tube followed by 5 μl of cDNA also to the sides of the tubes, which were still on ice. The specific primers used in each experiment are provided in the Description of the Figures in Section 4, above. Tubes were capped and mixed, and brought up to 1000 RPM in a centrifuge then returned immediately to ice. The PCR machine (Perkin-Elmer 9600) was programmed for differential display as follows:

| | |
|---|---|
| 94° C. | 2 min. |
| *94° C. | 15 sec. |
| *40° C. | 2 min. |
| *ramp 72° C. | 1 min. |
| *72° C. | 30 sec. |
| 72° C. | 5 min. |
| 4° C. | hold |

* = ×40

When the PCR machine reached 94° C., the plate was removed from ice and placed directly into the Perkin-Elmer 9600 PCR machine . Following PCR, 15 μl of loading dye, containing 80% formamide, 10 mM EDTA, 1 mg/ml xylene cyanol, 1 mg/ml bromphenol blue were added. The loading dye and reaction were mixed, incubated at 85° C. for 5 min., cooled on ice, centrifuged, and placed on ice. Approximately 4 μl from each tube were loaded onto a prerun (60V) 6% acrylamide gel. The gel was run at approximately 80V until top dye front was about 1 inch from bottom. The gel was transferred to 3MM paper (Whatman Paper, England) and dried under vacuum. Bands were visualized by autoradiography.

Band isolation and amplification: Differentially expressed bands were excised from the dried gel with a razor blade and placed into a microfuge tube with 100 µl H$_2$O and heated at 100° C. for 5 min., vortexed, heated again to 100° C. for 5 min., and vortex again. After cooling, 100 µl H$_2$O, 20 µl 3M NaOAc, 1 µl glycogen (20 mg/ml), and 500 µl ethanol were added and chilled. After centrifugation, the pellet was washed and resuspended in 10 µl H$_2$O.

The isolated differentially expressed bands were then amplified by PCR using the following reaction conditions:

| | |
|---|---|
| 58 µl | H$_2$O |
| 10 µl | 10× PCR Buffer |
| 10 µl | 200 µm dNTP's |
| 10 µl | 10 µM reverse primer |
| 10 µl | 10 µM forward primer |
| 1.5 µl | amplified band |
| 0.5 µl | AmpliTaq polymerase (5 units/µl) (Perkin Elmer) |

PCR was performed using the program described in this Section, above, for differential display. After PCR, glycerol loading dyes were added and samples were loaded onto a 2% preparative TAE/Biogel (Bio101La Jolla, Calif.) agarose gel and eluted. Bands were then excised from the gel with a razor blade and vortexed for 15 min. at r.t., and purified using the Mermaid kit from Bio101 by adding 3 volumes of Mermaid high salt binding solution and 8 µl of resuspended glassfog in a microfuge tube. Glassfog was then pelleted, washed 3 times with ethanol wash solution, and then DNA was eluted twice in 10 µl at 50° C.

Subcloning: The TA cloning kit (Invitrogen, San Diego, Calif.) was used to subclone the amplified bands. The ligation reaction typically consisted of 4 µl sterile H$_2$O, 1 µl ligation buffer, 2 µl TA cloning vector, 2 µl PCR product, and 1 µl T4 DNA ligase. The volume of PCR product can vary, but the total volume of PCR product plus H$_2$O was always 6 µl. Ligations (including vector alone) were incubated overnight at 12° C. before bacterial transformation. TA cloning kit competent bacteria (INVαF': enda1, recAl, hsdR17 (r-k, m+k), supE44, λ-, thi-1, gyrA, relA1, φ80lacZαΔM15Δ (lacZYA-argF), deoR+, F') were thawed on ice and 2 µl of 0.5M β-mercaptoethanol were added to each tube. 2 µl from each ligation were added to each tube of competent cells (50 µl), mixed without vortexing, and incubated on ice for 30 min. Tubes were then placed in 42° C. bath for exactly 30 sec., before being returned to ice for 2 min. 450 µl of SOC media (Sambrook et al., 1989, supra) were then added to each tube which were then shaken at 37° C. for 1 hr. Bacteria were then pelleted, resuspended in ~200 µl SOC and plated on Luria broth agar plates containing X-gal and 60 µg/ml ampicillin and incubated overnight at 37° C. White colonies were then picked and screened for inserts using PCR.

A master mix containing 2 µl 10× PCR buffer, 1.6 µl 2.5 mM dNTP's, 0.1 µl 25 mM MgCl$_2$, 0.2 µl M13 reverse primer (100 ng/µl), 0.2 µl M13 forward primer (100 ng/µl), 0.1 µl AmpliTaq (Perkin-Elmer), and 15.8 µl H$_2$O was made. 40 µl of the master mix were aliquoted into tubes of a 96 well plate, and whole bacteria were added with a pipette tip prior to PCR. The PCR machine (Perkin-Elmer 9600) was programmed for insert screening as follows:

| | |
|---|---|
| 94° C. | 2 min. |
| *94° C. | 15 sec. |
| *47° C. | 2 min. |
| *ramp 72° C. | 30 sec. |
| *72° C. | 30 sec. |
| 72° C. | 10 min. |
| 4° C. | hold |

* = ×35

Reaction products were eluted on a 2% agarose gel and compared to vector control. Colonies with vectors containing inserts were purified by streaking onto LB/Amp plates. Vectors were isolated from such strains and subjected to sequence analysis, using an Applied Biosystems Automated Sequencer (Applied Biosystems, Inc. Seattle, Wash.).

Northern analysis: Northern analysis was performed to confirm the differential expression of the genes corresponding to the amplified bands. The probes used to detect mRNA were synthesized as follows: typically 2 µl amplified band (~30 ng), 7 µl H$_2$O, and 2 µl 10× Hexanucleotide mix (Boehringer-Mannheim) were mixed and heated to 95° C. for 5 min., and then allowed to cool on ice. The volume of the amplified band can vary, but the total volume of the band plus H$_2$O was always 9 µl. 3 µl dATP/dGTP/dTTP mix (1:1:1 of 0.5 mM each), 5 µl α$^{32}$P dCTP 3000 Ci/mM (50 µCi total) (Amersham, Arlington Heights, Ill.), and 1 µl Klenow (2 units) (Boehringer-Mannheim) were mixed and incubated at 37° C. After 1 hr., 30 µl TE were added and the reaction was loaded onto a Biospin-6™ column (Biorad, Hercules, Calif.), and centrifuged. A 1 µl aliquot of eluate was used to measure incorporation in a scintillation counter with scintillant to ensure that 10$^6$cpm/µl of incorporation was achieved.

The samples were loaded onto a denaturing agarose gel. A 300 ml 1% gel was made by adding 3 g of agarose (SeaKem™ LE, FMC BioProducts, Rockland, Me.) and 60 ml of 5× MOPS buffer to 210 ml sterile H2O. 5× MOPS buffer (0.1M MOPS (pH 7.0), 40 mM NaOAc, 5 mM EDTA (pH 8.0)) was made by adding 20.6 g of MOPS to 800 ml of 50 mM NaOAc (13.3 ml of 3M NaOAc pH 4.8 in 800 ml sterile H$_2$O); then adjusting the pH to 7.0 with 10M NaOH; adding 10 ml of 0.5M EDTA (pH8.0); and adding H$_2$O to a final volume of 1 L. The mixture was heated until melted, then cooled to 50° C., at which time 5 µl ethidium bromide (5 mg/ml) and 30 ml of 37% formaldehyde of gel were added. The gel was swirled quickly to mix, and then poured immediately. 2 µg RNA sample, 1× final 1.5× RNA loading dyes (60% formamide, 9% formaldehyde, 1.5× MOPS, 0.075% XC/BPB dyes) and H$_2$O were mixed to a final volume of 40 µl. The tubes were heated at 65° C. for 5 min. and then cooled on ice. 10 µg of RNA MW standards (New England Biolabs, Beverly, Mass.) were also denatured with dye and loaded onto the gel. The gel was run overnight at 32V in MOPS running buffer.

The gel was then soaked in 0.5 µg/ml Ethidium Bromide for 45 min., 50 mM NaOH/0.1M NaCl for 30 min., 0.1M Tris pH 8.0 for 30 min., and 20× SSC for 20 min. Each soaking step was done at r.t. with shaking. The gel was then photographed along with a fluorescent ruler before blotting with Hybond-N membrane (Amersham), according to the methods of Sambrook et al., 1989, supra, in 20× SSC overnight.

For hybridization, the blot was placed into a roller bottle containing 10 ml of prehybridization solution consisting of 50% formamide and 1× Denhardt's solution, and placed into 65° C. incubator for 30 min. The probe was then heated to 95° C., chilled on ice, and added to 10 ml of hybridization solution, consisting of 50% formamide, 1× Denhardt's solution, 10% dextransulfate, to a final concentration of 10$^6$ cpm/ml. The prehybridization solution was then replaced with the probe solution and incubated overnight at 42° C. The following day, the blot was washed three times for 30 min. in 2× SSC/0.1% SDS at room temperature before being covered in plastic wrap and put down for exposure.

RT-PCR Analysis: RT-PCR was performed to detect differentially expressed levels of mRNA from the genes corresponding to amplified bands. First strand synthesis was conducted by mixing 20 μl DNased RNA (~2 μg), 1 μl oligo dT (Operon) (1 μg), and 9.75 μl $H_2O$. The samples were heated at 70° C. for 10 min., and then allowed to cool on ice. 10 μl first strand buffer (Gibco/BRL), 5 μl 0.1M DTT, 1.25 μl 20 mM dNTP's (500 μM final), 1 μl RNAsin (40 units/μl) (Boehringer Mannheim), and 2 μl Superscript Reverse Transcriptase (200 units/μl) (Gibco/BRL) were added to the reaction, incubated at 42° C. for 1 hr., and then placed at 85° C. for 5 min., and stored at −20° C.

PCR was performed on the reverse transcribed samples. Each reaction contained 2 μl 10× PCR buffer, 14.5 μl $H_2O$, 0.2 μl 20 mM dNTP's (200 μM final), 0.5 μl 20 μM forward primer (0.4 μM final), 0.5 μl 20 μM reverse primer (0.4 μM final), 0.3 μl AmpliTaq polymerase (Perkin-Elmer/Cetus), 2 μl cDNA dilution or positive control (~40 pg). The specific primers used in each experiment are provided in the Description of the Figures in Section 4, above. Samples were placed in the PCR 9600 machine at 94° C. (hot start), which was programmed as follows:

| | |
|---|---|
| 94° C. | 2 min. (samples loaded) |
| *94° C. | 45 sec. |
| *55° C. | 45 sec. |
| *72° C. | 2 min. |
| 72° C. | 5 min. |
| 4° C. | hold |

* = 35×

Reactions were carried out on cDNA dilution series and tubes were removed at various cycles from the machine during 72° C. step. Reaction products were eluted on a 1.8% agarose gel and visualized with ethidium bromide.

6.1.3. Chromosomal Localization of Target Genes

Once the nucleotide sequence has been determined, the presence of the gene on a particular chromosome is detected. Oligonucleotide primers based on the nucleotide sequence of the target gene are used in PCR reactions using individual human chromosomes as templates. Individual samples of each the twenty-three human chromosomes are commercially available (Coriel Institute for Medical Research, Camden, N.J.). The chromosomal DNA is amplified according to the following conditions: 10 ng chromosomal DNA, 2 μl 10× PCR buffer, 1.6 μl 2.5 mM dNTP's, 0.1 μl 25 mM $MgCl_2$, 0.2 μl reverse primer (100 ng/μl), 0.2 μl forward primer (100 ng/μl), 0.1 μl Taq polymerase, and 15.8 μl $H_2O$. Samples are placed in the PCR 9600 machine at 94° C. (hot start), which is programmed as follows:

| | |
|---|---|
| 94° C. | 2 min. (samples loaded) |
| *94° C. | 20 sec. |
| *55° C. | 30 sec. |
| *72° C. | 30 sec. |
| 72° C. | 5 min. |
| 4° C. | hold |

* = 35×

7. EXAMPLE: IDENTIFICATION OF GENES DIFFERENTIALLY EXPRESSED IN RESPONSE TO PARADIGM B: IN VIVO MONOCYTES

In an alternative embodiment of the invention, genes differentially expressed in monocytes were detected under highly physiologically relevant, in vivo conditions. According to Paradigm B, human subjects were held in a clinical setting and the fat/cholesterol content of their diets was controlled. Monocytes were isolated at different stages of treatment, and their gene expression pattern was compared to that of control groups.

By use of Paradigm B, the human bcl-2 gene was identified. Its expression decreases in response to the atherogenic conditions of high fat/high cholesterol (FIG. 1). The Apo E-/- mouse is the first mouse model of atherosclerosis with pathology similar to that of human plaque development (Plump et al., 1992, Cell 71: 343–353). Serum cholesterol levels in these mice on a chow diet is five times higher than those of control littermates. To address whether the regulation of the mouse bcl-2 gene is also affected by serum cholesterol levels, monocytes from apoE-deficient mice and littermate wild-type controls were purified and mouse bcl-2 mRNA levels were compared using quantitative RT-PCR. By this method, mouse bcl-2 mRNA levels were significantly lower in the apoE-deficient mice relative to the wild-type controls (FIG. 3).

The differential expression pattern of the human glutathione peroxidase gene (HUMGPXP1) was also discovered. The differential expression of HUMGPXP1 was initially detected in a preliminary detection system, described, below, in Section 7.1.2. Once HUMGPXP1 sequences were obtained, the gene's differential expression pattern was verified and characterized under the physiologically relevant conditions of Paradigm B. Glutathione peroxidase is known to be involved in the removal of toxic peroxides that form in the course of growth and metabolism under normal aerobic conditions and under oxidative stress. Human plasma glutathione peroxidase gene was originally isolated from a human placenta cDNA library (Takahashi et al., 1990, J. Biochem. 108: 145–148). It has been shown to be expressed in two human cell lines of the myeloid lineage (Porter et al., 1992, Clinical Science 83: 343–345). Other studies have also linked reduced levels of this enzyme with heart attack risk (Guidi, et al., 1986, J. Clin. Lab Invest. 46: 549–551; Wang et al., 1981, Klin. Wochenschr. 59: 817–818; Kok et al., 1989, J. Am. Med. Assoc. 261: 1161–1164; and Gromadzinska & Sklodowska, 1990, J. Am. Med. Assoc. 263: 949–950). Glutathione peroxidase has not been previously known to be down-regulated in human monocytes under cardiovascular disease conditions, as described herein.

Interestingly, bcl-2 has been recognized as playing a key role in preventing apoptosis, and expression of glutathione peroxidase in the absence of bcl-2 is able to compensate for this loss by preventing apoptosis (Hockenbery et al., 1993, Cell 75: 241–251). These findings regarding bcl-2 and HUMGPXP1, described herein in this section, suggested a novel role for the monocyte in plaque formation which involves apoptosis induction caused by high LDL concentrations inside the cell, or perhaps by oxidative stress in the cell mediated by oxidized LDL.

To confirm this relationship between apoptosis and atherosclerosis, the ability of bcl-2 expression to ameliorate atherosclerosis is tested. Because bcl-2 is normally down-regulated under atherogenic conditions, a transgenic mouse strain is engineered in which the human bcl-2 gene is expressed under the control of the scavenger receptor promoter, which is induced in monocyte foam cells under atherogenic conditions. This transgenic mouse is then crossed with an apoE-deficient atherosclerotic mouse model. The ability of the increased expression of the bcl-2 target gene to ameliorate atherosclerosis is demonstrated by a decrease in initiation and progression of plaque formation observed in the transgenic apoE-deficient mouse.

The identification of the differential expression of these genes, therefore, provides targets for the treatment and diagnosis of cardiovascular disease. Intervening in the apoptotic pathway through Bcl-2 and glutathione peroxidase, may lead to lesion regression or prevention of plaque formation, or both. Furthermore, the discovery of a connection between the apoptotic pathway and atherosclerosis demonstrates the effectiveness of the methods described herein in identifying the full panoply of gene products that are involved in the atherosclerotic disease process. Furthermore, the down-regulation of bcl-2 and HUMGPXP1 under Paradigm B provides a fingerprint for the study of the effect of excess LDL on monocytes.

7.1. MATERIALS AND METHODS

7.1.1. In Vivo Cholesterol Studies

Patients were held in a clinical setting for a total of 9 weeks during which time their lipid intake was very tightly controlled. There were a total of 3 diets, and each patient was held on each diet for 3 weeks. Patients were healthy young (third decade of life) individuals with no history or symptoms of heart disease or dislipidemias. The 3 diets are described below:

| | |
|---|---|
| American Heart Association Diet II | |
| fat | 25% |
| cholesterol | 80 mg/1000 kCal |
| polyunsaturated/saturated fat | 1.5 |
| Average American Diet | |
| fat | 43% |
| cholesterol | 200 mg/1000 kCal |
| polyunsaturated/saturated fat | 0.34 |
| Combination Diet | |
| fat | 43% |
| cholesterol | 80 mg/1000 kCal |
| polyunsaturated/saturated fat | 0.34 |

The 3 diets were isocaloric, and the individual components of each diet may vary with the participant's preference as long as the lipid levels in the diet were maintained.

Cell Isolation

At the end of each 3 week diet period, blood was drawn from each patient after a 12 hour period of fasting and monocytes were purified. 50 ml of blood was drawn into 5 evacuated tubes containing 1.4 ml each of citrate phosphate dextrose to prevent coagulation. Blood was pooled into 50 ml tubes and spun at 400 g (1250 RPM/Sorvall RC3B) for 15 minutes at 4° C. The upper serum layer (~25 ml) was then removed with a pipette and replaced with phosphate buffered saline (PBS) at 4° C. The blood was mixed and then spun at 1850×g (2680 RPM) for 15 minutes at 4° C. Most of the clear upper layer was removed with a pipette, before the buffy coat at the interface was taken in ~5 ml. The buffy coat was placed into a separate 50 ml tube, and the pipette used to remove it was washed with 20 ml PBS. A small aliquot of these cells was then diluted 1:1000 in PBS and counted under a microscope using a hemacytometer. Red blood cell concentration was then adjusted with PBS to a final concentration of $1.5\times10^9$/ml, and 10 ml aliquots were added to Leucoprep Becton Dickinson) tubes for monocyte isolation. Tubes were spun for 25 minutes at 25° C. in a Sorvall RT6000 with the brake off. Most of the clear upper layer was discarded, and the turbid layer above the gel was saved and pooled in 50 ml tubes. The volume of each tube was then increased to 50 ml with 25° C. PBS, and spun at 1000 RPM (Sorvall RC3B) for 10 minutes at 4° C. The liquid was then discarded, the pellet was resuspended in 50 ml PBS, and spun again. This process was repeated 3 more times. The final cell pellet was then resuspended in 2 ml RNA lysis buffer (Sambrook et al., 1989, supra) and frozen for subsequent RNA isolation as described above in Section 6.1.1.

Differential display, Northern analysis, RT-PCR, subcloning, and DNA sequencing were carried out as described, above, in Section 6.1.2.

7.1.2.Preliminary Detection System

The preliminary detection system described in this section was used to identify sequences that are differentially expressed in a readily assayed, in vitro system. Sequences that showed some homology to those thought to be involved in cardiovascular disease were then used as specific primers or probes, or both, in Paradigm B, wherein the differential expression was ascertained under physiologically relevant conditions, as described in section 7.1.1, above.

Cell culture Blood (~100 ml) was drawn from healthy human donors into vacutainer tubes containing heparin (Becton Dickinson). Blood was diluted 1:1 with PD (Phosphate buffered saline (PBS) without Ca or Mg, plus 0.3 mM EDTA), and layered onto Ficoll (Lymphocyte Separation Media-Organon Teknikon) as 30 ml of blood/7 ml ficoll in a 50 ml blue-capped Falcon tube, and centrifuged at 2000 RPM for 25 min. at room temperature (r.t.). The buffy coat was removed with a pipette, transferred to another 50 ml tube, diluted to 30 ml with PD, and centrifuged at 1200 RPM for 10 min. at r.t. The pellet was resuspended in 30 ml PD and the previous centrifugation step was repeated. The pellet was resuspended in 40 ml RPMI (2 mM 1-Glutamine+ penicillin/streptomycin), plated onto 4 plates, and incubated at 37° C. for 2 hours. Supernatant was removed, and the plates were washed 3× with PBS at 37° C. Plates were finally resuspended in 10 ml each with RPMI/20% human AB serum (Sigma, St. Louis, Mo.). On day 5, the media was changed and 100 units/ml of human γ-IFN (Genzyme) were added. On day 7, the media was removed and replaced with RPMI/20% human LDL-deficient serum+100 units/ml of human γ-IFN. Native, oxidized, and acetylated LDL were each added to one plate with the fourth plate serving as control. After the specified incubation time (5 hr. or 24 hr.) the media was removed and the cells were resuspended in 2 ml guanidine isothiocyanate RNA lysis buffer (Sambrook et al., 1989, supra). Lysed cells were then syringed with 23 G. needle, layered over 5.7M CsCl, and centrifuged for 20 hr. at 35K RPM. RNA was isolated according to the method of Sambrook et al., 1989, supra.

Lipoproteins were prepared as described, above, in section 6.1.1. Differential display, Northern analysis, RT-PCR, subcloning, and DNA sequencing were carried out as described, above, in Section 6.1.2. For differential display, the primers used were $T_{11}$CC (SEQ ID NO:32) (reverse) and OPE4 (forward), consisting of 5'GTGACATGCC3'(SEQ ID NO:33). For RT-PCR, the first strand cDNA was primed with $T_{11}$CC (SEQ ID NO:32), and PCR reactions were carried out with rfhma15 primers (for-catgcctgtagaaaaaggtt; SEQ ID NO:34/rev-cttcatagaatctaagccta; SEQ ID NO:35), and mouse γactin primers (for-cctgatagatgggcactgtgt (SEQ ID NO:12)/rev-gaacacggcattgtcactaact; SEQ ID NO:13).

7.1.3. Transgenic ApoE-Deficient Mouse Expressing Human bcl-2

Transgenic mice bearing a construct (FIG. 31) with the mouse scavenger receptor regulatory element (5 kb) (M. Freeman, et al., 1995, unpublished results) driving expression of the human bcl-2 gene (hbcl-2) were produced. The scavenger receptor regulatory element (ScR) is known to activate reporter gene expression in peritoneal macrophages in transgenic mice (M. Freeman, 1995, unpublished results). This 5 kb fragment is linked to the human bcl-2 cDNA (Cleary, et al., 1986, supra) via a NotI restriction site. Human growth hormone (hGH) sequences (Mayo, et al., 1983, Nature 306: 86–88) are then ligated onto the 3' end of this construct through filled-in BamHI and EcoRV sites to provide message stability. This construct is then digested with XhoI and the 9 kb ScR-hbcl2-hGH sequences are purified away from vector sequences. Another plasmid sample is digested with KpnI to yield a fragment with only 1.5 kb of scavenger receptor regulatory sequences which provide a lower level of expression. These fragments are then injected independently into mouse embryos derived from the FVB and C57BL/6 mouse strains according to standard protocols (Hogan, et al., Manipulating the Mouse Embryo, 1994, Cold Spring Harbor Laboratory Press). Following birth, tail sections are cut from mice derived from injected embryos and analyzed for the presence of transgene sequences using hbcl-2 sequences as probes on Southern blots.

Transgenic mice bearing the ScR-hbcl2-hGH construct are then bred to wild-type mice of the same respective strain, and then the offspring are backcrossed to produce homozygous lines of mice. These mice are then bred to apoE-deficient mice. Offspring are analyzed for presence of the ScR-hbcl2-hGH by preparing tail sections and probing with hbcl-2 sequences on Southern blots. Offspring are then analyzed for lesion formation and progression according to the methods of Plump, et al., 1992, supra.

7.2. RESULTS

Differential display analysis was carried out on monocyte RNA derived from the blood of patients whose serum cholesterol levels were manipulated through fat/cholesterol intake in their diets. FIG. 1 shows band #14 which was present in the low dietary fat/low serum cholesterol conditions and goes away in the high dietary fat/high serum cholesterol conditions. When a radioactively labeled probe was prepared from band #14 and hybridized with a Northern blot prepared from RNA from the same patient (FIG. 2), an 8 kb band was seen which was present in low serum cholesterol and disappeared in high serum cholesterol conditions. When band #14 sequences were subcloned, sequenced, and compared with the sequence database a 98% (203/207 bp) sequence similarity with the human bcl-2 gene (Cleary et al., 1986, Cell 47, 19–28) was obtained, indicating that band #14 is bcl-2.

Glutathione peroxidase (HUMGPXP1) in expression in monocytes was examined to determine its physiological relationship to bcl-2. Differential expression of HUMGPXP1 was first detected in a preliminary detection system using monocytes cultured in vitro. Human monocytes were prepared as described above in subsection 7.1.2. Cells were lysed after 5 hours and RNA was prepared. Differential display analysis was carried out, and regulated bands were isolated and characterized. The DNA sequence was determined from a number of independent subclones of amplified sequences of one such regulated band designated band 15. Using the BLAST program (Altschul, et al., 1990, J. Mol. Biol. 215: 403–410), a 176/177 (99%) sequence similarity was found between band 15 a sequence for human plasma glutathione peroxidase exon 1 (HUMGPXP1). This sequence occurs upstream of the reported transcription start site. Nonetheless, RT-PCR analysis confirmed that the band 15 sequences are in fact within the same transcription unit as sequences downstream of the reported transcription start site.

Based on this preliminary result, the gene expression pattern of glutathione peroxidase (HUMGPXP1) was further analyzed for verification and characterization in physiologically relevant samples according to Paradigm B. Monocytes derived from human blood under atherogenic conditions (high serum cholesterol) and healthy conditions (low serum cholesterol) were examined with RT-PCR. As shown in FIG. 4, there appears to be 2–3 fold less cDNA amplified by the HUMGPXP1 primers from the high fat/cholesterol monocytes than in the low fat/cholesterol monocytes, while the actin control bands are the same.

Monocytes from apoE-deficient mice and littermate wild-type controls were purified and mouse bcl-2 mRNA levels were compared using quantitative RT-PCR. By this method, mouse bcl-2 mRNA levels were significantly lower in the apoE-deficient mice relative to the wild-type controls (FIG. 3).

These results demonstrate that bcl-2 is an excellent target gene for intervening in lesion formation and development. It was previously known that, under normal conditions, bcl-2 expression prevents apoptosis. The observed down-regulation of bcl-2 caused by atherogenic conditions, therefore, provides an explanation of how such atherogenic conditions may lead to plaque formation. By down-regulating the normally protective bcl-2 gene, high serum cholesterol triggers a series of events, entailing the induction of the apoptotic pathway, which results in programmed cell death, which in turn causes an inflammatory response and subsequent plaque formation.

This model may be tested by counteracting the observed down-regulation of bcl-2. The human bcl-2 gene is placed in the ScR-hbcl2-hGH construct in which it is transcribed by a promoter that is activated in monocyte foam cells under atherogenic conditions. This construct is then introduced into an apoE-deficient mouse that otherwise serves as a model for atherosclerosis. The effect of bcl-2 expression on atherosclerosis is evidenced by the reduction in plaque initiation and development in the apoE-deficient mice bearing the construct. Amelioration of atherosclerosis may, therefore, be accomplished by such intervention in the down-regulation of the bcl-2 target gene.

8. EXAMPLE: IDENTIFICATION OF GENES DIFFERENTIALLY EXPRESSED IN RESPONSE TO PARADIGM C: IL-1 INDUCTION OF ENDOTHELIAL CELLS

According to the invention, differential display was used to detect four novel genes that are differentially expressed in endothelial cells that were treated in vitro with IL-1. Three of these genes, rchd024, rchd032, and rchd036, are not homologous to any known gene. The fourth gene, rchd005, is 70% homologous to a cloned shark gene called bumetanide-sensitive Na-K-Cl cotransport protein. A human homolog of this gene has been reported, but the sequence has not yet been published (Xu et al., 1994, Proc. Natl. Acad. Sci. USA 91: 2201–2205).

The discovery of the up-regulation of these four genes provides a fingerprint profile of IL-1 induced endothelial cells. This fingerprint profile can be used in the treatment and diagnosis of cardiovascular diseases, including but not limited to atherosclerosis, ischemia/reperfusion, hypertension, restenosis, and arterial inflammation.

8.1. MATERIALS AND METHODS

Primary cultures of HUVEC's were established from normal term umbilical cords as described (In Progress in Hemostasis and Thrombosis, Vol. 3, P. Spaet, editor, Grune & Stratton Inc., New York, 1–28). Cells were grown in 20% fetal calf serum complete media (Luscinstas et al., 1989, J. Immunol. 142: 2257–2263) and passaged 1–3 times before activation.

For activation, cells were cultured with 10 units/ml of human IL-1β for 1 or 6 hr. before lysis in guanidinium isothiocyanate RNA lysis buffer (Sambrook et al., 1989, supra). Lysed cells were then syringed with a 23 G. needle, layered over 5.7M CsCl, and centrifuged for 20 hr. at 35K.

Alternatively, cells were induced in the presence of 100 μM lysophosphatidylcholine, or 50 μg/ml oxidized human LDL (Sigma) for periods of 1 or 6 hr. RNA was isolated as described, above, in Section 6.1. Differential display, Northern analysis, RT-PCR, subcloning, and DNA sequencing were carried out as described, above, in Section 6.1.2, except that Northern blot hybridizations were carried out as follows: for pre-hybridization, the blot was placed into roller bottle containing 10 ml of rapid-hyb solution (Amersham), and placed into 65° C. incubator for at least 1 hr. For hybridization, $1\times10^7$ cpm of the probe was then heated to 95° C., chilled on ice, and added to 10 ml of rapid-hyb solution. The prehybridization solution was then replaced with probe solution and incubated for 3 hr at 65° C. The following day, the blot was washed once for 20 min. at r.t. in 2× SSC/0.1% SDS and twice for 15 min. at 65° C. in 0.1× SSC/0.1% SDS before being covered in plastic wrap and put down for exposure.

Chromosomal locations were determined according to the method described in Section 6.1.3, above. For rchd024, the primers used were for-cccatagactaggctcatag (SEQ ID NO:41), and rev-tttaaagagaaattcaaatc (SEQ ID NO:42).

8.2. RESULTS

HUVEC's were activated with 10 units/ml IL-1β for 1 or 6 hours and compared to resting HUVEC's using differential display. As shown in FIG. 5, a band marked rchd005 is present in lanes 11 and 12 (IL-1, 6 hr.) but not in lanes 9 and 10 (control), or lanes 7 and 8 (IL-1, 1 hr.). This band, rchd005, was isolated and subcloned and sequenced. When a probe prepared form this band was used to screen a Northern blot, expression was seen at 6 hr., but not at 1 hr. or in the control (FIG. 6). However, when this same probe was hybridized to a Northern blot prepared from shear stressed RNA, according to Paradigm D described in Section 9, below, a different pattern of up-regulation was also seen (FIG. 7). Expression was up at 1 hr. and then nearly disappeared by 6 hr. Amplified rchd005 DNA was subcloned and sequenced. Sequence analysis revealed an approximately 360 bp insert (FIG. 8) with 70% sequence similarity to a cloned shark gene called bumetanide-sensitive Na-K-Cl cotransport protein. Another IL-1 inducible band, rchd024, is shown in FIG. 9. Northern analysis on IL-1 up-regulated RNA reveals a 10 kb message present at 6 hr. (FIG. 10) that also shows a low level of up-regulation under shear stress at 6 hr. (FIG. 11). The DNA sequence was obtained from subclones of amplified DNA (FIG. 12). Database searching revealed no significant sequence similarities. A PCR amplification experiment determined that the rchd024 gene is located on human chromosome 4.

Band rchd032 was isolated on the basis of its differentially increased expression after 6 hr. treatment with IL-1 (FIG. 13), which was confirmed by RT-PCR analysis (FIG. 14). Amplified rchd032 sequences were subcloned and sequenced (FIG. 15). No significant homology to any known gene was found.

Band rchd036 was also isolated on the basis of its differential expression 6 hr. after IL-1 treatment (FIG. 16). Northern analysis (FIG. 17) revealed an 8 kb band which was up-regulated 6 hr. after IL-1 treatment. Another Northern analysis was performed testing rchd036 under the shear stress condition of Paradigm D, which are described in the example in Section 9, below. Interestingly, rchd036 is not induced by shear stress, as indicated by the lack of any band after either 1 hr. or 6 hr. of treatment (FIG. 33). This result provides an example of an IL-1-inducible endothelial cell gene that is not regulated by shear stress, indicating that these induction pathways can be separated, and may provide for drugs with greater specificity for the treatment of inflammation and atherosclerosis. The DNA sequence was obtained from subclones of amplified DNA (FIG. 18), and a search of the database revealed no sequence similarities. A PCR amplification experiment determined that the rchd036 gene is located on human chromosome 15.

9. EXAMPLE: IDENTIFICATION OF GENES DIFFERENTIALLY EXPRESSED IN RESPONSE TO PARADIGM D: ENDOTHELIAL CELL SHEAR STRESS

According to the invention, differential display was used to detect genes that are differentially expressed in endothelial cells that were subjected to fluid shear stress in vitro. Shear stress is thought to be responsible for the prevalence of atherosclerotic lesions in areas of unusual circulatory flow. Using the method of Paradigm D, four bands with novel DNA sequences were identified.

rchd502 is homologous to rat matrin F/G mRNA sequence (Hakes, et al., 1991, Proc. Natl. Acad. Sci. U.S.A. 88:6186–6190. This rat gene has been shown to encode a protein which functions as a prostaglandin transporter, and has been designated PGT (Kanai et al., 1995, Science 268: 866–869). In fact, the sequences in rchd502 encode the homologous twelve transmembrane domains found in the PGT gene. Furthermore, rchd502 was demonstrated to be up-regulated by shear-stress but not by IL-1. It therefore provides an excellent novel tool for diagnosis and treatment of cardiovascular disease.

The complete sequence of the rchd523 gene reveals that it encodes a novel G protein-coupled receptor protein, consisting of 375 amino acids and seven transmembrane domains. At the amino acid level, rchd523 is 40% indentical to the Angiotensin II receptor. The discovery of such a novel protein is particularly useful in designing treatments as well as diagnostic and monitoring systems for cardiovascular disease. In carrying out signal transduction, G proteins play an important early role in the pathways that cause changes in cellular physiology. The rchd523 gene product, therefore, provides an excellent target for intervention in the treatment of cardiovascular disease.

The sequence of the coding region for rchd528 was partially determined. Sequence alignment revealed that the partial rchd528 sequence contains an extracellular domain with particularly strong homology to epidermal growth factor (EGF) repeats.

Furthermore, as transmembrane proteins, the rchd502, rchd523, and rchd528 gene products can be readily accessed or detected on the endothelial cell surface by other compounds. They provide, therefore, excellent targets for detection of cardiovascular disease states in diagnostic systems, as well as in the monitoring of the efficacy of compounds in clinical trials. Furthermore, the extracellular domains of these four gene products provide especially efficient screening systems for identifying compounds that bind to them. Such compounds, can be useful in treating cardiovascular disease by modulating the activity of the transmembrane gene products.

The sequence of the complete coding region of the rchd534 gene was also obtained. The rchd534 gene encodes a novel protein consisting of 235 amino acids, homologous to the Drosophila gene Mothers against decapentaplegic (Mad) (Sekelsky et al., 1995, Genetics 139: 1347–1358). The rchd534 gene is also significantly similar to a sequence of unknown function from *Caenorhabditis elegans,* identified in the *C. elegans* genome project (Wilson, et al., 1994, Nature 368: 32–38). MAD is in the same pathway as Decapentaplegic (dpp), which is a Drosophila homolog of bone morphogenic protein-4/Transforming growth factor-β (TGF-β).

Also using the method of Paradigm D, the previously identified human prostaglandin endoperoxide synthase type II, also known as cyclooxygenase II (COX II), was identified (band rchd505). This gene was previously known to be involved in inflammation, and to be up-regulated by IL-1 (Jones et al., 1993, J. Biol. Chem. 268: 9049–9054), but its up-regulation by shear stress was previously unknown. This result confirmed the general effectiveness of the techniques used according to the invention in the detection of genes involved cardiovascular disease.

The sequence of another up-regulated gene, designated as rchd530, was shown to be identical to the previously identified human manganese superoxide dismutase gene (MnSOD). The up-regulation of MnSOD under shear stress was not previously known.

The up-regulation of these six genes in shear stressed endothelial cells provides a fingerprint for the study of cardiovascular diseases, including but not limited to atherosclerosis, ischemia/reperfusion, hypertension, and restenosis. The fact that one of these genes, rchd502, is not up-regulated under Paradigm C (IL-1 induction) provides an extremely useful means of distinguishing and targeting physiological phenomena specific to shear stress.

The importance of the induction of these genes in endothelial cells under disease conditions was further analyzed by testing the effect of estrogen on their expression. Studies in postmenopausal women on estrogen replacement therapy and in animal models have demonstrated that estrogen has an atheroprotective effect in reducing incidence of coronary artery disease (Science 269:771–773, 1995). While these studies demonstrate that estrogen has an effect in the liver in reducing LDL levels and increasing HDL levels, these lipoprotein changes are not thought to be responsible for all of the cardioprotective effects of estrogen.

The identification of target genes that are differentially expressed under certain disease conditions provides for further analysis of the effect of estrogen on cardiovascular disease. The effect of estrogen on target gene expression in endothelial cells was, therefore, compared to particular paradigm expression patterns. Specifically, given that the estrogen receptor is a transcription factor (Kumar and Chambon, Cell 55:145–156, 1988), genes that are induced by shear stress were examined for regulation by estrogen in HUVEC's. In addition to estrogen, treatment with estrogen receptor agonists/antagonists tamoxifen (Grainger et al., Nature Medicine 1:1067–1073, 1995) and raloxifene (Black et al., J. Clin. Invest. 93:63–69, 1994), which also have been reported to have cardioprotective effects, were examined. The results demonstrate that rchd528, which is up-regulated by shear stress, is also up-regulated by estrogen, and suggest that shear stress and estrogen may play similar roles in cardiovascular disease.

9.1. MATERIALS AND METHODS

Primary cultures of HUVEC's were established from normal term umbilical cords as described (In Progress in Hemostasis and Thrombosis, Vol. 3, P. Spaet, editor, Grune & Stratton Inc., New York, 1–28). Cells were grown in 20% fetal calf serum complete media (Luscinskas 1989, J. Immunol. 142: 2257–2263). and passaged 1–3 times before shear stress induction.

For induction, second passage HUVEC's were plated on tissue culture-treated polystyrene and subjected to 10 dyn/ $cm^2$ laminar flow for 1 and 6 hr. as described (Nagel et al., 1994, J. Clin. Invest. 94: 885–891) or 3–10 dyn/ $cm^2$ turbulent flow as previously described (Davis et al., 1986 Proc. Natl. Acad. Sci. U.S.A. 83: 2114–2117).

To examine the effect of estrogen on target gene expression, HUVEC's were cultured in serum free endothelial cell basal medium supplemented with lug/ml insulin, 1 ug/ml transferrin, 50 ug/ml gentamycin, and 200 ug/ml fatty acid-free BSA. Cells were treated with either estradiol, tamoxifen, or raloxifene at 1 nm final concentration for 4 or 16 hours before lysis and RNA isolation. For rchd528, the DNA fragment comprising bases 1600–2600 was used as a probe in Northern analysis.

RNA was isolated as described, above, in Section 6.1. Differential display, Northern analysis, RT-PCR, subcloning, and DNA sequencing were carried out as described, above, in Section 6.1.2, except that Northern blot hybridizations were carried out as described, above, in Section 8.1.

cDNAs containing larger portions or complete coding regions of the genes were obtained either by RACE, or by probing cDNA libraries, or both. The RACE procedure was carried out using a kit according to the manufacturer's instructions (Clontech, Palo Alto, Calif.; see also: Chenchik, et al., 1995, CLONTECHniques (X) 1: 5–8; Barnes, 1994, Proc. Natl. Acad. Sci. USA 91: 2216–2220; and Cheng et al., Proc. Natl. Acad. Sci. USA 91: 5695–5699). Primers were designed based either on amplified sequences, or on sequences obtained from isolates from the cDNA libraries. Template mRNA was isolated from shear stressed HUVEC's.

Amplified sequences, which contained portions of the genes, were subcloned and then used individually to retrieve cDNAs encoding the corresponding gene within cDNA libraries. Probes were prepared by isolating the subcloned insert DNA from vector DNA and labeling with $^{32}p$ as described above in Section 6.1.2. The libraries used included individual human heart, human pancreas, and human lung cDNA libraries, (Clontech, Palo Alto, Calif.); and a cDNA library prepared from mRNA which was isolated from shear stressed HUVEC's as described in this section, above. The HUVEC cDNA library was produced according to well-known methods (Sambrook et al., 1989, supra), using the bacteriophage X-ZAP vector (Stratagene, La Jolla, Calif.). Libraries were screened by each respective probe using well-known methods (Sambrook et al., 1989, supra). Plaques from the libraries that were detected by the probes were isolated and the cDNA insert within the phage vector was sequenced.

Determination of chromosomal location was carried out according to the method described in Section 6.1.3, above.

The primers used for rchd523 were (for-atgccgtgtgggttagtc; SEQ ID NO:28) and (rev-attttatgggaaggtttttaca SEQ ID NO:29); and for rchd534 were (for-cttttctgcgtctcccat; SEQ ID NO:29) and (rev-agacatcagaaactccaacc; SEQ ID NO:43).

Northern blot analyis of RNA extracted from various human organs and tissues was performed using commercially available pre-blotted filters (Clontech, Palo Alto, Calif.).

9.2. RESULTS

HUVEC's were subjected to laminar shear stress for 1 r 6 hr. and compared to static control cells in differential display. As shown in FIG. 19, a band (rchd502) is identified which is found in lanes 5,6 (6 hr.) but not in lanes 1,2 (control). This band was excised, amplified, and sequenced. Northern analysis using amplified rchd502 sequences revealed a 4.5 kb band that is up-regulated at 6 hr. compared to controls (FIG. 20). When rchd502 probe was hybridized to a Northern blot prepared from IL-1 induced endothelial cells, up-regulation of a 4.5 kb band is not seen (FIG. 21). This result provides the first example of a shear stress-inducible endothelial cell gene that is not regulated by IL-1, indicating that these induction pathways can be separated, and may provide for drugs with greater specificity for the treatment of inflammation and atherosclerosis. The sequence of the amplified region of rchd502 was used to design probes for cloning the entire gene.

Both 5' and 3' RACE reactions were carried out to obtain a 2.2 kb cDNA containing the entire coding sequence of the rchd502 gene. Based on the sequence information from RACE, a phage clone was isolated from a human pancreas library which contains all but the first 200 base pairs of the rchd502 coding region. This clone was designated pFCHD502SF. The remaining 200 base pairs were obtained through amplification from a human lung library by PCR with specific primers. A fragment comprising base pairs 1-265 of the rchd502 gene was subcloned into the TA cloning vector to produce plasmid pFCHD502SJ. Thus, rchd502 is represented by two subclones, pFCHD502SJ comprising base pairs 1-265, and pFCHD502SF comprising base pairs 201 through the 3' end of the coding region, including 3' untranslated sequence.

The complete sequence encompassing the entire coding region is shown in FIGS. 22A–D. rchd502 shows strong homology (81.4%) to the rat PGT gene, which encodes a prostaglandin transporter (Kanai et al., 1995, supra). It contains twelve transmembrane (TM) domains. The approximate bounds of each of the twelve TM domains are as follows:

TM1: about amino acid 31 to about amino acid 52.

TM2: about amino acid 68 to about amino acid 89.

TM3: about amino acid 102 to about amino acid 121.

TM4: about amino acid 173 to about amino acid 194.

TM5: about amino acid 206 to about amino acid 227.

TM6: about amino acid 259 to about amino acid 280.

TM7: about amino acid 315 to about amino acid 337.

TM8: about amino acid 366 to about amino acid 385.

TM9: about amino acid 403 to about amino acid 423.

TM10: about amino acid 510 to about amino acid 530.

TM11: about amino acid 555 to about amino acid 575.

TM12: about amino acid 607 to about amino acid 627.

Shear stress band rchd505 decreased 1 hr. and 6 hr. after shear stress, as compared to untreated control cells (FIG. 23). Northern analysis revealed differential expression except that rchd505 was up-regulated after 1 hr. and 6 hr. shear stress treatment (FIG. 24). This same band was similarly up-regulated in cells treated with IL-1 according to Paradigm C (FIG. 25). Sequence analysis revealed that rchd505 is the previously characterized human endoperoxide synthase type II, also known as cyclooxygenase II (COX II).

rchd523 was detected under differential display as a band up-regulated after 1 hr. and 6 hr. shear stress treatment (FIG. 26). The 6 hr. up-regulation of rchd523 was confirmed by RT-PCR using rchd523 primers for-atgccgtgtgggttagtc (SEQ ID NO:28)/rev-attttatgggaaggtttttaca (SEQ ID NO:29) and human actin control primers for-accctgaagtaccccat (SEQ ID NO:16)/rev-tagaagcatttgcggtg (SEQ ID NO: 17). Amplified rchd523 sequences were subcloned, and an isolate was sequenced and designated pRCHD523. The RACE procedure was used to obtain a 2.5 kb cDNA containing the entire coding sequence of the rchd523 gene. The cDNA isolate containing the complete coding sequence of rchd523 is designated pFCHD523. Sequence analysis revealed that the rchd523 gene product encodes a novel G protein-coupled receptor, consisting of 375 amino acids and seven transmembrane domains. At the amino acid level, rchd523 is 40% indentical to the Angiotensin II receptor. A PCR amplification experiment determined that the rchd523 gene is located on human chromosome 7.

rchd528 was also detected as an up-regulated band after 1 hr. and 6 hr. shear stress treatment (FIG. 28). This result was confirmed by Northern analysis in which probes of rchd528 amplified sequence detected an approximately 8 kb message that was up-regulated moderately after 1 hr., and up-regulated very strongly after 6 hr. (FIG. 29). The amplified sequences were subcloned and sequenced. This sequence information was used for initial probing of a cDNA library to isolate the rchd528 gene.

The amplified sequence was used for initial probing of a shear stressed HUVEC cDNA library to isolate a partial clone of rchd528. The RACE procedure was then used in combination with probing a human heart cDNA library and PCR amplification to obtain overlapping clones encompassing the entire rchd528 coding region. The complete coding region of the rchd528 gene is contained in the following three plasmids each containing a segment of the rchd528 gene cloned into pBluescript: pFCHD528A, comprising nucleotides 1–1200; pFCHD528B, comprising nucleotides 237–2982; and pFCHD528C, comprising nucleotides 2982 through the 3' end of the coding region. The DNA sequence comprising the complete coding region of the rchd528 gene is shown in FIGS. 30A–D.

Based on homology to a number of different proteins, the rchd528 gene product was shown to contain an extracellular domain comprising the epidermal growth factor (EGF) repeat motif. The approximate bounds of the EGF repeat are from about amino acid 1089 to about amino acid 1122. There is a signal peptide domain extending from about amino acid 5 to about amino acid 28. Also, there is a transmembrane domain extending from about amino acid 1348 to about amino acid 1370. In addition, there is an asparagine hydroxylation site consensus sequence from about amino acid 1140 to about amino acid 1151. Northern blot analysis of mRNA isolated from a variety of human organs and tissues revealed that rchd528 is very highly expressed in the heart.

The effect of estrogen on the expression of rchd528 in endothelial cells was also examined. Northern blot analysis revealed significant up-regulation of rchd528 after overnight treatment with estrogen compared to control cells.

A band designated rchd530 corresponded to a sequence strongly up-regulated in HUVECs after six hours of shear stress. This up-regulation is greater for laminar shear stress than for turbulent shear stress. Sequence analysis revealed that rchd530 is identical to human manganese superoxide dismutase (MnSOD). The induction of MnSOD by shear stress was not previously known. MnSOD was also demonstrated to be induced by six hours of treatment with IL-1.

rchd534 also was detected as being up-regulated in response to shear stress. Northern analysis revealed that rchd534 is strongly induced after 6 hours of shear stress treatment (FIG. 33). The amplified sequences were subcloned, sequenced, and re-isolated for use as a probe for retrieving full-length rchd534 cDNA. A 3.3 kb λ-ZAP clone was sequenced to reveal full-length rchd534 cDNA (FIGS. 34A–D). This clone containing the entire coding region the rchd534 gene was designated pFCHD534. The encoded protein consists of 235 amino acids. A PCR amplification experiment determined that the rchd524 gene is located on human chromosome 15.

An initial comparison with sequences in the database revealed no homologies between rchd534 and any known DNA sequences. A subsequently performed search revealed that rchd534 is a homolog of the Drosophila gene Mothers against decapentaplegic (Mad) (Sekelsky et al., 1995, Genetics 139: 1347–1358), and is also significantly similar to a sequence of unknown function from *Caenorhabditis elegans,* identified in the *C. elegans* genome project ((Wilson, et al., 1994, Nature 368: 32–38).

rchd534 was also shown not to be regulated by IL-1 when tested under the conditions of Paradigm C, as described in Section 8, above. Just like rchd502, rchd534 is an example of a shear stress-inducible endothelial cell gene that is not regulated by IL-1, confirming that these induction pathways can be separated, and may provide for drugs with greater specificity for the treatment of inflammation and atherosclerosis.

10. EXAMPLE: USE OF GENES UNDER PARADIGM A AS SURROGATE MARKERS IN CLINICAL TRIALS

According to the invention, the fingerprint profile derived from any of the paradigms described in Sections 5.1.1.1 through 5.1.1.6 may be used to monitor clinical trials of drugs in human patients. The fingerprint profile, described generally in Section 5.5.4, above, indicates the characteristic pattern of differential gene regulation corresponding to a particular disease state. Paradigm A, described in Section 5.1.1.1, and illustrated in the example in Section 6, above, for example, provides the fingerprint profile of monocytes under oxidative stress. This profile gives an indicative reading, therefore, of the physiological response of monocytes to the uptake of oxidized LDL. Accordingly, the influence of anti-oxidant drugs on the oxidative potential may be measured by performing differential display on the monocytes of patients undergoing clinical tests.

10.1.TREATMENT OF PATIENTS AND CELL ISOLATION

Test patients may be administered compounds suspected of having anti-oxidant activity. Control patients may be given a placebo.

Blood may be drawn from each patient after a 12 hour period of fasting and monocytes may be purified as described, above, in Section 7.1.1. RNA may be isolated as described in Section 6.1.1, above.

10.2.ANALYSIS OF SAMPLES

RNA may be subjected to differential display analysis as described in Section 6.1.2, above. A decrease in the physiological response state of the monocytes is indicated by a decreased intensity of those bands that were up-regulated by oxidized LDL under Paradigm A, and an increased intensity of those bands that were down-regulated by oxidized LDL under Paradigm A, as described in Section 6.2, above.

11. EXAMPLE: IMAGING OF A CARDIOVASCULAR DISEASE CONDITION

According to the invention, differentially expressed gene products which are localized on the surface of affected tissue may be used as markers for imaging the diseased or damaged tissue. Conjugated antibodies that are specific to the differentially expressed gene product may be administered to a patient or a test animal intravenously. This method provides the advantage of allowing the diseased or damaged tissue to be visualized non-invasively.

For the purposes of illustration, this method is described in detail for the rchd523 gene product. The principles and techniques can be applied to any identified transmembrane target gene product, including, for example, the rchd502 and rchd528 gene products.

11.1. MONOCLONAL CONJUGATED ANTIBODIES

The differentially expressed surface gene product, such as the rchd523 gene product, is expressed in a recombinant host and purified using methods described in Section 5.4.2, above. Preferably, a protein fragment comprising one or more of the extracellular domains of the rchd523 product is produced. Once purified, it is be used to produce $F(ab')_2$ or Fab fragments, as described in Section 5.4.3, above. These fragments are then labelled with technetium-99m ($^{99m}Tc$) using a conjugated metal chelator, such as DTPA as described in section 5.8.3, above.

11.2. ADMINISTRATION AND DETECTION OF IMAGING AGENTS

Labeled MAb may be administered intravenously to a patient being diagnosed for atherosclerosis, restenosis, or ischemia/reperfusion. Sufficient time is allowed for the detectably-labeled antibody to localize at the diseased or damaged tissue site (or sites), and bind to the rchd523 gene product. The signal generated by the label is detected by a photoscanning device. The detected signal is then converted to an image of the tissue, revealing cells, such as endothelial cells, in which rchd523 gene expression is up-regulated.

12. EXAMPLE: SCREENING FOR LIGANDS OF THE rchd 523 GENE PRODUCT AND ANTAGONISTS OF rchd523 GENE PRODUCT-LIGAND INTERACTION The rchd523 gene product is a member of the G protein-coupled receptor protein family, containing multiple transmembrane domains. The receptor binding activity of this protein family is detected by assaying for $Ca^{2+}$ mobility through the membrane of cells in which the receptor gene is expressed. This assay, described below, is used to identify ligands that bind to the rchd523 gene product receptor. Establishing this ligand-receptor activity then provides for a screen in which antagonists of the ligand-receptor interaction are identified. An antagonist is detected by its ability to inhibit the $Ca^{2+}$ mobility induced by ligand-receptor binding. Such antagonists, therefore, provide compounds that are useful in the treatment of cardiovascular disease, by counteracting the activity of the product of this target gene which is up-regulated in the disease state.

Binding of ligand to the rchd523 gene product is measured as follows. The cDNA containing the entire coding region of the rchd523 gene is removed from pFCHD523 and placed under the control of a promoter that is highly expressed in mammalian cells in an appropriate expression vector. The resulting construct is transfected into myeloma cells, which are then loaded with FURA-2 or INDO-1 by standard techniques. Ligands are added to the cell culture to test their ability to bind to the rchd523 receptor in a manner that triggers signal transduction, as measured by $Ca^{2+}$ mobilization across the cell membrane. Mobilization of $Ca^{2+}$ induced by ligand is measured by fluorescence spectroscopy as described in Grynkiewicz et al., 1985, *J. Biol. Chem.* 260:3440. Ligands that react with the target gene product receptor domain are identified by their ability to produce a fluorescent signal. Their receptor binding activities are quantified and compared by measuring the level of fluorescence produced over background.

Candidate antagonists are then screened for their ability to interfere with ligand-receptor binding. Myeloma transfectants expressing rchd523 gene product are treated with ligand alone, and ligand in the presence of candidate antagonist. Candidate antagonists that cause a reduction in the fluorescence signal are designated antagonists of the ligand-rchd523 receptor interaction.

13. POLYCLONAL ANTIBODIES TO TARGET GENE PEPTIDE SEQUENCES

Peptide sequences corresponding to the indicated amino sequences of cDNAs were selected and submitted to Research Genetics (Huntsville, Ala.) for synthesis and antibody production. Peptides were modified as described (Tam, J. P., 1988, Proc. Natl. Acad. Sci. USA 85: 5409–5413; Tam, J. P., and Zavala, F., 1989, J. Immunol. Methods 124: 53–61; Tam, J. P., and Lu, Y. A., 1989, Proc. Natl. Acad. Sci. USA 86: 9084–9088), emulsified in an equal volume of Freund's adjuvant and injected into rabbits at 3 to 4 subcutaneous dorsal sites for a total volume of 1.0 ml (0.5 mg peptide) per immunization. The animals were boosted after 2 and 6 weeks and bled at weeks 4, 8, and 10. The blood was allowed to clot and serum was collected by centrifugation.

The peptides used are summarized below:

| | Amino Acids #'s | Sequence |
|---|---|---|
| rchd502 | | |
| fchd502.1 | 294–308 | DEARKLEEAKSRGSL (SEQ ID NO: 45) |
| fchd502.2 | 435–449 | SSIHPQSPACRRDCS (SEQ ID NO: 46) |
| fchd502.3 | 627–640 | RVKKNKEYNVQKAA (SEQ ID NO: 47) |
| rchd523 | | |
| fchd523.1 | 243–258 | RAHRHRGLRPRRQKAL (SEQ ID NO: 48) |
| fchd523.2 | 360–372 | IPDSTEQSDVRFS (SEQ ID NO: 49) |
| rchd528 | | |
| fchd528.1 | 1393–1410 | SPYAEYPKNPRSQEWGRE (SEQ ID NO: 50) |
| fchd528.2 | 1467–1481 | NPSFISDESRRRDYF (SEQ ID NO: 51) |
| rchd534 | | |
| fchd534.1 | 54–69 | EFSDASMSPDATKPSH (SEQ ID NO: 52) |
| fchd534.2 | 112–125 | LEQRSESVRRTRSK (SEQ ID NO: 53) |
| fchd534.3 | 182–197 | RSGLQHAPEPDAADGP (SEQ ID NO: 54) |

14. LOCALIZATION OF NOVEL GENES BY IN SITU HYBRIDIZATION

The expression of two target genes, rchd502 and rchd528, was examined by in situ hybridization. The expression was detected in human carotidendarterectomy samples, i.e., human cardiovascular tissue in a diseased state, taken from a living patient suffering from cardiovascular disease. The expression pattern for each gene was observed to be similar to the pattern detected for the positive control, which is known to be constitutively expressed in endothelial cells. These results provide further evidence of the role of both rchd502 and rchd528 in cardiovascular disease. The detection of high levels of expression of these target genes specifically within the endothelial cells of diseased tissues allows for more precise diagnosis, as well as more precise treatment methods, than simple detection of atherosclerotic lesion provides.

14.1 METHODS

7 μm paraffin embedded sections of human carotid endarterectomy samples were deparaffinized in xylenes, rehydrated through graded ethanol series and post-fixed with 4% PFA/PBS for 15 minutes. After washing with PBS, sections were digested with 2 μg/ml proteinase K at 37° for 15 minutes, and again incubated with 4% PFA/PBS for 10 minutes. Sections were then washed with PBS, incubated with 0.2N HCl for 10 minutes, washed with PBS, incubated with 0.25% acetic anhydride/1M triethanolamine for 10 minutes, washed with PBS and dehydrated with 70% ethanol and 100% ethanol.

Hybridizations were performed with $^{35}S$-radiolabeled ($5\times10^7$ cpm/ml) cRNA probes encoding 1) the 0.8 kB SmaI fragment segment of the coding region of the human von Willebrand factor gene, 2) a fragment containing portions of the novel gene rchd502 (sequence base pairs 3–1195, excluding bases 396–622), and 3) a fragment of the novel gene fchd528 (sequence base pairs 3718–6407) in the presence of 50% formamide, 10% dextran sulfate, 1× Denhardt's solution, 600 mM NaCl, 10 mM DTT, 0.25% SDS and 100 μmg/ml tRNA for 18 hours at 55°. After hybridization, slides were washed with 5× SSC at 550, 50% formamide/2× SSC at 55° for 30 minutes, 10 mM Tris-HCl(pH 7.6)/500 mM NaCl/1 mM EDTA (TNE) at 37° for 10 minutes, incubated in 10 μg/ml RNase A in TNE at 37° for 30 minutes, washed in TNE at 37° for 10 minutes, incubated once in 2× SSC at 50° for 30 minutes, and dehydrated with 70% ethanol and 100% ethanol. Localization of mRNA transcripts was detected by dipping slides in Kodak NBT-2 photoemulsion and exposing for 7 days at 4°, followed by development with Kodak Dektol developer. Slides were counterstained with Haemotoxylin and Eosin and photographed. Controls for the in situ hybridization experiments included the use of a sense probe which showed no signal above background levels.

14.2 RESULTS

The rchd502 and rchd528 genes each displayed a similar expression pattern to the positive control signal from von Willebrand factor, a constitutively expressed endothelial cell marker. Signal was detected for both rchd502 and rchd528 over most endothelial cells lining the luminal surface of the carotid artery, as was also observed for von Willebrand factor. None of the three genes examined showed expression in any other cell type present in the tissue, including smooth muscle cells and macrophages.

15. DEPOSIT OF MICROORGANISMS

The following microorganisms were deposited with the Agricultural Research Service Culture Collection (NRRL), Peoria, Ill., on Jan. 11, 1995 and assigned the indicated accession numbers:

| Microorganism | NRRL Accession No. |
|---|---|
| RCHD005 | B-21376 |
| RCHD024 | B-21377 |
| RCHD032 | B-21378 |
| RCHD036 | B-21379 |
| RCHD502 | B-21380 |
| RCHD523 | B-21381 |
| RCHD528 | B-21382 |

The following microorganisms were deposited with the Agricultural Research Service Culture Collection (NRRL), Peoria, Ill., on Jun. 6, 1995 and assigned the indicated accession numbers:

| Microorganism | NRRL Accession No. |
|---|---|
| FCHD523 | B-21458 |
| FCHD534 | B-21459 |

The following microorganisms were deposited with the American Type Culture Collection (ATCC), Rockville, Md., on Feb. 7, 1996, and assigned the indicated accession numbers:

| Microorganism | ATCC Accession No. |
|---|---|
| FCHD502SF | 69981 |
| FCHD502SJ | 69982 |

The following microorganisms were deposited with the American Type Culture Collection (ATCC), Rockville, Md., on Feb. 9, 1996, and assigned the indicated accession numbers:

| Microorganism | ATCC Accession No. |
|---|---|
| FCHD528A | 69985 |
| FCHD528B | 69986 |
| FCHD528C | 69987 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated polynucleotide comprising a nucleotide sequence (a) encoding a polypeptide having the amino acid sequence set forth in SEQ ID NO:40, or (b) encoding an rchd528 polypeptide whose sequence is encoded by the cDNAs contained in the plasmids pFCHD528A, pFCHD528B, and pFCHD528C, as deposited with the American Type Culture Collection as Accession Nos: 69985, 69986, and 69987, respectively.

2. An isolated polynucleotide comprising the nucleotide sequence of (a) the rchd528 cDNA shown in SEQ ID NO:7, or (b) the rchd528 cDNA contained in the plasmids pFCHD528A, pFCHD528B, and pFCHD528C, as deposited with the American Type Culture Collection as Accession Nos: 69985, 69986, and 69987, respectively.

3. An isolated polynucleotide comprising the nucleotide sequence of (a) the rchd528 polypeptide coding region from nucleotide residue number 19 to 4461 of SEQ ID NO:7, or (b) the polypeptide coding region of the rchd528 cDNA contained in the plasmids pFCHD528A, pFCHD528B, and pFCHD528C as deposited with the American Type Culture Collection as Accession Nos: 69985, 69986, and 69987, respectively.

4. An isolated polynucleotide comprising a nucleotide sequence that hybridizes under highly stringent conditions to the complement of the nucleotide sequence of claim 3.

5. A polynucleotide fragment that encodes the amino acid sequence set forth in SEQ ID NO:40, wherein the amino acid sequence lacks at least one of the following polypeptide segments: amino acids 5–28, 1089–1122, 1140–1151, 1348–1370, as set forth in SEQ ID NO:40.

6. A polynucleotide fragment that encodes the amino acid sequence set forth in SEQ ID NO:40, wherein the amino acid sequence lacks at least one of the polypeptide segments encoded by the following nucleotide sequences: nucleotides 31–102, 3283–3384, 3436–3471, 4060–4128, as set forth in SEQ ID NO:7.

7. A polynucleotide fragment that encodes one or more of the following polypeptide segments: amino acids 5–28, 1089–1122, 1140–1151, 1348–1370, as set forth in SEQ ID NO:40.

8. An isolated polynucleotide comprising one or more of the following nucleotide sequences: nucleotides 31–102, 3283–3384, 3436–3471, 4060–4128, as set forth in SEQ ID NO:7.

9. The isolated polynucleotide of claim 1, 2, 3, 4, 5, 6, 7, or 8 which is DNA.

10. The isolated polynucleotide of claim 3 which is cDNA.

11. The isolated polynucleotide of claim 3 which is genomic DNA.

12. The isolated polynucleotide of claim 1, 2, 3, 4, 5, 6, 7, or 8 which is RNA.

13. The isolated polynucleotide of claim 1, 2, 3, 4, 5, 6, 7, or 8 which further comprises a label.

14. A polynucleotide vector containing the polynucleotide of claim 1, 2, 3, 4, 5, 6, 7, or 8.

15. A polynucleotide expression vector containing the polynucleotide of claim 1, 2, 3, 4, 5, 6, 7, or 8 in operative association with a nucleotide regulatory element that controls expression of the polynucleotide in a host cell.

16. A cultured genetically engineered host cell containing the polynucleotide of claim 1, 2, 3, 4, 5, 6, 7, or 8.

17. A cultured genetically engineered host cell containing the polynucleotide of claim 1, 2, 3, 4, 5, 6, 7, or 8 in operative association with a nucleotide regulatory element that controls expression of the polynucleotide in the host cell.

18. The genetically engineered host cell of claim 17 which is prokaryotic.

19. The genetically engineered host cell of claim 17 which is eukaryotic.

20. A method of producing a polypeptide rchd528 gene product, comprising the steps of:

(a) growing the genetically engineered host cell of claim 18 in a culture; and (b) collecting the polypeptide gene product from the culture.

21. A method of producing a polypeptide rchd528 gene product, comprising the steps of:

(a) growing the genetically engineered host cell of claim 19 in a culture; and (b) collecting the polypeptide gene product from the culture.

* * * * *

UNITED STATES PATENT AND TRADEMARK OFFICE
CERTIFICATE OF CORRECTION

PATENT NO. : 5,849,578

DATED : December 15, 1998

INVENTORS : DEAN A. FALB

It is certified that an error appears in the above-identified patent and that said Letters Patent is hereby corrected as shown below:

TITLE PAGE, in the Title, after "CARDIOVASCULAR" insert --DISEASE--;

TITLE PAGE, in Section [75], change "Massachusetts" to --Wellesley--;

CLAIM 10, Line 1, change "3" to --9--; and

CLAIM 11, Line 1, change "3" to --9--.

Signed and Sealed this

Fourteenth Day of September, 1999

Attest:

Q. TODD DICKINSON

*Attesting Officer* *Acting Commissioner of Patents and Trademarks*

UNITED STATES PATENT AND TRADEMARK OFFICE

CERTIFICATE OF CORRECTION

PATENT NO. : 5,849,578
DATED : December 15, 1998
INVENTOR(S) : Dean A Falb *et al.*

It is certified that error appears in the above-identified patent and that said Letters Patent is hereby corrected as shown below:

Column 1,
After line 11, insert the following:
-- *Statement as to Rights to Inventions Made Under Federally-Sponsored Research and Development*

Part of the work performed during development of this invention utilized U.S Government funds. The U.S. Government has certain rights in this invention. This work was supported by National Institutes of Health Grants P50-HL56985 and R37-HL51150. --

Signed and Sealed this

Nineteenth Day of March, 2002

*Attest:*

JAMES E. ROGAN

*Attesting Officer*

*Director of the United States Patent and Trademark Office*

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
( A ) LENGTH: 288 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( x i ) SEQUENCE DESCRIPTION: SEQ ID NO:1:

```
GGCTTAGATG CAGCCTGCAA ATTAAACTTT GATTTTTCAT CTTGTGAAAG CAGTCCTTGT    60
TCCTATGGCC TAATGAACAA CTTCCAGGTA ATGAGTATGG TGTCAGGATT TACACCACTA   120
ATTTCTGCAG GTATATTTTC AGCCACTCTT TCTTCAGCAT TAGCATCCCT AGTGAGTGCT   180
CCCAAAATAT TTCAGGCTCT ATGTAAGGAC AACATCTACC CAGCTTTCCA GATGTTTGCT   240
AAAGGTTATG GGAAAAATAA TGAACCTCTT CGTGGCTGCA TCTAAGCC                288
```

( 2 ) INFORMATION FOR SEQ ID NO:2:

( i ) SEQUENCE CHARACTERISTICS:
( A ) LENGTH: 178 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO -continued ( x i ) SEQUENCE DESCRIPTION: SEQ ID NO:2:

AAAAATAAAT AAATTAAAGT CTGAGACCAA TTTGCCACTG TGAATATAAG CACATTAACC 60
CCAGGAGGAG CCAAGAACTA CACAAACCTC TCTATGAGAA TTTACCAGTC TTCTTTCATT 120
TGGCAAGAAA AAGCTCAGGA AAATTTGCTT GTTTAAATTC TATGAGCCTA GTCTATGG 178

( 2 ) INFORMATION FOR SEQ ID NO:3:

( i ) SEQUENCE CHARACTERISTICS:
( A ) LENGTH: 101 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( x i ) SEQUENCE DESCRIPTION: SEQ ID NO:3:

GGGTAATTCA TTAATTACAC TTTAAAATTG GAAAGTGGGA TAAGAAATCT AAAGTAAACC 60
AGCTTATCTT TGAAACAATA TTATTTTGAA ATTGGCTTTA A 101

( 2 ) INFORMATION FOR SEQ ID NO:4:

( i ) SEQUENCE CHARACTERISTICS:
( A ) LENGTH: 184 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( x i ) SEQUENCE DESCRIPTION: SEQ ID NO:4:

GGCTTGGTGG TGATGCCTAC AAGAAATGTT TACATACAAA CACTCTATAC ATCTAACTCC 60
CGAAAAAGGA CCAGCTATTT CGGCAACAGA AAAAAGACAA GCATTTCAGA GGAGCGTTGC 120
TTTCCTTAAA GACCTAACTC ACTTAAGTCT TACAAACAGA AATAACAAGG AGGACAATTT 180
TCTA 184

( 2 ) INFORMATION FOR SEQ ID NO:5:

( i ) SEQUENCE CHARACTERISTICS:
( A ) LENGTH: 2042 base pairs
( B ) TYPE: nucleic acid
( C ) STRANDEDNESS: both
( D ) TOPOLOGY: unknown ( i i ) MOLECULE TYPE: cDNA ( x i ) SEQUENCE DESCRIPTION: SEQ ID NO:5:

ATGGGGCTCC TGCCCAAGCT CGGCGCGTCC CAGGGCAGCG ACACCTCTAC TAGCCGAGCC 60
GGCCGCTGTG CCCGCTCGGT CTTCGGCAAC ATTAAGGTGT TTGTGCTCTG CCAAGGCCTC 120
CTGCAGCTCT GCCAACTCCT GTACAGCGCC TACTTCAAGA GCAGCCTCAC CACCATTGAG 180
AAGCGCTTTG GGCTCTCCAG TTCTTCATCG GGTCTCATTT CCAGCTTGAA TGAGATCAGC 240
AATGCCATCC TCATCATCTT TGTCAGCTAC TTTGGCAGCC GGGTGCACCG TCCACGTCTG 300
ATTGGCATCG GAGGTCTCTT CCTGGCTGCA GGTGCCTTCA TCCTCACCCT CCCACACTTC 360
CTCTCCGAGC CCTACCAGTA CACCTTGGCC AGCACTGGGA ACAACAGCCG CTTGCAGGCC 420
GAGCTCTGCC AGAAGCATTG GCAGGACCTG CCTCCCAGTA AGTGCCACAG CACCACCCAG 480

-continued

```
AACCCCCAGA AGGAGACCAG CAGCATGTGG GGCCTGATGG TGGTTGCCCA GCTGCTGGCT 540
GGCATCGGGA CAGTGCCTAT TCAGCCATTT GGGATCTCCT ATGTGGATGA CTTCTCAGAG 600
CCCAGCAACT CGCCCCTGTA CATCTCCATC TTATTTGCCA TCTCTGTATT TGGACCGGCT 660
TTCGGGTACC TGCTGGGCTC TGTCATGCTG CAGATCTTTG TGGACTATGG CAGGGTCAAC 720
ACAGCTGCAG TTAACTTGGT CCCGGGTGAC CCCCGATGGA TTGGAGCCTG GTGGCTAGGC 780
CTGCTCATTT CTTCAGCTTT ATTGGTTCTC ACCTCTTTCC CCTTTTTTTT CTTCCCTCGA 840
GCAATGCCCA TAGGAGCAAA GAGGGCTCCT GCCACAGCAG ATGAAGCAAG GAAGTTGGAG 900
GAGGCCAAGT CAAGAGGCTC CCTGGTGGAT TTCATTAAAC GGTTTCCATG CATCTTTCTG 960
AGGCTCCTGA TGAACTCACT CTTCGTCCTG GTGGTCCTGG CCCAGTGCAC CTTCTCCTCC 1020
GTCATTGCTG GCCTCTCCAC CTTCCTCAAC AAGTTCCTGG AGAAGCAGTA TGGCACCTCA 1080
GCAGCCTATG CCAACTTCCT CATTGGTGCT GTGAACCTCC CTGCTGCAGC CTTGGGGATG 1140
CTGTTTGGAG GAATCCTCAT GAAGCGCTTT GTTTTCTCTC TACAAGCCAT TCCCCGCATA 1200
GCTACCACCA TCATCACCAT CTCCATGATC CTTTGTGTTC CTTTGTTCTT CATGGGATGC 1260
TCCACCCCAA CTGTGGCCGA AGTCTACCCC CCTAGCACAT CAAGTTCTAT ACATCCGCAG 1320
TCTCCTGCCT GCCGCAGGGA CTGCTCGTGC CCAGATTCTA TCTTCCACCC GGTCTGTGGA 1380
GACAATGGAA TCGAGTACCT CTCCCCTTGC CATGCCGGCT GCAGCAACAT CAACATGAGC 1440
TCTGCAACCT CCAAGCAACT GATCTATTTG AACTGCAGCT GTGTGACCGG GGGATCCGCT 1500
TCAGCAAAGA CAGGATCGTG CCCTGTCCCC TGTGCCCACT TCCTGCTCCC GGCCATCTTC 1560
CTCATCTCCT TCGTGTCCCT GATAGCCTGC ATCTCCCACA ACCCCCTCTA CATGATGGTT 1620
CTGCGTGTGG TGAACCAGGA GGAAAAGTCA TTTGCCATCG GGGTGCAGTT CTTGTTGATG 1680
CGCTTGCTGG CCTGGCTGCC ATCTCCAGCC CTCTATGGCC TCACCATTGA CCACTCCTGC 1740
ATCCGGTGGA ACTCGCTGTG CTTGGGGAGG CGAGGGGCCT GCGCCTACTA TGACAACGAT 1800
GCTCTCCGAG ACAGGTACCT GGGCCTGCAG ATGGGCTACA AGGCGCTGGG CATGCTGCTG 1860
CTTTGCTTCA TCAGCTGGAG GGTGAAGAAG AACAAGGAGT ACAACGTGCA GAAGGCGGCA 1920
GGCCTCATCT GACCCCACCC TGGGCCACTG YCCTGCTCCA GAGAGTGGAC CTTGACTCYT 1980
CCACACCTGC CTATACTCAC TAATGTTAAC ACGTCATTTC CTKTTTGTAT TTTTAAAMAA 2040
GA 2042
```

( 2 ) INFORMATION FOR SEQ ID NO:6:

( i ) SEQUENCE CHARACTERISTICS:
( A ) LENGTH: 2582 base pairs
( B ) TYPE: nucleic acid
( C ) STRANDEDNESS: both
( D ) TOPOLOGY: unknown ( i i ) MOLECULE TYPE: cDNA ( i i i ) HYPOTHETICAL: NO ( x i ) SEQUENCE DESCRIPTION: SEQ ID NO:6:

```
GGCTTACCAT CGATGCGGCC GCGGATCCAG GGCTCAGAGG GAGGACGCAC CCGCCAGCCA 60
GCCGGGAACC TTCCCTCGCG GGCTCCCAGG GCGGGTCTCT TCCTCTCTCT AGCCCTGCTC 120
AGGCATTCGG CAGGTCCAGC AGAGGTACAC CTCCTGCAGC GGGTTCCAAG TGCACCTCCA 180
GCCTGATGGA CCTGACCAAG GAGGCTTCCA GGAGCACAGA AGGGGCTGCA ACCCAGGTAC 240
CCAGAGAGTG AGCAGCTCCA CGCGGGACTG TGCACGGTGG CCGACACCCG CAGGGACGCC 300
CACCGGACGA GCACGCGGAG GGCCCTCGCC TCCACGGATG CACCATGCCG GTGTGAGGAG 360
```

-continued

```
CATCTGTTCT TCCCACTCTC TGCAGTTAAC AAACCCAACC CAAACCACCA CAGGTGCTCC   420
TCCTGGGGAG TTTCCTGTCT GACAAATGCC AGGCTCACTT CAAGGAGAAT CACGCTTCTT   480
TCTAAAGATG GATTCACCAT TTAAAACAGA GCTCTGGGAG CCTTTCGGCA AATCTTGAAA   540
GCTGCACGGC GCAGAGACAT GGATGTGACT TCCCAAGCCC GGGGCGTAGG CCTGGAGATG   600
TACCCAGGCA CCGCGCAGCC TGCGGCCCCC AACACCACCT CCCCCGAGCT CAACCTGTCC   660
CACCCGCTCC TGGGCACCGC CCTGGCCAAT GGGACAGGTG AGCTCTCGGA GCACCAGCAA   720
TACGTGATCG GCCTGTTCCT CTCGTGCCTC TACACCATCT TCCTCTTCCC CATCGGCTTT   780
GTGGGCAACA TCCTGATCCT GGTGGTGAAC ATCAGCTTCC GCGAGAAGAT GACCATCCCC   840
GACCTGTACT TCATCAACCT GGCGGTGGCG GACCTCATCC TGGTGGCCGA CTCCCTCATT   900
GAGGTGTTCA ACCTGCACGA GCGGTACTAC GACATCGCCG TCCTGTGCAC CTTCATGTCG   960
CTCTTCCTGC GGGTCAACAT GTACAGCAGC GTCTTCTTCC TCACCTGGAT GAGCTTCGAC  1020
CGCTACATCG CCCTGGCCAG GGCCATGCGC TGCAGCCTGT TCCGCACCAA GCACCACGCC  1080
CGGCTGAGCT GTGGCCTCAT CTGGATGGCA TCCGTGTCAG CCACGCTGGT GCCCTTCACC  1140
GCCGTGCACC TGCAGCACAC CGACGAGGCC TGCTTCTGTT TCGCGGATGT CCGGGAGGTG  1200
CAGTGGCTCG AGGTCACGCT GGGCTTCATC GTGCCCTTCG CCATCATCGG CCTGTGCTAC  1260
TCCCTCATTG TCCGGGTGCT GGTCAGGGCG CACCGGCACC GTGGGCTGCG GCCCCGGCGG  1320
CAGAAGGCGC TCCGCATGAT CCTCGCAGTG GTGCTGGTCT TCTTCGTCTG CTGGCTGCCG  1380
GAGAACGTCT TCATCAGCGT GCACCTCCTG CAGCGGACGC AGCCTGGGGC CGCTCCTTGC  1440
AAGCAGTCTT TCCGCCATGC CCACCCCCTC ACGGGCCACA TTGTCAACCT CGCCGCCTTC  1500
TCCAACAGCT GCCTAAACCC CCTCATCTAC AGCTTTCTCG GGGAGACCTT CAGGGACAAG  1560
CTGAGGCTGT ACATTGAGCA GAAAACAAAT TTGCCGGCCC TGGACCGCTT CTGTCACGCT  1620
GCCCTGAAGG CCGTCATTCC AGACAGCACC GAGCAGTCGG ATGTGAGGTT CAGCAGTGCC  1680
GTGTAGACAG CCTTGGCCGC ATAGGCCCAG CCAGGGTGTG ACTCGGGAGC TGCACACACC  1740
TGGGTGGACA CAAGGCACGG CCACGTCATG TCTCTAAACT GCGGTCAGAT GTGGCTTCTG  1800
GCTCCTCGGG CCTCGCGAGG GTCACGCTTG CCTGGTCACC CTGGGGCTGC TTAGGAAACC  1860
TCAGGACTGG TCACCTTGCA CTCCTCACAC AGAATTGCTA CAATCCCAAA GCGCTCGCCC  1920
CGCAGGGTCC AAAGGCCAGC GGTGACCAGC CTGTCACCCA GCTCCTCCCC GCCAACCCTG  1980
CCTGCCGCTG CACCTGCCCG CTGCTGCAGG AAACATTTCT GACACCGTCG ACCAGGAAAG  2040
CCACACGGAG AGGCCACTGT GGGTGAAGCG CCTCAGTTAC ACAGGAACCC TAAAGCAAAT  2100
CTGCCACCGT GGGGGAACTG ACGCTGGAGA TGCAAGGTGC TGGTGGGTCT GAGCTGGACG  2160
TCGCGGTGTG TCCTCTGTGC CCACGGTCTG AGCTAGCTAG CGCACCGCCG AGTTAAAGAG  2220
GAGAAGGAAA ACATGCTGCT CTGGTGCACG CCTGAGCGTC CTCCATCTTC CAGGATGGCA  2280
GCAATGGCGC TGTGCGGCCT CACCAGGCCC ACGAGGAGCA GCAGCGCTCG GCCCGGAGCA  2340
GCAGGAAGGC CCCTCTGTGG AGCGCCCGCC GTCTGCTCCG GGGTGGTTCA GTCACTGCTT  2400
GTTGACATCA ACATGGCAAT TGCACTCATG TGGACTGGGA CCGTGCGAGC TGCCGTGTGG  2460
GTTAGTCGGG TGCCAGGACA ATGAAATACT CCAGCACCTG TGGCTGACGA ATTCGTTTCT  2520
ACAGAAGTAA CAGCTGGGGA CAACTGCGAT GATGATGTAA AAACCTTCCC ATAAAATAAG  2580
CC                                                                 2582
```

(2) INFORMATION FOR SEQ ID NO:7:

( i ) SEQUENCE CHARACTERISTICS:
( A ) LENGTH: 6407 base pairs
( B ) TYPE: nucleic acid
( C ) STRANDEDNESS: both
( D ) TOPOLOGY: unknown ( i i ) MOLECULE TYPE: cDNA ( x i ) SEQUENCE DESCRIPTION: SEQ ID NO:7:

CGGGCCCGCG CCGTCACCAT GGCCTCGCCG CGCGCCTCGC GGTGGCCGCC GCCGCTCCTG 60

CTGCTGTTGC TGCCGCTGCT GCTGCTGCCG CCGGCGGCCC CCGGGACGCG GGACCCGCCG 120

CCTTCCCCGG CTCGCCGCGC GCTGAGCCTG GCGCCCCTCG CGGGAGCGGG GCTGGAGCTG 180

CAGCTGGAGC GCCGCCCGGA GCGCGAGCCG CCGCCCACGC CGCCCCGGGA GCGCCGCGGG 240

CCCGCGACCC CCGGCCCCAG CTACAGGGCC CCTGAGCCAG GCGCCGCGAC ACAGCGGGGA 300

CCCTCCGGCC GGGCCCCCAG AGGCGGGAGC GCGGATGCTG CCTGGAAACA TTGGCCAGAA 360

AGTAACACTG AGGCCCATGT AGAAAACATC ACCTTCTATC AGAATCAAGA GGACTTTTCA 420

ACAGTGTCCT CCAAAGAGGG TGTGATGGTT CAGACCTCTG GGAAGAGCCA TGCTGCTTCG 480

GATGCTCCAG AAAACCTCAC TCTACTCGCT GAAACAGCAG ATGCTAGAGG AAGGAGCGGC 540

TCTTCAAGTA GAACAAACTT CACCATTTTG CCTGTTGGGT ACTCACTGGA GATAGCAACA 600

GCTCTGACTT CCCAGAGTGG CAACTTAGCC TCGGAAAGTC TTCACCTGCC ATCCAGCAGT 660

TCAGAGTTCG ATGAAAGAAT TGCCGCTTTT CAAACAAAGA GTGGAACAGC CTCGGAGATG 720

GGAACAGAGA GGGCGATGGG GCTGTCAGAA GAATGGACTG TGCACAGCCA AGAGGCCACC 780

ACTTCGGCTT GGAGCCCGTC CTTTCTTCCT GCTTTGGAGA TGGGAGAGCT GACCACGCCT 840

TCTAGGAAGA GAAATTCCTC AGGACCAGAT CTCTCCTGGC TGCATTTCTA CAGGACAGCA 900

GCTTCCTCTC CTCTCTTAGA CCTTTCCTCA CCTTCTGAAA GTACAGAGAA GCTTAACAAC 960

TCCACTGGCC TCCAGAGCTC CTCAGTCAGT CAAACAAAGA CAATGCATGT TGCTACCGTG 1020

TTCACTGATG GTGGCCCGAG AACGCTGCGA TCTTTGACGG TCAGTCTGGG ACCTGTGAGC 1080

AAGACAGAAG GCTTCCCCAA GGACTCCAGA ATTGCCACGA CTTCATCCTC AGTCCTTCTT 1140

TCACCCTCTG CAGTGGAATC GAGAAGAAAC AGTAGAGTAA CTGGGAATCC AGGGGATGAG 1200

GAATTCATTG AACCATCCAC AGAAAATGAA TTTGGACTTA CGTCTTTGCG TTGGCAAAAT 1260

GATTCCCCAA CCTTTGGAGA ACATCAGCTT GCCAGCAGCT CTGAGGTGCA AAATGGAAGT 1320

CCCATGTCTC AGACTGAGAC TGTGTCTAGG TCAGTCGCAC CCATGAGAGG TGGAGAGATC 1380

ACTGCACACT GGCTCTTGAC CAACAGCACA ACATCTGCAG ATGTGACAGG AAGCTCTGCT 1440

TCATATCCTG AAGGTGTGAA TGCTTCAGTG TTGACCCAGT TCTCAGACTC TACTGTACAG 1500

TCTGGAGGAA GTCACACAGC ATTGGGAGAT AGGAGTTATT CAGAGTCTTC ATCTACATCT 1560

TCCTCGGAAA GCTTGAATTC ATCAGCACCA CGTGGAGAAC GTTCAACCTT GGAAGACAGC 1620

CGAGAGCCAG GCCAAGCACT AGGTGACAGT TCCGCCAATG CAGAGGACAG GACTTCTGGG 1680

GTGCCCTCTC TCGGCACCCA CACCTTGGCT ACTGTCACTG GAAACGGGGA ACGCACACTG 1740

CGGTCTGTCA CCCTCACCAA CACCAGCATG AGCACGACTT CTGGGGAAGC AGGCAGCCCT 1800

GCAGCGGCCA TGCCCCAAGA AACAGAGGGT GCCTCTCTGC ACGTAAACGT GACGGACGAC 1860

ATGGGCCTGG TCTCACGGTC ACTGGCCGCC TCCAGTGCAC TCGGAGTCGC TGGGATTAGC 1920

TACGGTCAAG TGCGTGGCAC AGCTATTGAA CAAAGGACTT CCAGCGACCA CACAGACCAC 1980

ACCTACCTGT CATCTACTTT CACCAAAGGA GAACGGGCGT TACTGTCCAT TACAGATAAC 2040

AGTTCATCCT CAGACATTGT GGAGAGCTCA ACTTCTTATA TTAAAATCTC AAACTCTTCA 2100

-continued

CATTCAGAGT ATTCCTCCTT TTCTCATGCT CAGACTGAGA GAAGTAACAT CTCATCCTAT 2160

GACGGGGAAT ATGCTCAGCC TTCTACTGAG TCGCCAGTTC TGCATACATC CAACCTTCCG 2220

TCCTACACAC CCACCATTAA TATGCCGAAC ACTTCGGTTG TTCTGGACAC TGATGCTGAG 2280

TTTGTTAGTG ACTCCTCCTC CTCCTCTTCC TCCTCCTCCT CTTCTTCTTC TTCAGGGCCT 2340

CCTTTGCCTC TGCCCTCTGT GTCACAATCC CACCATTTAT TTTCATCAAT TTTACCATCA 2400

ACCAGGGCCT CTGTGCATCT ACTAAAGTCT ACCTCTGATG CATCCACACC ATGGTCTTCC 2460

TCACCATCAC CTTTACCAGT ATCCTTAACG ACATCTACAT CTGCCCCACT TTCTGTCTCA 2520

CAAACAACCT TGCCACAGTC ATCTTCTACC CCTGTCCTGC CCAGGGCAAG GGAGACTCCT 2580

GTGACTTCAT TTCAGACATC AACAATGACA TCATTCATGA CAATGCTCCA TAGTAGTCAA 2640

ACTGCAGACC TTAAGAGCCA GAGCACCCCA CACCAAGAGA AAGTCATTAC AGAATCAAAG 2700

TCACCAAGCC TGGTGTCTCT GCCCACAGAG TCCACCAAAG CTGTAACAAC AAACTCTCCT 2760

TTGCCTCCAT CCTTAACAGA GTCCTCCACA GAGCAAACCC TTCCAGCCAC AAGCACCAAC 2820

TTAGCACAAA TGTCTCCAAC TTTCACAACT ACCATTCTGA AGACCTCTCA GCCTCTTATG 2880

ACCACTCCTG GCACCCTGTC AAGCACAGCA TCTCTGGTCA CTGGCCCTAT AGCCGTACAG 2940

ACTACAGCTG GAAAACAGCT CTCGCTGACC CATCCTGAAA TACTAGTTCC TCAAATCTCA 3000

ACAGAAGGTG GCATCAGCAC AGAAAGGAAC CGAGTGATTG TGGATGCTAC CACTGGATTG 3060

ATCCCTTTGA CCAGTGTACC CACATCAGCA AAAGAAATGA CCACAAAGCT TGGCGTTACA 3120

GCAGAGTACA GCCCAGCTTC ACGTTCCCTC GGAACATCTC CTTCTCCCCA AACCACAGTT 3180

GTTTCCACGG CTGAAGACTT GGCTCCCAAA TCTGCCACCT TTGCTGTTCA GAGCAGCACA 3240

CAGTCACCAA CAACACTGTC CTCTTCAGCC TCAGTCAACA GCTGTGCTGT GAACCCTTGT 3300

CTTCACAATG GCGAATGCGT CGCAGACAAC ACCAGCCGTG GCTACCACTG CAGGTGCCCG 3360

CCTTCCTGGC AAGGGGATGA TTGCAGTGTG GATGTGAATG AGTGCCTGTC GAACCCCTGC 3420

CCATCCACAG CCACGTGCAA CAATACTCAG GGATCCTTTA TCTGCAAATG CCCGGTTGGG 3480

TACCAGTTGG AAAAAGGGAT ATGCAATTTG GTTAGAACCT TCGTGACAGA GTTTAAATTA 3540

AAGAGAACTT TTCTTAATAC AACTGTGGAA AAACATTCAG ACCTACAAGA AGTTGAAAAT 3600

GAGATCACCA AAACGTTAAA TATGTGTTTT TCAGCGTTAC CTAGTTACAT CCGATCTACA 3660

GTTCACGCCT CTAGGGAGTC CAACGCGGTG GTGATCTCAC TGCAAACAAC CTTTTCCCTG 3720

GCCTCCAATG TGACGCTATT TGACCTGGCT GATAGGATGC AGAAATGTGT CAACTCCTGC 3780

AAGTCCTCTG CTGAGGTCTG CCAGCTCTTG GGATCTCAGA GGCGGATCTT TAGAGCGGGC 3840

AGCTTGTGCA AGCGGAAGAG TCCCGAATGT GACAAAGACA CCTCCATCTG CACTGACCTG 3900

GACGGCGTTG CCCTGTGCCA GTGCAAGTCG GGATACTTTC AGTTCAACAA GATGGACCAC 3960

TCCTGCCGAG CATGTGAAGA TGGATATAGG CTTGAAAATG AAACCTGCAT GAGTTGCCCA 4020

TTTGGCCTTG GTGGTCTCAA CTGTGGAAAC CCCTATCAGC TTATCACTGT GGTGATCGCA 4080

GCCGCGGGAG GTGGGCTCCT GCTCATCCTA GGCATCGCAC TGATTGTTAC CTGTTGCAGA 4140

AAGAATAAAA ATGACATAAG CAAACTCATC TTCAAAAGTG GAGATTTCCA AATGTCCCCA 4200

TATGCTGAAT ACCCCAAAAA TCCTCGCTCA CAAGAATGGG GCCGAGAAGC TATTGAAATG 4260

CATGAGAATG GAAGTACCAA AAACCTCCTC CAGATGACGG ATGTGTACTA CTCGCCTACA 4320

AGTGTAAGGA ATCCAGAACT TGAACGAAAC GGACTCTACC CGGCCTACAC TGGACTGCCA 4380

GGATCACGGC ATTCTTGCAT TTTCCCCGGA CAGTATAACC CGTCTTTCAT CAGTGATGAA 4440

AGCAGAAGAA GAGACTACTT TTAAGTCCAG GAGAGAGAGG GACTCATTGC TCTGAGCCAG 4500

-continued

TCACCTGGGA CCTCTGCTCA GAGGACCGCA CCAGGAGGCT GCGCCCAGGA TTTGTCGGGA 4560

GCCACGCTGA GTGGCAAGCA GGAAGAGGGA CAGGCATGCG GGGCGTGACC ACAGTGGAGG 4620

AGACAGGTGG ATGTGGAACC ACAGGCTGCT CATTCAGCAC CTTTGTTGTT ACTGTGAACG 4680

TGAATGTGGG CCAGTATCAA GAGAGTCTCT CTGAGTGACT GCACCATGGC ACTGGCACCA 4740

GGGCGACTAT TAGCCAGGGC AGACCACTAG ACTTCAGTGC AGGGACCTGG TTTTCCCTTC 4800

GTTTGCACTT TAGTAAATTG GGTGGGAGGT TTCCTTTTGG ATCTGTTTTG AGACTGTTCC 4860

AGAAAGAAGG CTTCCTTTCC CGAGACACTT CCATAGGCAG CAATTTGGTG ATTCAYTTGC 4920

ASCAAAATAC TGGCTTGTTA ATTATTTTCC TGCCCAGCRC CTGCGTGCTA AACAACAGAT 4980

GAGGATGASC GTACCACTGA AGTCTGAAGA TGTCGCCATT GAACGGACAG TGTTTTCATA 5040

TGTTTCTAGG TTGTCTTATG CTACAGTTTC CAAGCCASCC CCCACAGTGA GGAAATGTGT 5100

GAGGCACCGC ACACAACTGC AATGTGTTTY TTAAGTCAAG GTGACACATG TATTTAAGAT 5160

TTTTTTTTAA AATCTCYTTG CAGTTAAATC TCACTTTYTC AAACAAGCCT GGATCAGGGC 5220

AAAACAACTT ATATYTGGTT TTAGCTGGAG GCTCAGCAGG CAGATTGCAG GCAGGGGGGC 5280

ACTTTTCATC CATGAGGGCC CAGCCTGGGG CCTGGGACTC TGATCACCAT TGTGGAGGCC 5340

AGAGGCAMCT GCGTATGGAG GAGAAATGTC AAACTGAACG CAGGTTTCAC CACTCTAGGA 5400

AAGCAGCTTG TTGACCCCCT GCASCTGGAT GTGGTTAGAG GGATGGGCTG AATAGSCAGG 5460

TTAGATTTCC TGCATCAACA GTGCTTTGGG AASCTGTGTG GATTCCTGAG GAAGAACAGG 5520

GAGCCGAGAT GGAGCCACAC ATGAATTYGC TCACCGGCTA CTGCAGCACT TTGTACCCAG 5580

AATCTCATGT CCACAAACCC CATGTAAACT TTCAACCACT CAAAGSTGTT TATTCGGCTG 5640

AAGAAATAAC TTTTKTTTCT CACCCAGTCA TTTGTACCTC TTCATATGGS TATGTCGCAC 5700

CCTCCAGAAA CGTGGTTATA CTKCCAGTCA GTGTGGGAGA ACTGAAGACT TCCGGTTGGT 5760

CGAGGAACTG AGGGTTGACC TTCGGGAAGG AAGTTCCACT CATCTTATTT ATTATGCCTG 5820

TGATGTGGGT CCTGCCAGGG AGACATCCAG TACTCGGTGT CTKTAATTGC CACCTGGGGA 5880

ACTGTGTTTA TTGGCCTTCT TTGGGGCATC CTGGKTTCGG ATGAAGTGAG GGGAATACAG 5940

AGGTAAAAGA ATTGTCTCCA CCCTGAAGCG GGGAGTCCCG CTTCACATTT CTGGAAATGG 6000

TGCAGCCACT GGGGACAGTT CTGCCCCGGG CATGGTTGTT TCTTCAAGGT CCTCTAAATA 6060

TAATCCCTAT TCTTACATAA TCCTTGGCCC TGATGGTTTT AAGCAAGAAC TCCTGTGTCC 6120

MATGGTCTCC ACCACTCACC ATCACCCTGC TGTAGCAAGA GTCCTAGTCA GGGGAGGTGC 6180

ATTTTAGTAG TTACATTGCA CTTATCCATG AGATAAATAA AAGGAGAVCT GTTTTTATCA 6240

GTGGAGGCTA ACCTAAAATT TCAAAGTGTC GCCTTTTTGA AATCTTGGGC CTCTCTCTCT 6300

GTAGAACCAA TGCCCCTTTG TGGCTCACGG CCTCGCACCT AACTGGAGAG TTCTGAGCTC 6360

CTGCAGCTCA CCTGAGCCCA CAGACTAGGC TTCTTGGCTC CTTCCGC 6407

( 2 ) INFORMATION FOR SEQ ID NO:8:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( i x ) FEATURE:
( A ) NAME/KEY: misc_feature

-continued ( B ) LOCATION: 12

( x i ) SEQUENCE DESCRIPTION: SEQ ID NO:8:

T T T T T T T T T T   T N G   1 3

( 2 ) INFORMATION FOR SEQ ID NO:9:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:9:

A G C A T G G C T C   1 0

( 2 ) INFORMATION FOR SEQ ID NO:10:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:10:

C A C C C C T G G C   A T C T T C T C C T   T C C   2 3

( 2 ) INFORMATION FOR SEQ ID NO:11:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:11:

A T C C T C C C C C   A G T T C A C C C C   A T C C   2 4

( 2 ) INFORMATION FOR SEQ ID NO:12:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:12:

C C T G A T A G A T   G G G C A C T G T G   T   2 1

( 2 ) INFORMATION FOR SEQ ID NO:13:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:13:

GAACACGGCA TTGTCACTAA CT 22

( 2 ) INFORMATION FOR SEQ ID NO:14:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:14:

AAGTCGCGCC CGCCCCTGAA AT 22

( 2 ) INFORMATION FOR SEQ ID NO:15:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:15:

GATCCCTGGC CACCGTCCGT CTGA 24

( 2 ) INFORMATION FOR SEQ ID NO:16:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:16:

ACCCTGAAGT ACCCCAT 17

( 2 ) INFORMATION FOR SEQ ID NO:17:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: other nucleic acid (A) DESCRIPTION: /desc = "synthetic oligonucleotide"

(iii) HYPOTHETICAL: NO (xi) SEQUENCE DESCRIPTION: SEQ ID NO:17:

TAGAAGCATT TGCGGTG 17

(2) INFORMATION FOR SEQ ID NO:18:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(iii) HYPOTHETICAL: NO (xi) SEQUENCE DESCRIPTION: SEQ ID NO:18:

AGATGCAGCC 10

(2) INFORMATION FOR SEQ ID NO:19:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(iii) HYPOTHETICAL: NO (ix) FEATURE:
(A) NAME/KEY: misc_feature
(B) LOCATION: 12

(xi) SEQUENCE DESCRIPTION: SEQ ID NO:19:

TTTTTTTTTT TNA 13

(2) INFORMATION FOR SEQ ID NO:20:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(iii) HYPOTHETICAL: NO (xi) SEQUENCE DESCRIPTION: SEQ ID NO:20:

TCTCCCTCAG 10

(2) INFORMATION FOR SEQ ID NO:21:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic oligonucleotide"

(iii) HYPOTHETICAL: NO ( i x ) FEATURE:
( A ) NAME/KEY: misc_feature
( B ) LOCATION: 12

( x i ) SEQUENCE DESCRIPTION: SEQ ID NO:21:

T T T T T T T T T T   T N C   1 3

( 2 ) INFORMATION FOR SEQ ID NO:22:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:22:

T G G A G A G C A G   1 0

( 2 ) INFORMATION FOR SEQ ID NO:23:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:23:

A T T T A T A A A G   G G G T A A T T C A   T T A   2 3

( 2 ) INFORMATION FOR SEQ ID NO:24:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:24:

T T A A A G C C A A   T T T C A A A A T A   A T   2 2

( 2 ) INFORMATION FOR SEQ ID NO:25:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:25:

G G T G G T G A T G   1 0

( 2 ) INFORMATION FOR SEQ ID NO:26:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:26:

G G T G C G G G A A 1 0

( 2 ) INFORMATION FOR SEQ ID NO:27:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:27:

A C A T G C C G T G 1 0

( 2 ) INFORMATION FOR SEQ ID NO:28:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:28:

A T G C C G T G T G G G T T A G T C 1 8

( 2 ) INFORMATION FOR SEQ ID NO:29:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:29:

A T T T T A T G G G A A G G T T T T T A C A 2 2

( 2 ) INFORMATION FOR SEQ ID NO:30:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:30:

A A T G C G G G A G 1 0

( 2 ) INFORMATION FOR SEQ ID NO:31:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( i x ) FEATURE:
( A ) NAME/KEY: misc_feature
( B ) LOCATION: 12..13

( x i ) SEQUENCE DESCRIPTION: SEQ ID NO:31:

T T T T T T T T T T T N N 1 3

( 2 ) INFORMATION FOR SEQ ID NO:32:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:32:

T T T T T T T T T T T C C 1 3

( 2 ) INFORMATION FOR SEQ ID NO:33:

( i ) SEQUENCE CHARACTERISTICS:
( A ) LENGTH: 10 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:33:

G T G A C A T G C C 1 0

( 2 ) INFORMATION FOR SEQ ID NO:34:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:34:

CATGCCTGTA GAAAAAGGTT 20

( 2 ) INFORMATION FOR SEQ ID NO:35:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( i i i ) HYPOTHETICAL: NO ( x i ) SEQUENCE DESCRIPTION: SEQ ID NO:35:

CTTCATAGAA TCTAAGCCTA 20

( 2 ) INFORMATION FOR SEQ ID NO:36:

( i ) SEQUENCE CHARACTERISTICS:
( A ) LENGTH: 3083 base pairs
( B ) TYPE: nucleic acid
( C ) STRANDEDNESS: both
( D ) TOPOLOGY: unknown ( i i ) MOLECULE TYPE: cDNA ( i x ) FEATURE:
( A ) NAME/KEY: misc_feature
( B ) LOCATION: 16

( i x ) FEATURE:
( A ) NAME/KEY: misc_feature
( B ) LOCATION: 30

( i x ) FEATURE:
( A ) NAME/KEY: misc_feature
( B ) LOCATION: 2911

( x i ) SEQUENCE DESCRIPTION: SEQ ID NO:36:

GAATTCGGCA CGAGGMCAGG AGCTCCTTTW CTGCGTCTCC CATCATGGGG CTTAGGGTTG 60

AGTCTTCAGG TTCTGGGGGC AGGAAGGACG GGCACTCAGG AGGCCCCCTC CCCATCCACA 120

GCCCCTCTTT GGGAGGGGGG AAACTTGGCA ACCCGGGAGG CATGTGGATC TTTTCCTAAG 180

CAAGATGCTG AGCTGGAAAG ATGGGGGTGT AAGGTAATGT CCCAAACTGA AACTTTGCCA 240

GGCACTGGGA GAGGCTGTGA ACTCTTTTCT GGCTTTAGAA TTTAGGTCTA GATCCCAAAA 300

GGCTAAGTAC CCCCTGGGGG CTAACCAGAG GCATGCCTGG GCTGAGCTGA ACCTTCTGGT 360

GCACTGGCCC CTGGCTGACT GCTCTTCTGC AGGAAGTTGG AGGAGATTCC TGAAGTTGAT 420

TCCTCAGGCT GGATGTCCAA GGGGGTTGGA GTTTCTGATG TCTTTCTGTC TCCCTCTCTT 480

TTCTTTCTCT CCCTACCAGG TCCACTTCTT TCAGAGGGGC CTGCGGTGCT CTAAAAGTTC 540

TCCTGTTAAA GTTTAGAGCA AATTGGTTAT TATTTTAAAA TCAATAAAAC TTTTAAAAGT 600

ACTAAGACAA CTTCTAAGAG GGGAGTGGAC AGAGGGCCTG GTGGCAGCTC ACAGTTTCTT 660

TTCTGACCTT TGGTCTCACC CACCAAGTGT CCCACCTGAG TGCCCACCTT GCCCACCTGA 720

GGTAATGCCC TGGGGCTCCA CCAGTCCAGA TCCACAGGGC GCAGCCATGT GGGAGTGGCG 780

GCTGATTGTT ACCCAGTAGT GTTGATAGCA CATTATTCAT AACAGCCAAA GAGAGGAAGC 840

AACCCAAATG TCCATTAGCT GATAAATGGA TAAATGAAAT ATGGTACGTC CGAAGAATGG 900

AATATCATTC ACCCATGAAA AAGAACGAAG TCCAGCACCA AAACGTGCTA CAACATGGAT 960

-continued

GAACTTCGAT GACTTTGTGC CACATGAAAG AAGAAGCCAG CCACAAAAGG CCATATATTG 1020

TATGAAATGA AATGTCCAGA ATGGGCAAAC CCATAGAGAC ACAAAAATCT CCGCCACCTC 1080

CCTACTCTCG GCTGTCTCCT CGCGACGAGT ACAAGCCACT GGATCTGTCC GATTCCACAT 1140

TGTCTTACAC TGAAACGGAG GCTACCAACT CCCTCATCAC TGCTCCGGGT GAATTCTCAG 1200

ACGCCAGCAT GTCTCCGGAC GCCACCAAGC CGAGCCACTG GTGCAGCGTG GCGTACTGGG 1260

AGCACCGGAC GCGCGTGGGC CGCCTCTATG CGGTGTACGA CCAGGCCGTC AGCATCTTCT 1320

ACGACCTACC TCAGGGCAGC GGCTTCTGCC TGGGCCAGCT CAACCTGGAG CAGCGCAGCG 1380

AGTCGGTGCG GCGAACGCGC AGCAAGATCG GCTTCGGCAT CCTGCTCAGC AAGGAGCCCG 1440

ACGGCGTGTG GGCCTACAAC CGCGGCGAGC ACCCCATCTT CGTCAACTCC CCGACGCTGG 1500

ACGCGCCCGG CGGCCGCGCC CTGGTCGTGC GCAAGGTGCC CCCCGGCTAC TCCATCAAGG 1560

TGTTCGACTT CGAGCGCTCG GGCCTGCAGC ACGCGCCCGA GCCCGACGCC GCCGACGGCC 1620

CCTACGACCC CAACAGCGTC CGCATCAGCT TCGCCAAGGG CTGGGGGCCC TGCTACTCCC 1680

GGCAGTTCAT CACCTCCTGC CCCTGCTGGC TGGAGATCCT CCTCAACAAC CCCAGATAGT 1740

GGCGGCCCCG GCGGGAGGGG CGGGTGGGAG GCCGCGGCCA CCGCCACCTG CCGGCCTCGA 1800

GAGGGGCCGA TGCCCAGAGA CACAGCCCCC ACGGACAAAA CCCCCCAGAT ATCATCTACC 1860

TAGATTTAAT ATAAAGTTTT ATATATTATA TGGAAATATA TATTATACTT GTAATTATGG 1920

AGTCATTTTT ACAATGTAAT TATTTATGTA TGGTGCAATG TGTGTATATG GACAAAACAA 1980

GAAAGACGCA CTTTGGCTTA TAATTCTTTC AATACAGATA TATTTTCTTT CTCTTCCTCC 2040

TTCCTCTTCC TTACTTTTTA TATATATATA TAAAGAAAAT GATACAGCAG AGCTAGGTGG 2100

AAAAGCCTGG GTTTGGTGTA TGGTTTTTGA GATATTAATG CCCAGACAAA AAGCTAATAC 2160

CAGTCACTCG ATAATAAAGT ATTCGCATTA TAGTTTTTTT TAAACTGTCT TCTTTTTACA 2220

AAGAGGGGCA GGTAGGGCTT CAGCGGATTT CTGACCCATC ATGTACCTTG AAACTTGACC 2280

TCAGTTTTCA AGTTTTACTT TTATTGGATA AAGACAGAAC AAATTGAAAA GGGAGGAAAG 2340

TCACATTTAC TCTTAAGTAA ACCAGAGAAA GTTCTGTTGT TCCTTCCTGC CCATGGCTAT 2400

GGGGTGTCCA GTGGATAGGG ATGGCGGTGG GGAAAAGGAG AATACACTGG CCATTTATCC 2460

TGGACAAGCT CTTCCAGTCT GATGGAGGAG GTTCATGCCC TAGCCTAGAA AGGCCCAGGT 2520

CCATGACCCC CATCTTTGAG TTATGAGCAA GCTAAAAGAA GACACTATTT CTCACCATTT 2580

TGTGGAAATG GCCTGGGGAA CAAAGACTGA AATGGGCCTT GAGCCCACCT GCTACCTTGC 2640

AGAGAACCAT CTCGAGCCCC GTAGATCTTT TTAGGACCTC CACAGGCTAT TTCCCACCCC 2700

CCAGCCAAAA ATAGCTCAGA ATCTGCCCAT CCAGGGCTGT ATTAATGATT TATGTAAAGG 2760

CAGATGGTTT ATTTCTACTT TGTAAAAGGG AAAAGTTGAG GTTCTGGAAG GATAAATGAT 2820

TTGCTCATGA GACAAAATCA AGGTTAGAAG TTACATGGAA TTGTAGGACC AGAGCCATAT 2880

CATTAGATCA GCTTTCTGAA GAATATTCTC MAAAAAAGAA AGTCTCCTTG GCCAGATAAC 2940

TAAGAGGAAT GTTTCATTGT ATATCTTTTT TCTTGGAGAT TTATATTAAC ATATTAAGTG 3000

CTCTGAGAAG TCCTGTGTAT TATCTCTTGC TGCATAATAA ATTATCCCCA AACTTAAAAA 3060

AAAAAAAAAA AAAAAAACTC GAG 3083

( 2 ) INFORMATION FOR SEQ ID NO:37:

( i ) SEQUENCE CHARACTERISTICS:
( A ) LENGTH: 235 amino acids
( B ) TYPE: amino acid
( C ) STRANDEDNESS:

-continued ( D ) TOPOLOGY: unknown ( i i ) MOLECULE TYPE: protein ( x i ) SEQUENCE DESCRIPTION: SEQ ID NO:37:

Met Ser Arg Met Gly Lys Pro Ile Glu Thr Gln Lys Ser Pro Pro Pro
1 5 10 15

Pro Tyr Ser Arg Leu Ser Pro Arg Asp Glu Tyr Lys Pro Leu Asp Leu
20 25 30

Ser Asp Ser Thr Leu Ser Tyr Thr Glu Thr Glu Ala Thr Asn Ser Leu
35 40 45

Ile Thr Ala Pro Gly Glu Phe Ser Asp Ala Ser Met Ser Pro Asp Ala
50 55 60

Thr Lys Pro Ser His Trp Cys Ser Val Ala Tyr Trp Glu His Arg Thr
65 70 75 80

Arg Val Gly Arg Leu Tyr Ala Val Tyr Asp Gln Ala Val Ser Ile Phe
85 90 95

Tyr Asp Leu Pro Gln Gly Ser Gly Phe Cys Leu Gly Gln Leu Asn Leu
100 105 110

Glu Gln Arg Ser Glu Ser Val Arg Arg Thr Arg Ser Lys Ile Gly Phe
115 120 125

Gly Ile Leu Leu Ser Lys Glu Pro Asp Gly Val Trp Ala Tyr Asn Arg
130 135 140

Gly Glu His Pro Ile Phe Val Asn Ser Pro Thr Leu Asp Ala Pro Gly
145 150 155 160

Gly Arg Ala Leu Val Val Arg Lys Val Pro Pro Gly Tyr Ser Ile Lys
165 170 175

Val Phe Asp Phe Glu Arg Ser Gly Leu Gln His Ala Pro Glu Pro Asp
180 185 190

Ala Ala Asp Gly Pro Tyr Asp Pro Asn Ser Val Arg Ile Ser Phe Ala
195 200 205

Lys Gly Trp Gly Pro Cys Tyr Ser Arg Gln Phe Ile Thr Ser Cys Pro
210 215 220

Cys Trp Leu Glu Ile Leu Leu Asn Asn Pro Arg
225 230 235

( 2 ) INFORMATION FOR SEQ ID NO:38:

( i ) SEQUENCE CHARACTERISTICS:
( A ) LENGTH: 375 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:38:

Met Asp Val Thr Ser Gln Ala Arg Gly Val Gly Leu Glu Met Tyr Pro
1 5 10 15

Gly Thr Ala Gln Pro Ala Ala Pro Asn Thr Thr Ser Pro Glu Leu Asn
20 25 30

Leu Ser His Pro Leu Leu Gly Thr Ala Leu Ala Asn Gly Thr Gly Glu
35 40 45

Leu Ser Glu His Gln Gln Tyr Val Ile Gly Leu Phe Leu Ser Cys Leu
50 55 60

Tyr Thr Ile Phe Leu Phe Pro Ile Gly Phe Val Gly Asn Ile Leu Ile
65 70 75 80

Leu Val Val Asn Ile Ser Phe Arg Glu Lys Met Thr Ile Pro Asp Leu

-continued 85 90 95

Tyr Phe Ile Asn Leu Ala Val Ala Asp Leu Ile Leu Val Ala Asp Ser
100 105 110

Leu Ile Glu Val Phe Asn Leu His Glu Arg Tyr Tyr Asp Ile Ala Val
115 120 125

Leu Cys Thr Phe Met Ser Leu Phe Leu Arg Val Asn Met Tyr Ser Ser
130 135 140

Val Phe Phe Leu Thr Trp Met Ser Phe Asp Arg Tyr Ile Ala Leu Ala
145 150 155 160

Arg Ala Met Arg Cys Ser Leu Phe Arg Thr Lys His His Ala Arg Leu
165 170 175

Ser Cys Gly Leu Ile Trp Met Ala Ser Val Ser Ala Thr Leu Val Pro
180 185 190

Phe Thr Ala Val His Leu Gln His Thr Asp Glu Ala Cys Phe Cys Phe
195 200 205

Ala Asp Val Arg Glu Val Gln Trp Leu Glu Val Thr Leu Gly Phe Ile
210 215 220

Val Pro Phe Ala Ile Ile Gly Leu Cys Tyr Ser Leu Ile Val Arg Val
225 230 235 240

Leu Val Arg Ala His Arg His Arg Gly Leu Arg Pro Arg Arg Gln Lys
245 250 255

Ala Leu Arg Met Ile Leu Ala Val Val Leu Val Phe Phe Val Cys Trp
260 265 270

Leu Pro Glu Asn Val Phe Ile Ser Val His Leu Leu Gln Arg Thr Gln
275 280 285

Pro Gly Ala Ala Pro Cys Lys Gln Ser Phe Arg His Ala His Pro Leu
290 295 300

Thr Gly His Ile Val Asn Leu Ala Ala Phe Ser Asn Ser Cys Leu Asn
305 310 315 320

Pro Leu Ile Tyr Ser Phe Leu Gly Glu Thr Phe Arg Asp Lys Leu Arg
325 330 335

Leu Tyr Ile Glu Gln Lys Thr Asn Leu Pro Ala Leu Asp Arg Phe Cys
340 345 350

His Ala Ala Leu Lys Ala Val Ile Pro Asp Ser Thr Glu Gln Ser Asp
355 360 365

Val Arg Phe Ser Ser Ala Val
370 375

( 2 ) INFORMATION FOR SEQ ID NO:39:

( i ) SEQUENCE CHARACTERISTICS:
( A ) LENGTH: 643 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:39:

Met Gly Leu Leu Pro Lys Leu Gly Ala Ser Gln Gly Ser Asp Thr Ser
1 5 10 15

Thr Ser Arg Ala Gly Arg Cys Ala Arg Ser Val Phe Gly Asn Ile Lys
20 25 30

Val Phe Val Leu Cys Gln Gly Leu Leu Gln Leu Cys Gln Leu Leu Tyr
35 40 45

Ser Ala Tyr Phe Lys Ser Ser Leu Thr Thr Ile Glu Lys Arg Phe Gly
50 55 60

-continued

| | | | | | | | | | | | | | | | |
|---|---|---|---|---|---|---|---|---|---|---|---|---|---|---|---|
| Leu | Ser | Ser | Ser | Ser | Ser | Gly | Leu | Ile | Ser | Ser | Leu | Asn | Glu | Ile | Ser |
| 65 | | | | | 70 | | | | | 75 | | | | | 80 |
| Asn | Ala | Ile | Leu | Ile | Ile | Phe | Val | Ser | Tyr | Phe | Gly | Ser | Arg | Val | His |
| | | | | 85 | | | | | 90 | | | | | 95 | |
| Arg | Pro | Arg | Leu | Ile | Gly | Ile | Gly | Gly | Leu | Phe | Leu | Ala | Ala | Gly | Ala |
| | | | 100 | | | | | 105 | | | | | 110 | | |
| Phe | Ile | Leu | Thr | Leu | Pro | His | Phe | Leu | Ser | Glu | Pro | Tyr | Gln | Tyr | Thr |
| | | 115 | | | | | 120 | | | | | 125 | | | |
| Leu | Ala | Ser | Thr | Gly | Asn | Asn | Ser | Arg | Leu | Gln | Ala | Glu | Leu | Cys | Gln |
| | 130 | | | | | 135 | | | | | 140 | | | | |
| Lys | His | Trp | Gln | Asp | Leu | Pro | Pro | Ser | Lys | Cys | His | Ser | Thr | Thr | Gln |
| 145 | | | | | 150 | | | | | 155 | | | | | 160 |
| Asn | Pro | Gln | Lys | Glu | Thr | Ser | Ser | Met | Trp | Gly | Leu | Met | Val | Val | Ala |
| | | | | 165 | | | | | 170 | | | | | 175 | |
| Gln | Leu | Leu | Ala | Gly | Ile | Gly | Thr | Val | Pro | Ile | Gln | Pro | Phe | Gly | Ile |
| | | | 180 | | | | | 185 | | | | | 190 | | |
| Ser | Tyr | Val | Asp | Asp | Phe | Ser | Glu | Pro | Ser | Asn | Ser | Pro | Leu | Tyr | Ile |
| | | 195 | | | | | 200 | | | | | 205 | | | |
| Ser | Ile | Leu | Phe | Ala | Ile | Ser | Val | Phe | Gly | Pro | Ala | Phe | Gly | Tyr | Leu |
| | 210 | | | | | 215 | | | | | 220 | | | | |
| Leu | Gly | Ser | Val | Met | Leu | Gln | Ile | Phe | Val | Asp | Tyr | Gly | Arg | Val | Asn |
| 225 | | | | | 230 | | | | | 235 | | | | | 240 |
| Thr | Ala | Ala | Val | Asn | Leu | Val | Pro | Gly | Asp | Pro | Arg | Trp | Ile | Gly | Ala |
| | | | | 245 | | | | | 250 | | | | | 255 | |
| Trp | Trp | Leu | Gly | Leu | Leu | Ile | Ser | Ser | Ala | Leu | Leu | Val | Leu | Thr | Ser |
| | | | 260 | | | | | 265 | | | | | 270 | | |
| Phe | Pro | Phe | Phe | Phe | Phe | Pro | Arg | Ala | Met | Pro | Ile | Gly | Ala | Lys | Arg |
| | | 275 | | | | | 280 | | | | | 285 | | | |
| Ala | Pro | Ala | Thr | Ala | Asp | Glu | Ala | Arg | Lys | Leu | Glu | Glu | Ala | Lys | Ser |
| | 290 | | | | | 295 | | | | | 300 | | | | |
| Arg | Gly | Ser | Leu | Val | Asp | Phe | Ile | Lys | Arg | Phe | Pro | Cys | Ile | Phe | Leu |
| 305 | | | | | 310 | | | | | 315 | | | | | 320 |
| Arg | Leu | Leu | Met | Asn | Ser | Leu | Phe | Val | Leu | Val | Val | Leu | Ala | Gln | Cys |
| | | | | 325 | | | | | 330 | | | | | 335 | |
| Thr | Phe | Ser | Ser | Val | Ile | Ala | Gly | Leu | Ser | Thr | Phe | Leu | Asn | Lys | Phe |
| | | | 340 | | | | | 345 | | | | | 350 | | |
| Leu | Glu | Lys | Gln | Tyr | Gly | Thr | Ser | Ala | Ala | Tyr | Ala | Asn | Phe | Leu | Ile |
| | | 355 | | | | | 360 | | | | | 365 | | | |
| Gly | Ala | Val | Asn | Leu | Pro | Ala | Ala | Ala | Leu | Gly | Met | Leu | Phe | Gly | Gly |
| | 370 | | | | | 375 | | | | | 380 | | | | |
| Ile | Leu | Met | Lys | Arg | Phe | Val | Phe | Ser | Leu | Gln | Ala | Ile | Pro | Arg | Ile |
| 385 | | | | | 390 | | | | | 395 | | | | | 400 |
| Ala | Thr | Thr | Ile | Ile | Thr | Ile | Ser | Met | Ile | Leu | Cys | Val | Pro | Leu | Phe |
| | | | | 405 | | | | | 410 | | | | | 415 | |
| Phe | Met | Gly | Cys | Ser | Thr | Pro | Thr | Val | Ala | Glu | Val | Tyr | Pro | Pro | Ser |
| | | | 420 | | | | | 425 | | | | | 430 | | |
| Thr | Ser | Ser | Ser | Ile | His | Pro | Gln | Ser | Pro | Ala | Cys | Arg | Arg | Asp | Cys |
| | | 435 | | | | | 440 | | | | | 445 | | | |
| Ser | Cys | Pro | Asp | Ser | Ile | Phe | His | Pro | Val | Cys | Gly | Asp | Asn | Gly | Ile |
| | 450 | | | | | 455 | | | | | 460 | | | | |
| Glu | Tyr | Leu | Ser | Pro | Cys | His | Ala | Gly | Cys | Ser | Asn | Ile | Asn | Met | Ser |
| 465 | | | | | 470 | | | | | 475 | | | | | 480 |
| Ser | Ala | Thr | Ser | Lys | Gln | Leu | Ile | Tyr | Leu | Asn | Cys | Ser | Cys | Val | Thr |

-continued

| | | | | | | | | | | | | | | | |
|---|---|---|---|---|---|---|---|---|---|---|---|---|---|---|---|
| | | | | 485 | | | | | 490 | | | | | 495 | |
| Gly | Gly | Ser | Ala<br>500 | Ser | Ala | Lys | Thr | Gly<br>505 | Ser | Cys | Pro | Val | Pro<br>510 | Cys | Ala |
| His | Phe | Leu<br>515 | Leu | Pro | Ala | Ile | Phe<br>520 | Leu | Ile | Ser | Phe | Val<br>525 | Ser | Leu | Ile |
| Ala | Cys<br>530 | Ile | Ser | His | Asn | Pro<br>535 | Leu | Tyr | Met | Met | Val<br>540 | Leu | Arg | Val | Val |
| Asn<br>545 | Gln | Glu | Glu | Lys | Ser<br>550 | Phe | Ala | Ile | Gly | Val<br>555 | Gln | Phe | Leu | Leu | Met<br>560 |
| Arg | Leu | Leu | Ala | Trp<br>565 | Leu | Pro | Ser | Pro | Ala<br>570 | Leu | Tyr | Gly | Leu | Thr<br>575 | Ile |
| Asp | His | Ser | Cys<br>580 | Ile | Arg | Trp | Asn | Ser<br>585 | Leu | Cys | Leu | Gly | Arg<br>590 | Arg | Gly |
| Ala | Cys | Ala<br>595 | Tyr | Tyr | Asp | Asn | Asp<br>600 | Ala | Leu | Arg | Asp | Arg<br>605 | Tyr | Leu | Gly |
| Leu | Gln<br>610 | Met | Gly | Tyr | Lys | Ala<br>615 | Leu | Gly | Met | Leu | Leu<br>620 | Leu | Cys | Phe | Ile |
| Ser<br>625 | Trp | Arg | Val | Lys | Lys<br>630 | Asn | Lys | Glu | Tyr | Asn<br>635 | Val | Gln | Lys | Ala | Ala<br>640 |
| Gly | Leu | Ile | | | | | | | | | | | | | |

( 2 ) INFORMATION FOR SEQ ID NO:40:

( i ) SEQUENCE CHARACTERISTICS:
( A ) LENGTH: 1481 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:40:

| | | | | | | | | | | | | | | | |
|---|---|---|---|---|---|---|---|---|---|---|---|---|---|---|---|
| Met<br>1 | Ala | Ser | Pro | Arg<br>5 | Ala | Ser | Arg | Trp | Pro<br>10 | Pro | Pro | Leu | Leu | Leu<br>15 | Leu |
| Leu | Leu | Pro | Leu<br>20 | Leu | Leu | Leu | Pro | Pro<br>25 | Ala | Ala | Pro | Gly | Thr<br>30 | Arg | Asp |
| Pro | Pro | Pro<br>35 | Ser | Pro | Ala | Arg | Arg<br>40 | Ala | Leu | Ser | Leu | Ala<br>45 | Pro | Leu | Ala |
| Gly | Ala<br>50 | Gly | Leu | Glu | Leu | Gln<br>55 | Leu | Glu | Arg | Arg | Pro<br>60 | Glu | Arg | Glu | Pro |
| Pro<br>65 | Pro | Thr | Pro | Pro | Arg<br>70 | Glu | Arg | Arg | Gly | Pro<br>75 | Ala | Thr | Pro | Gly | Pro<br>80 |
| Ser | Tyr | Arg | Ala | Pro<br>85 | Glu | Pro | Gly | Ala | Ala<br>90 | Thr | Gln | Arg | Gly | Pro<br>95 | Ser |
| Gly | Arg | Ala | Pro<br>100 | Arg | Gly | Gly | Ser | Ala<br>105 | Asp | Ala | Ala | Trp | Lys<br>110 | His | Trp |
| Pro | Glu | Ser<br>115 | Asn | Thr | Glu | Ala | His<br>120 | Val | Glu | Asn | Ile | Thr<br>125 | Phe | Tyr | Gln |
| Asn | Gln<br>130 | Glu | Asp | Phe | Ser | Thr<br>135 | Val | Ser | Ser | Lys | Glu<br>140 | Gly | Val | Met | Val |
| Gln<br>145 | Thr | Ser | Gly | Lys | Ser<br>150 | His | Ala | Ala | Ser | Asp<br>155 | Ala | Pro | Glu | Asn | Leu<br>160 |
| Thr | Leu | Leu | Ala | Glu<br>165 | Thr | Ala | Asp | Ala | Arg<br>170 | Gly | Arg | Ser | Gly | Ser<br>175 | Ser |
| Ser | Arg | Thr | Asn<br>180 | Phe | Thr | Ile | Leu | Pro<br>185 | Val | Gly | Tyr | Ser | Leu<br>190 | Glu | Ile |

-continued

Ala Thr Ala Leu Thr Ser Gln Ser Gly Asn Leu Ala Ser Glu Ser Leu
195 200 205

His Leu Pro Ser Ser Ser Ser Glu Phe Asp Glu Arg Ile Ala Ala Phe
210 215 220

Gln Thr Lys Ser Gly Thr Ala Ser Glu Met Gly Thr Glu Arg Ala Met
225 230 235 240

Gly Leu Ser Glu Glu Trp Thr Val His Ser Gln Glu Ala Thr Thr Ser
245 250 255

Ala Trp Ser Pro Ser Phe Leu Pro Ala Leu Glu Met Gly Glu Leu Thr
260 265 270

Thr Pro Ser Arg Lys Arg Asn Ser Ser Gly Pro Asp Leu Ser Trp Leu
275 280 285

His Phe Tyr Arg Thr Ala Ala Ser Ser Pro Leu Leu Asp Leu Ser Ser
290 295 300

Pro Ser Glu Ser Thr Glu Lys Leu Asn Asn Ser Thr Gly Leu Gln Ser
305 310 315 320

Ser Ser Val Ser Gln Thr Lys Thr Met His Val Ala Thr Val Phe Thr
325 330 335

Asp Gly Gly Pro Arg Thr Leu Arg Ser Leu Thr Val Ser Leu Gly Pro
340 345 350

Val Ser Lys Thr Glu Gly Phe Pro Lys Asp Ser Arg Ile Ala Thr Thr
355 360 365

Ser Ser Ser Val Leu Leu Ser Pro Ser Ala Val Glu Ser Arg Arg Asn
370 375 380

Ser Arg Val Thr Gly Asn Pro Gly Asp Glu Glu Phe Ile Glu Pro Ser
385 390 395 400

Thr Glu Asn Glu Phe Gly Leu Thr Ser Leu Arg Trp Gln Asn Asp Ser
405 410 415

Pro Thr Phe Gly Glu His Gln Leu Ala Ser Ser Ser Glu Val Gln Asn
420 425 430

Gly Ser Pro Met Ser Gln Thr Glu Thr Val Ser Arg Ser Val Ala Pro
435 440 445

Met Arg Gly Gly Glu Ile Thr Ala His Trp Leu Leu Thr Asn Ser Thr
450 455 460

Thr Ser Ala Asp Val Thr Gly Ser Ser Ala Ser Tyr Pro Glu Gly Val
465 470 475 480

Asn Ala Ser Val Leu Thr Gln Phe Ser Asp Ser Thr Val Gln Ser Gly
485 490 495

Gly Ser His Thr Ala Leu Gly Asp Arg Ser Tyr Ser Glu Ser Ser Ser
500 505 510

Thr Ser Ser Ser Glu Ser Leu Asn Ser Ser Ala Pro Arg Gly Glu Arg
515 520 525

Ser Thr Leu Glu Asp Ser Arg Glu Pro Gly Gln Ala Leu Gly Asp Ser
530 535 540

Ser Ala Asn Ala Glu Asp Arg Thr Ser Gly Val Pro Ser Leu Gly Thr
545 550 555 560

His Thr Leu Ala Thr Val Thr Gly Asn Gly Glu Arg Thr Leu Arg Ser
565 570 575

Val Thr Leu Thr Asn Thr Ser Met Ser Thr Thr Ser Gly Glu Ala Gly
580 585 590

Ser Pro Ala Ala Ala Met Pro Gln Glu Thr Glu Gly Ala Ser Leu His
595 600 605

Val Asn Val Thr Asp Asp Met Gly Leu Val Ser Arg Ser Leu Ala Ala
610 615 620

-continued

Ser Ser Ala Leu Gly Val Ala Gly Ile Ser Tyr Gly Gln Val Arg Gly
625 630 635 640

Thr Ala Ile Glu Gln Arg Thr Ser Ser Asp His Thr Asp His Thr Tyr
645 650 655

Leu Ser Ser Thr Phe Thr Lys Gly Glu Arg Ala Leu Leu Ser Ile Thr
660 665 670

Asp Asn Ser Ser Ser Ser Asp Ile Val Glu Ser Ser Thr Ser Tyr Ile
675 680 685

Lys Ile Ser Asn Ser Ser His Ser Glu Tyr Ser Ser Phe Ser His Ala
690 695 700

Gln Thr Glu Arg Ser Asn Ile Ser Ser Tyr Asp Gly Glu Tyr Ala Gln
705 710 715 720

Pro Ser Thr Glu Ser Pro Val Leu His Thr Ser Asn Leu Pro Ser Tyr
725 730 735

Thr Pro Thr Ile Asn Met Pro Asn Thr Ser Val Val Leu Asp Thr Asp
740 745 750

Ala Glu Phe Val Ser Asp Ser Ser Ser Ser Ser Ser Ser Ser Ser Ser
755 760 765

Ser Ser Ser Ser Gly Pro Pro Leu Pro Leu Pro Ser Val Ser Gln Ser
770 775 780

His His Leu Phe Ser Ser Ile Leu Pro Ser Thr Arg Ala Ser Val His
785 790 795 800

Leu Leu Lys Ser Thr Ser Asp Ala Ser Thr Pro Trp Ser Ser Ser Pro
805 810 815

Ser Pro Leu Pro Val Ser Leu Thr Thr Ser Thr Ser Ala Pro Leu Ser
820 825 830

Val Ser Gln Thr Thr Leu Pro Gln Ser Ser Ser Thr Pro Val Leu Pro
835 840 845

Arg Ala Arg Glu Thr Pro Val Thr Ser Phe Gln Thr Ser Thr Met Thr
850 855 860

Ser Phe Met Thr Met Leu His Ser Ser Gln Thr Ala Asp Leu Lys Ser
865 870 875 880

Gln Ser Thr Pro His Gln Glu Lys Val Ile Thr Glu Ser Lys Ser Pro
885 890 895

Ser Leu Val Ser Leu Pro Thr Glu Ser Thr Lys Ala Val Thr Thr Asn
900 905 910

Ser Pro Leu Pro Pro Ser Leu Thr Glu Ser Ser Thr Glu Gln Thr Leu
915 920 925

Pro Ala Thr Ser Thr Asn Leu Ala Gln Met Ser Pro Thr Phe Thr Thr
930 935 940

Thr Ile Leu Lys Thr Ser Gln Pro Leu Met Thr Thr Pro Gly Thr Leu
945 950 955 960

Ser Ser Thr Ala Ser Leu Val Thr Gly Pro Ile Ala Val Gln Thr Thr
965 970 975

Ala Gly Lys Gln Leu Ser Leu Thr His Pro Glu Ile Leu Val Pro Gln
980 985 990

Ile Ser Thr Glu Gly Gly Ile Ser Thr Glu Arg Asn Arg Val Ile Val
995 1000 1005

Asp Ala Thr Thr Gly Leu Ile Pro Leu Thr Ser Val Pro Thr Ser Ala
1010 1015 1020

Lys Glu Met Thr Thr Lys Leu Gly Val Thr Ala Glu Tyr Ser Pro Ala
1025 1030 1035 1040

Ser Arg Ser Leu Gly Thr Ser Pro Ser Pro Gln Thr Thr Val Val Ser

-continued 1045 1050 1055

Thr Ala Glu Asp Leu Ala Pro Lys Ser Ala Thr Phe Ala Val Gln Ser
1060 1065 1070

Ser Thr Gln Ser Pro Thr Thr Leu Ser Ser Ser Ala Ser Val Asn Ser
1075 1080 1085

Cys Ala Val Asn Pro Cys Leu His Asn Gly Glu Cys Val Ala Asp Asn
1090 1095 1100

Thr Ser Arg Gly Tyr His Cys Arg Cys Pro Pro Ser Trp Gln Gly Asp
1105 1110 1115 1120

Asp Cys Ser Val Asp Val Asn Glu Cys Leu Ser Asn Pro Cys Pro Ser
1125 1130 1135

Thr Ala Thr Cys Asn Asn Thr Gln Gly Ser Phe Ile Cys Lys Cys Pro
1140 1145 1150

Val Gly Tyr Gln Leu Glu Lys Gly Ile Cys Asn Leu Val Arg Thr Phe
1155 1160 1165

Val Thr Glu Phe Lys Leu Lys Arg Thr Phe Leu Asn Thr Thr Val Glu
1170 1175 1180

Lys His Ser Asp Leu Gln Glu Val Glu Asn Glu Ile Thr Lys Thr Leu
1185 1190 1195 1200

Asn Met Cys Phe Ser Ala Leu Pro Ser Tyr Ile Arg Ser Thr Val His
1205 1210 1215

Ala Ser Arg Glu Ser Asn Ala Val Val Ile Ser Leu Gln Thr Thr Phe
1220 1225 1230

Ser Leu Ala Ser Asn Val Thr Leu Phe Asp Leu Ala Asp Arg Met Gln
1235 1240 1245

Lys Cys Val Asn Ser Cys Lys Ser Ser Ala Glu Val Cys Gln Leu Leu
1250 1255 1260

Gly Ser Gln Arg Arg Ile Phe Arg Ala Gly Ser Leu Cys Lys Arg Lys
1265 1270 1275 1280

Ser Pro Glu Cys Asp Lys Asp Thr Ser Ile Cys Thr Asp Leu Asp Gly
1285 1290 1295

Val Ala Leu Cys Gln Cys Lys Ser Gly Tyr Phe Gln Phe Asn Lys Met
1300 1305 1310

Asp His Ser Cys Arg Ala Cys Glu Asp Gly Tyr Arg Leu Glu Asn Glu
1315 1320 1325

Thr Cys Met Ser Cys Pro Phe Gly Leu Gly Gly Leu Asn Cys Gly Asn
1330 1335 1340

Pro Tyr Gln Leu Ile Thr Val Val Ile Ala Ala Ala Gly Gly Gly Leu
1345 1350 1355 1360

Leu Leu Ile Leu Gly Ile Ala Leu Ile Val Thr Cys Cys Arg Lys Asn
1365 1370 1375

Lys Asn Asp Ile Ser Lys Leu Ile Phe Lys Ser Gly Asp Phe Gln Met
1380 1385 1390

Ser Pro Tyr Ala Glu Tyr Pro Lys Asn Pro Arg Ser Gln Glu Trp Gly
1395 1400 1405

Arg Glu Ala Ile Glu Met His Glu Asn Gly Ser Thr Lys Asn Leu Leu
1410 1415 1420

Gln Met Thr Asp Val Tyr Tyr Ser Pro Thr Ser Val Arg Asn Pro Glu
1425 1430 1435 1440

Leu Glu Arg Asn Gly Leu Tyr Pro Ala Tyr Thr Gly Leu Pro Gly Ser
1445 1450 1455

Arg His Ser Cys Ile Phe Pro Gly Gln Tyr Asn Pro Ser Phe Ile Ser
1460 1465 1470

Asp Glu Ser Arg Arg Arg Asp Tyr Phe
1475 1480

( 2 ) INFORMATION FOR SEQ ID NO:41:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( x i ) SEQUENCE DESCRIPTION: SEQ ID NO:41:

CCCATAGACT AGGCTCATAG 20

( 2 ) INFORMATION FOR SEQ ID NO:42:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( x i ) SEQUENCE DESCRIPTION: SEQ ID NO:42:

TTTAAAGAGA AATTCAAATC 20

( 2 ) INFORMATION FOR SEQ ID NO:43:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( x i ) SEQUENCE DESCRIPTION: SEQ ID NO:43:

CTTTTCTGCG TCTCCCAT 18

( 2 ) INFORMATION FOR SEQ ID NO:44:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic oligonucleotide"

( x i ) SEQUENCE DESCRIPTION: SEQ ID NO:44:

AGACATCAGA AACTCCAACC 20

( 2 ) INFORMATION FOR SEQ ID NO:45:

( i ) SEQUENCE CHARACTERISTICS:
( A ) LENGTH: 15 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:45:

-continued

Asp Glu Ala Arg Lys Leu Glu Glu Ala Lys Ser Arg Gly Ser Leu
1 5 10 15

( 2 ) INFORMATION FOR SEQ ID NO:46:

( i ) SEQUENCE CHARACTERISTICS:
( A ) LENGTH: 15 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:46:

Ser Ser Ile His Pro Gln Ser Pro Ala Cys Arg Arg Asp Cys Ser
1 5 10 15

( 2 ) INFORMATION FOR SEQ ID NO:47:

( i ) SEQUENCE CHARACTERISTICS:
( A ) LENGTH: 14 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:47:

Arg Val Lys Lys Asn Lys Glu Tyr Asn Val Gln Lys Ala Ala
1 5 10

( 2 ) INFORMATION FOR SEQ ID NO:48:

( i ) SEQUENCE CHARACTERISTICS:
( A ) LENGTH: 16 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:48:

Arg Ala His Arg His Arg Gly Leu Arg Pro Arg Arg Gln Lys Ala Leu
1 5 10 15

( 2 ) INFORMATION FOR SEQ ID NO:49:

( i ) SEQUENCE CHARACTERISTICS:
( A ) LENGTH: 13 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:49:

Ile Pro Asp Ser Thr Glu Gln Ser Asp Val Arg Phe Ser
1 5 10

( 2 ) INFORMATION FOR SEQ ID NO:50:

( i ) SEQUENCE CHARACTERISTICS:
( A ) LENGTH: 18 amino acids
( B ) TYPE: amino acid
( C ) STRANDEDNESS:
( D ) TOPOLOGY: unknown ( i i ) MOLECULE TYPE: peptide ( x i ) SEQUENCE DESCRIPTION: SEQ ID NO:50:

-continued

Ser Pro Tyr Ala Glu Tyr Pro Lys Asn Pro Arg Ser Gln Glu Trp Gly
1 5 10 15

Arg Glu (2) INFORMATION FOR SEQ ID NO:51:

(i) SEQUENCE CHARACTERISTICS:
(A) LENGTH: 15 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:51:

Asn Pro Ser Phe Ile Ser Asp Glu Ser Arg Arg Arg Asp Tyr Phe
1 5 10 15

(2) INFORMATION FOR SEQ ID NO:52:

(i) SEQUENCE CHARACTERISTICS:
(A) LENGTH: 16 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:52:

Glu Phe Ser Asp Ala Ser Met Ser Pro Asp Ala Thr Lys Pro Ser His
1 5 10 15

(2) INFORMATION FOR SEQ ID NO:53:

(i) SEQUENCE CHARACTERISTICS:
(A) LENGTH: 14 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:53:

Leu Glu Gln Arg Ser Glu Ser Val Arg Arg Thr Arg Ser Lys
1 5 10

(2) INFORMATION FOR SEQ ID NO:54:

(i) SEQUENCE CHARACTERISTICS:
(A) LENGTH: 16 amino acids
(B) TYPE: amino acid
(C) STRANDEDNESS:
(D) TOPOLOGY: unknown (ii) MOLECULE TYPE: peptide (xi) SEQUENCE DESCRIPTION: SEQ ID NO:54:

Arg Ser Gly Leu Gln His Ala Pro Glu Pro Asp Ala Ala Asp Gly Pro
1 5 10 15